United States Patent
Ciliberto et al.

(10) Patent No.: US 11,492,671 B2
(45) Date of Patent: Nov. 8, 2022

(54) MIRNAS FOR TREATMENT AND IN VITRO DIAGNOSIS OF DRUG RESISTANT TUMORS

(71) Applicants: ISTITUTI FISIOTERAPICI OSPITALIERI, Rome (IT); ISTITUTO NAZIONALE TUMORI I.R.C.C.S. "FONDAZIONE G. PASCALE", Naples (IT); UNIVERSITA' DEGLI STUDI DI ROMA "LA SAPIENZA", Rome (IT)

(72) Inventors: Gennaro Ciliberto, Rome (IT); Paolo Antonio Ascierto, Naples (IT); Luigi Fattore, Naples (IT); Gerardo Botti, Naples (IT); Rita Mancini, Rome (IT)

(73) Assignees: ISTITUTI FISIOTERAPICI OSPITALIERI, Rome (IT); ISTITUTO NAZIONALE TUMORI I.R.C.C.S. "FONDAZIONE G. PASCALE", Naples (IT); UNIVERSITA' DEGLI STUDI DI ROMA "LA SAPIENZA", Rome (IT)

( * ) Notice: Subject to any disclaimer, the term of this patent is extended or adjusted under 35 U.S.C. 154(b) by 0 days.

(21) Appl. No.: 17/046,478

(22) PCT Filed: Apr. 10, 2019

(86) PCT No.: PCT/IT2019/050073
§ 371 (c)(1),
(2) Date: Oct. 9, 2020

(87) PCT Pub. No.: WO2019/198115
PCT Pub. Date: Oct. 17, 2019

(65) Prior Publication Data
US 2021/0147945 A1 May 20, 2021

(30) Foreign Application Priority Data
Apr. 11, 2018 (IT) .................. 102018000004384

(51) Int. Cl.
*C12Q 1/6886* (2018.01)
*C12N 15/113* (2010.01)
*A61K 45/06* (2006.01)

(52) U.S. Cl.
CPC .......... *C12Q 1/6886* (2013.01); *A61K 45/06* (2013.01); *C12N 15/113* (2013.01); *C12N 2310/141* (2013.01); *C12N 2310/3231* (2013.01); *C12N 2320/31* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2006/0134639 | A1* | 6/2006 | Huffel | C12Q 1/6837 435/6.14 |
| 2013/0197060 | A1* | 8/2013 | Markel | C12Q 1/6886 514/44 A |
| 2015/0297626 | A1* | 10/2015 | van Haastert | A61K 31/4184 514/44 A |
| 2017/0275703 | A1* | 9/2017 | Stark | C12Q 1/6813 |

FOREIGN PATENT DOCUMENTS

| WO | WO 2011/106104 A2 | 9/2011 |
| WO | WO 2014/143855 A2 | 9/2014 |

OTHER PUBLICATIONS

Diaz-Martinez et al. Cancer Res. 78: 1017-1030 (Year: 2017).*
Motti et al. International Journal of Molecular Sciences 21, 4544, pp. 1-15 (Year: 2020).*
International Search Report in PCT/IT2019/050073, dated Sep. 30, 2019.
Fattore, Luigi, et al., "MicroRNAs in melanoma development and resistance to target therapy", Oncotarget, vol. 8, No. 13, Mar. 28, 2017 pp. 22262-22278.
Fattore, Luigi, et al., "miR-579-3p controls melanoma progression and resistance to target therapy", Proceedings of the National Academy of Sciences, vol. 113, No. 34; E5005-E5013, Aug. 23, 2016.
Fattore, Luigi, et al., "MicroRNA-driven deregulation of cytokine expression helps development of drug resistance in metastatic melanoma", Cytokine and Growth Factor Reviews, vol. 36, May 17, 2017, pp. 39-48.
Kozar Ines, et al., "Impact of BRAF kinase inhibitors on the miRNomes and transcriptomes of melanoma cells", Biochimica et Biophysica Acta (BBA)—General Subjects, vol. 1861, No. 11, Apr. 10, 2017, pp. 2980-2992.
Italian Search Report in Italian application No. IT 201800004384, dated Aug. 16, 2018.
Asciero, Paolo A., et al., "The role of BRAF V600 mutation in melanoma," Journal of Translational Medicine (2012), 10; 85 (in 9 pages).
Balatti, Veronica, et al., "tsRNA signatures in cancer," PNAS, Jul. 25, 2017, vol. 114, No. 30, 8071-8076.
Bora, Roop Singh, et al., RNA interference therapeutics for cancer: Challenges and opportunities (Review), Molecular Medicine Reports, 6: 9-15 (2012).
Campani, Virginia, et al., "Lipid Nanoparticles to Deliver miRNA in Cancer," Current Pharmaceutical Biotechnology, 2016, 17, 741-749.

(Continued)

*Primary Examiner* — Brian Whiteman
(74) *Attorney, Agent, or Firm* — Knobbe, Martens, Olson & Bear, LLP

(57) ABSTRACT miRNAs for in vitro diagnosis of resistance of tumors to BRAF/MEK pathway (also named as MAPK 5 pathway) inhibiting drugs and for treatment of tumors which are treated with said drugs, such as melanoma, by stimulating or inhibiting the expression of down-regulated or up-regulated miRNAs, respectively.

6 Claims, 32 Drawing Sheets

Figure 1:
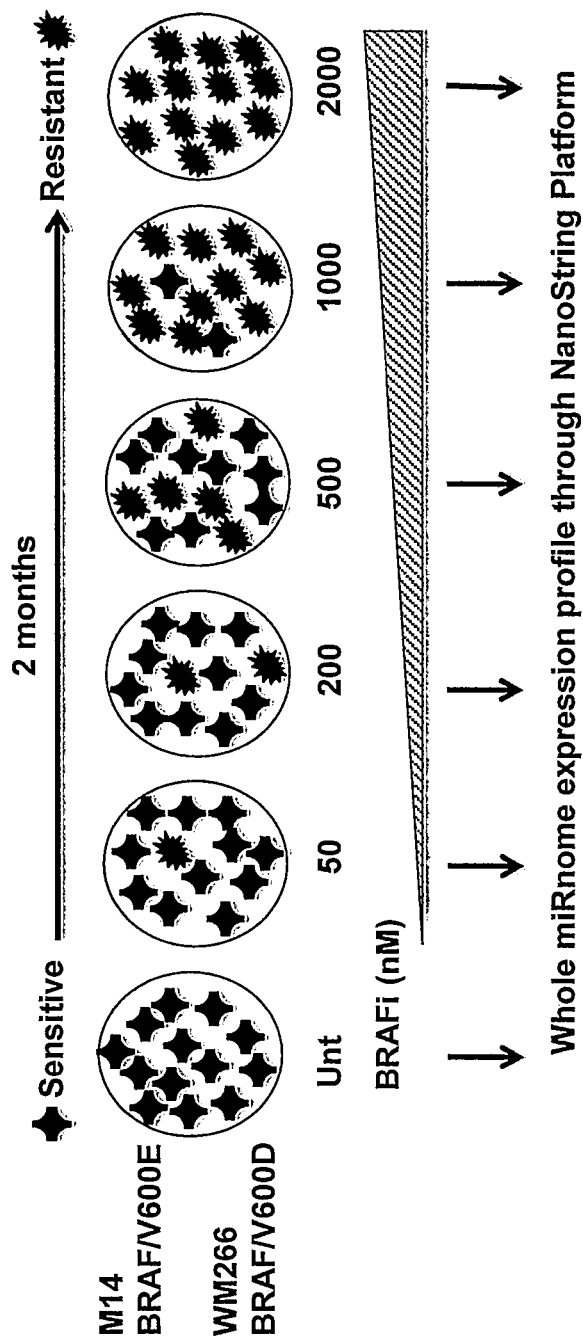

Specification includes a Sequence Listing.

(56) References Cited

OTHER PUBLICATIONS

Di Costanzo, Ezio, et al., A Macroscopic Mathematical Model for Cell Migration Assays Using a Real-Time Cell Analysis, PLOS One, Sep. 28, 2016, (in 20 pages).

Dai, Lan, et al., "MiR-199a inhibits the angiogenic potential of endometrial stromal cells under hypoxia by targeting HIF-1α/VEGF pathway," Int J Clin Exp Pathol 2015; 8(5):4735-4744.

Di Martino, Maria Teresa, et al., "In Vivo Activity of MiR-34a Mimics Delivered by Stable Nucleic Acid Lipid Particles (SNALPs) against Multiple Myeloma," PLOS One, Feb. 14, vol. 9, Issue 2 (in 10 pages), 2014.

Fattore, Luigi, et al., "miR-579-3p controls melanoma progression and resistance to target therapy," PNAS, Aug. 8, 2016; E5005-E5013.

Fattore, Luigi, et al., "Reprogramming of miRNAs global expression orchestrates development of drug resistance in BRAF mutated melanoma," Cell Death & Differentiation (2019) 26: 1267-1282.

Fattore, Luigi, et al., "In Vitro Biophysical and Biological Characterization of Lipid Nanoparticles Co-Encapsulating Oncosuppressors miR-199b-5p and miR-204-5p as Potentiators of Target Therapy in Metastatic Melanoma," Int. J. Mol. Sci. 2020, 21, 1930 (in 14 pages).

Fogli, Stefano, et al., "Identification of plasma microRNAs as new potential biomarkers with high diagnostic power in human cutaneous melanoma," Tumor Biology, May 2017: 1-8.

Franklin, C., et al., "Immunotherapy in melanoma: Recent advances and future directions," EJSO 43 (2017) 604-611.

Jones, Valerie Sloane, et al., "Cytokines in cancer drug resistance: Cues to new therapeutic strategies," Biochimica et Biophysica Acta 1865 (2016) 255-265.

Kozar, Ines, et al., "Impact of BRAF kinase inhibitors on the miRNomes and transcriptomes of melanoma cells," BBA—General Subjects 1861 (2017) 2980-2992.

Ma, Zhihai, et al., "Profiling and Discovery of Novel miRNAs from Formalin-Fixed, Paraffin-Embedded Melanoma and Nodal Specimens," Journal of Molecular Diagnostics, vol. 11, No. 5, Sep. 2009, pp. 420-429.

Mansoori, Behzad, et al., "RNA Interference and its Role in Cancer Therapy," Adv Pharm Bull, 2014, 4(4), 313-321.

Menzies, Alexander and Long, Georgina V., "Systemic treatment for BRAF-mutant melanoma: where do we go next?" Lancet Oncol (2014): 15: e371-e381.

Moriceau, Gatien, et al., "Tunable-Combinatorial Mechanisms of Acquired Resistance Limit the Efficacy of BRAF/MEK Cotargeting but Result in Melanoma Drug Addiction," Cancer Cell 27, 240-256 (2015).

Mumford, Sophie L., et al., "Circulating MicroRNA Biomarkers in Melanoma: Tools and Challenges in Personalised Medicine," Biomolecules (2018), 8, 21 (in 25 pages).

Rajabi, Parvin, et al., "The role of VEGF in melanoma progression," Journal of Research in Medical Sciences, Jun. 2012; 17: 534-9.

Robert, Carolina, M.C., Ph.D., et al., "Improved Overall Survival in Melanoma with Combined Dadrafenib and Trametinib," N Engl J Med (2015); 372;30-39.

Roesch, A., "Tumor heterogeneity and plasticity as elusive drivers for resistance to MAPK pathway inhibition in melanoma," Oncogene (2015) 34, 2951-2957.

Schwarzenbach, Heidi, et al., "Clinical relevance of circulating cell-free microRNAs in cancer," Nat. Rev. Clin. Oncol. 11, 145-156 (2014).

Semple, Sean C., et al., "Efficient encapsulation of antisense oligonucleotides in lipid vesicles using ionizable aminolipids: formation of novel small multilamellar vesicle structures," Biochimica et Biophysica Acta 1510 (2001) 152-166.

Sharma, P.S., et al., "VEGF/VEGFR Pathway Inhibitors as Anti-Angiogenic Agents: Present and Future," Current Cancer Drug Targets, 2011, 11, 624-653.

Wittrup, Anders and Lieberman, Judy, "Knocking down disease: a progress report on siRNA therapeutics," Nat Rev Genet. Sep. 2015: 16(9): 543-552.

Zhang, Gao, et al., "Targeting mitochondrial biogenesis to overcome drug resistance to MAPK inhibitors," The Journal of Clinical Investigation, vol. 126, No. 5, May 2016, 1834-1856.

\* cited by examiner

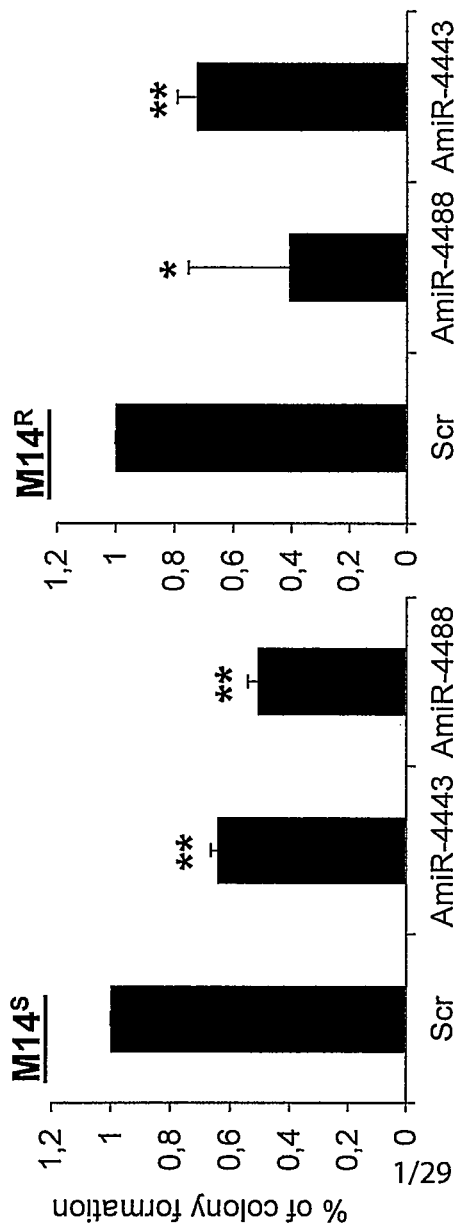
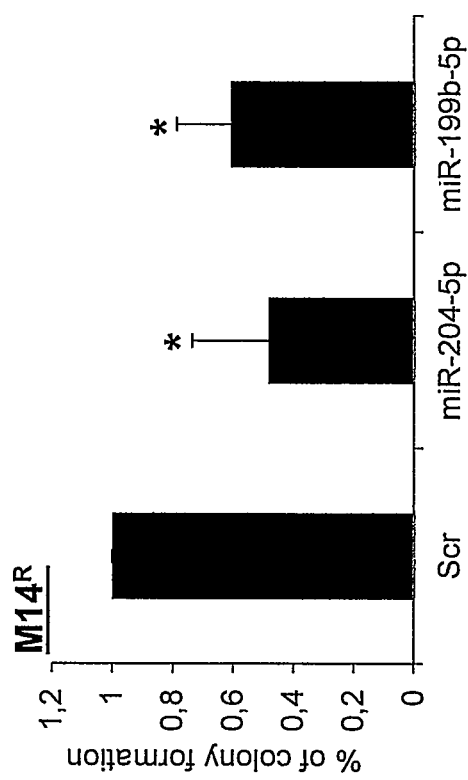
Fig. 14
Fig. 15

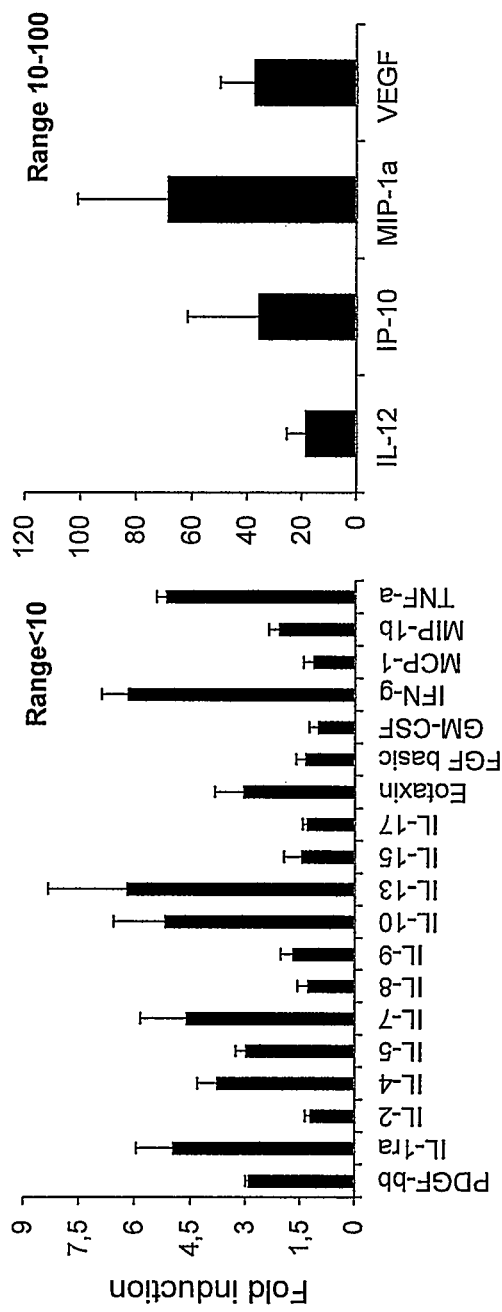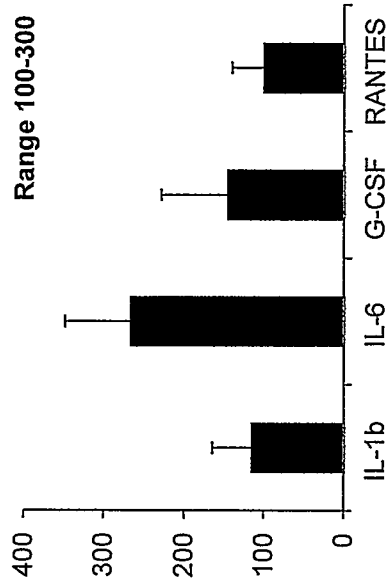
Fig. 22

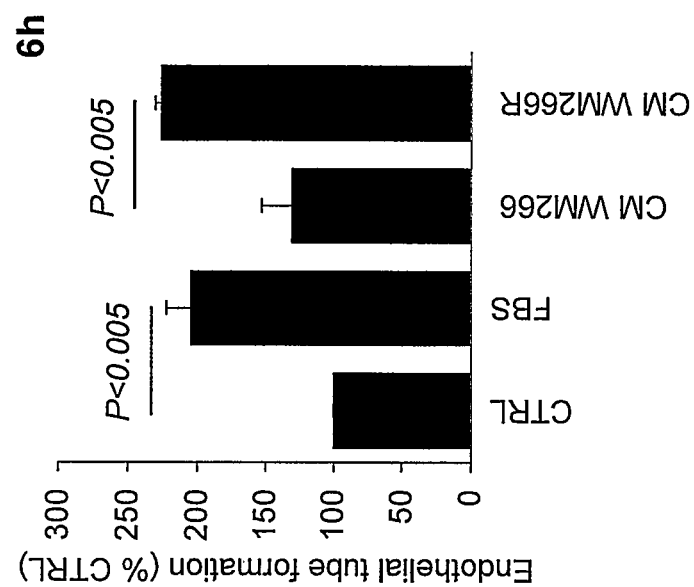
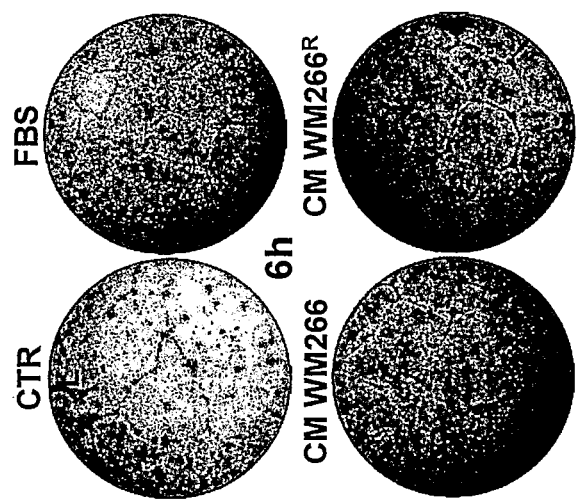
Fig. 24

SEQUENCE LISTING

```
<160> NUMBER OF SEQ ID NOS: 25

<210> SEQ ID NO 1
<211> LENGTH: 23
<212> TYPE: RNA
<213> ORGANISM: Homo sapiens

<400> SEQUENCE: 1
cccaguguuu agacuaucug uuc                                              23

<210> SEQ ID NO 2
<211> LENGTH: 22
<212> TYPE: RNA
<213> ORGANISM: Homo sapiens

<400> SEQUENCE: 2
uucccuuugu cauccuaugc cu                                               22

<210> SEQ ID NO 3
<211> LENGTH: 23
<212> TYPE: RNA
<213> ORGANISM: Homo sapiens

<400> SEQUENCE: 3
guccaguuuu cccaggaauc ccu                                              23

<210> SEQ ID NO 4
<211> LENGTH: 23
<212> TYPE: RNA
<213> ORGANISM: Homo sapiens

<400> SEQUENCE: 4
uaaggugcau cuagugcaga uag                                              23

<210> SEQ ID NO 5
<211> LENGTH: 21
<212> TYPE: RNA
<213> ORGANISM: Homo sapiens

<400> SEQUENCE: 5
gcaguccaug ggcauauaca c                                                21

<210> SEQ ID NO 6
<211> LENGTH: 23
<212> TYPE: RNA
<213> ORGANISM: Homo sapiens

<400> SEQUENCE: 6
```
agcagcauug uacagggcua uca  23

<210> SEQ ID NO 7
<211> LENGTH: 22
<212> TYPE: RNA
<213> ORGANISM: Homo sapiens

<400> SEQUENCE: 7
uagcagcaca ucaugguuua ca  22

<210> SEQ ID NO 8
<211> LENGTH: 23
<212> TYPE: RNA
<213> ORGANISM: Homo sapiens

<400> SEQUENCE: 8
agcuacauug ucugcugggu uuc  23

<210> SEQ ID NO 9
<211> LENGTH: 21
<212> TYPE: RNA
<213> ORGANISM: Homo sapiens

<400> SEQUENCE: 9
gcgacccaua cuugguuuca g  21

<210> SEQ ID NO 10
<211> LENGTH: 17
<212> TYPE: RNA
<213> ORGANISM: Homo sapiens

<400> SEQUENCE: 10
uuggaggcgu ggguuuu  17

<210> SEQ ID NO 11
<211> LENGTH: 18
<212> TYPE: RNA
<213> ORGANISM: Homo sapiens

<400> SEQUENCE: 11 aggggggcggg cuccggcg  18

<210> SEQ ID NO 12
<211> LENGTH: 22
<212> TYPE: RNA
<213> ORGANISM: Homo sapiens

<400> SEQUENCE: 12
ucggccugac cacccacccc ac  22

<210> SEQ ID NO 13
<211> LENGTH: 23
<212> TYPE: RNA
<213> ORGANISM: Homo sapiens

<400> SEQUENCE: 13
ucuuugguua ucuagcugua uga  23

<210> SEQ ID NO 14
<211> LENGTH: 22
<212> TYPE: RNA
<213> ORGANISM: Homo sapiens -continued

<400> SEQUENCE: 14
accuugccuu gcugcccggg cc                                        22

<210> SEQ ID NO 15
<211> LENGTH: 17
<212> TYPE: RNA
<213> ORGANISM: Homo sapiens

<400> SEQUENCE: 15
accccacucc ugguacc                                              17

<210> SEQ ID NO 16
<211> LENGTH: 19
<212> TYPE: RNA
<213> ORGANISM: Homo sapiens

<400> SEQUENCE: 16
gagccaguug gacaggagc                                            19

<210> SEQ ID NO 17
<211> LENGTH: 22
<212> TYPE: RNA
<213> ORGANISM: Homo sapiens

<400> SEQUENCE: 17
aguauucugu accagggaag gu                                        22

<210> SEQ ID NO 18
<211> LENGTH: 17
<212> TYPE: DNA
<213> ORGANISM: Artificial Sequence
<220> FEATURE:
<223> OTHER INFORMATION: antimiR-4443

<400> SEQUENCE: 18
aaaacccacg cctccaa                                              17

<210> SEQ ID NO 19
<211> LENGTH: 18
<212> TYPE: DNA
<213> ORGANISM: Artificial Sequence
<220> FEATURE:
<223> OTHER INFORMATION: antimiR-4488

<400> SEQUENCE: 19
cgccggagcc cgcccct                                              18

<210> SEQ ID NO 20
<211> LENGTH: 22
<212> TYPE: DNA
<213> ORGANISM: Artificial Sequence
<220> FEATURE:
<223> OTHER INFORMATION: antimiR-1234

<400> SEQUENCE: 20
gtggggtggg tggtcaggcc ga                                        22

<210> SEQ ID NO 21
<211> LENGTH: 23
<212> TYPE: DNA
<213> ORGANISM: Artificial Sequence
<220> FEATURE:
<223> OTHER INFORMATION: antimiR-9-5p

<400> SEQUENCE: 21

```
tcatacagct agataaccaa aga                                          23

<210> SEQ ID NO 22
<211> LENGTH: 22
<212> TYPE: DNA
<213> ORGANISM: Artificial Sequence
<220> FEATURE:
<223> OTHER INFORMATION: antimiR-1915-5p

<400> SEQUENCE: 22
ggcccgggca gcaaggcaag gt                                           22

<210> SEQ ID NO 23
<211> LENGTH: 17
<212> TYPE: DNA
<213> ORGANISM: Artificial Sequence
<220> FEATURE:
<223> OTHER INFORMATION: antimiR-4286

<400> SEQUENCE: 23
ggtaccagga gtggggt                                                 17

<210> SEQ ID NO 24
<211> LENGTH: 19
<212> TYPE: DNA
<213> ORGANISM: Artificial Sequence
<220> FEATURE:
<223> OTHER INFORMATION: antimiR-575

<400> SEQUENCE: 24
gctcctgtcc aactggctc                                               19

<210> SEQ ID NO 25
<211> LENGTH: 22
<212> TYPE: DNA
<213> ORGANISM: Artificial Sequence
<220> FEATURE:
<223> OTHER INFORMATION: antimiR-630

<400> SEQUENCE: 25
accttccctg gtacagaata ct                                           22
```

MIRNAS FOR TREATMENT AND IN VITRO DIAGNOSIS OF DRUG RESISTANT TUMORS

FIELD

The present invention concerns miRNAs for treatment and in vitro diagnosis of drug resistant tumors. In particular, the present invention concerns miRNAs for in vitro diagnosis of resistance of tumors to BRAF/MEK pathway (also named as MAPK pathway) inhibiting drugs and for treatment of tumors which are treated with said drugs, such as melanoma, by stimulating or inhibiting the expression of down-regulated or up-regulated miRNAs, respectively.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 33667855_1.txt, the date of creation of the ASCII text file is Oct. 9, 2020, and the size of the ASCII text file is 4.46 KB.

BACKGROUND

The natural history of metastatic melanoma has recently changed thanks to the development of novel immunotherapy and targeted therapy approaches, which have significantly improved patients' survival (1). The first type of these therapies is based on immune checkpoint inhibitors targeting CTLA4 and PD1/PDL1 interaction which have entered in the routine clinical practice and on other immune-modulators which are currently in advanced clinical trials (2). The second type is principally represented by small targeting inhibitors of kinases (KIs) of the MAPK pathway which were developed following the initial discovery that BRAF V600 mutations are among the major oncogenic drivers of melanoma proliferation and survival (1,3). Indeed, near 50% of patients harbor v-raf murine sarcoma viral oncogene homolog B1 (BRAF) V600 mutations, which is responsible for the uncontrolled activation of the mitogen-activated protein kinase (MAPK) signaling pathway (3).

This evidence led to the clinical development of BRAF inhibitors, firstly used as mono-therapies and more recently in combination with MEK inhibitors following the discovery that BRAFi resistance is frequently characterized by the reactivation of the MAPK signaling and the involvement of the MEK kinase (4). However, drug resistance virtually frustrates both mono-therapies with BRAF inhibitors and dual-therapies with combinations of a BRAF inhibitor plus a MEK inhibitor.

The majority of BRAF-mutated melanoma patients initially respond to KIs, until the development of de novo drug resistance, which creates an intractable clinical condition, especially in the cases of BRAF and MEK inhibitors acquired resistance (5). Furthermore, approximately 10% to 15% of melanoma patients harboring BRAF-mutations do not initially respond to first line targeted therapies, and even 40% to 50% of patients show only partial responses (6). These evidences strongly suggest that both ab initio and acquired resistance are a major hurdle to achieve durable control of metastatic disease.

A challenging issue is, therefore, in the field of melanoma, to generate powerful diagnostics capable to predict patients' response to therapies and to conceive combination therapies capable to block or revert development of drug resistance.

During last years, several studies directed to understand the molecular basis of resistance to KIs have identified both genetic and non-genetic (or otherwise called) phenotypic mechanisms (7).

Interestingly, the same genetic alterations have been identified both in BRAFi mono-therapy resistance as well as in combinations of BRAF inhibitors with MEK inhibitors. In most cases these secondary genetic alterations cause reactivation of MAPK signaling (5).

In contrast, non genetic/phenotypic mechanisms are linked to the activation of a highly heterogeneous and dynamic set of adaptive responses fueled by tumor cell plasticity (7). These adaptive responses involve a variety of redundant and often interchangeable intracellular pathways which contribute to cell resistance to cell death in the presence of MAPK signaling inhibitors. Blockade of a single pathway is in most cases insufficient to fully counteract these adaptive mechanisms because of the activation of bypass pathways. Therefore, there is the need of an alternative approach.

A novel miR-579-3p as a regulator of melanoma development and drug resistance (8) has been recently discovered. This miRNA is down-regulated in BRAF-mutated melanomas and correlated to worse patients' prognosis. In addition, miR-579-3p relevant target genes have been identified: the oncogenic BRAF itself and the MDM2 oncoprotein (8). These evidences strongly explain its oncosuppressive role in metastatic melanomas bearing BRAF V600 mutations. Most importantly, miR-579-3p is able to impair the development of resistance to MAPK inhibitors in vitro and its deregulation was confirmed in patients who developed resistance to targeted therapies in contrast to its target genes, which are up-regulated (8).

However, the great heterogeneity of human melanoma samples makes this single miRNA per se not suitable for providing an effective in vitro diagnosis of drug resistance.

Further to the evidence that individual miRNAs can affect sensitivity to target therapies in melanoma, it is also known a study concerning a comprehensive analysis of the changes affecting the entire miRNome during the development of drug resistance to MAPK inhibitors (9). This study identifies specific miRNAs from specific cell lines as possible factors responsible for drug resistance to BRAF kinase inhibitors. However, it does not provide any experimental data in order to validate the diagnostic and/or therapeutic function of these miRNAs, and in particular of combination of miRNAs as diagnostics or therapeutics.

In the light of the above, it is therefore apparent the need to provide methods for in vitro diagnosis of tumors which are resistant to BRAF/MEK pathway BRAF-mutated melanoma patients and of their resistance to inhibiting drugs, and for treating said resistance.

SUMMARY

According to the present invention, a population of miRNAs which is deregulated during the development of drug resistance has been identified by a large study of the entire miRNAome in vitro. Briefly, through the analysis of changes in the expression of the whole miRnome of BRAF-mutated melanoma cells before and after the establishment of resistance to a BRAFi, a set of several deregulated miRNAs, which have been divided in miRNAs facilitators or antagonists of drug resistance, has been identified. Several data were obtained mostly pointing out to the therapeutic and diagnostic features of these miRNA and were later reported in detail also in Fattore et al (10).

Interestingly, a set of intracellular pathways affected by these miRNAs with a prominent involvement of pro-inflammatory and pro-angiogenetic genes was also identified through bioinformatic and experimental approaches.

All together, these data show that miRNA deregulation in concert with cytokine aberrant expression is responsible for the establishment of resistance to targeted therapies in metastatic melanoma.

In particular, it has been found that miR-4443 and miR-4488 are up-regulated, wherein miR-204-5p and miR-199b-5p are down-regulated in BRAF-mutated melanoma patients, i.e. in patients who show resistance to BRAF/MEK pathway inhibiting drugs.

As for the diagnostic application, liquid biopsy of circulating nucleic acids is a highly sensitive and specific non-invasive diagnostic modality to monitor disease burden and to define biomarkers predictive of drug response or resistance. MicroRNAs (miRs) are ideal biomarkers since they are actively released by tumor cells and cells of the tumor microenvironment, and can be easily detected in the circulation (11). In this context, the above mentioned two BRAFi-resistant up-regulated miRs (miR-4443 and miR-4488) and two downregulated (miR-199b-5p and miR-204-5p;) were further tracked in plasma samples derived from BRAF mutated melanoma patients before initiation of target therapy and at Disease Progression (PD). It has been observed that miRs deregulation is associated with therapeutic resistance with significant AUC predictive values.

The experiments reported below show that the above mentioned miRNAs are suitable as markers of resistance to BRAF/MEK pathway inhibiting drugs with high sensitivity, specificity and accuracy.

As for the therapeutic application, the experiments reported below show that the inhibition of the expression of the up-regulated miRNAs or the stimulation of the expression of the down-regulated miRNAs is effective in reducing drug resistance.

Cancer is one of the main applications of potential miRNA-based therapies (12). Importantly, since a single miRNA is capable to bind simultaneously several different mRNAs, the use of miRNAs offers the possibility to target simultaneously multiple pathways involved in tumor development and progression, providing the opportunity to develop new powerful drugs for the therapy of cancer (13). However, the use of miRNA-based drugs is hampered by the rapid degradation by nucleases and the poor and unspecific cellular uptake (14). Nanotechnology can overcome these biopharmaceutical issues, because of its potential to preserve RNA stability and to enhance intracellular uptake. In detail, stable nucleic acid lipid particles (SNALPs) have been previously developed to deliver miRNAs in an experimental model of multiple myeloma (15). These carriers, previously proposed by Semple et al. (16) are characterized by a high RNA encapsulation, stability in presence of serum, ability to protect miRNA against enzymatic degradation and ability to increase oligonucleotide uptake into the target cells.

It is therefore specific object of the present invention a method for in vitro diagnosis of resistance to MAPK pathway (or more specifically BRAF/MEK pathway) inhibiting drugs in tumors, said method comprising measuring the expression, in a biological sample, of at least two, three or all of the following microRNAs:

miR-199b-5p:
(SEQ ID NO: 1)
cccaguguuuagacuaucuguuc, miR-204-5p:
(SEQ ID NO: 2)
uucccuuugucauccuaugccu, miR-4443:
(SEQ ID NO: 10)
uuggaggcgugguuuu, miR-4488:
(SEQ ID NO: 11)
aggggcgggcuccggcg, wherein miR-199b-5p and miR-204-5p are down-expressed in the resistance to MAPK pathway (or more specifically BRAF/MEK pathway) inhibiting drugs, whereas miR-4443, miR-4488 are over-expressed in the resistance to MAPK pathway (or more specifically BRAF/MEK pathway) inhibiting drugs in comparison with their expression in controls which do not present said resistance.

According to the present invention the tumors are those which are BRAF mutated tumors and are treated with MAPK pathway (or more specifically BRAF/MEK pathway) inhibiting drugs. For example, the tumors that can be resistant according to the present invention are melanoma, Colorectal cancer, papillary thyroid carcinoma, non small cell lung cancer, brain tumors, non-Hodgkin lymphoma. Specifically, the above-mentioned tumors are those which are BRAF mutated.

According to an embodiment of the present invention, the method can comprise measuring the expression of the following combinations of miRNAs listed from the most preferred: miR-199b-5p and miR-4488; miR-199b-5p and miR-4443; miR-4488 and miR-4443; miR-199b-5p, miR-4443 and miR-4488; miR-199b-5p and miR-204-5p.

In addition, the method according to the present invention can further comprise measuring the expression of at least one of the following miRNAs:

miR-145-5p:
(SEQ ID NO: 3)
guccaguuuucccaggaaucccu, miR-18a-5p:
(SEQ ID NO: 4)
uaaggugcaucuagugcagauag, miR-455-3p:
(SEQ ID NO: 5)
gcaguccaugggcauauacac, miR-107:
(SEQ ID NO: 6)
agcagcauuguacagggcuauca, miR-15b-5p:
(SEQ ID NO: 7)
uagcagcacaucaugguuuaca, miR-221-3p:
(SEQ ID NO: 8)
agcuacauugucugcuggguuuc, miR-551b-3p:
(SEQ ID NO: 9)
gcgacccauacuuggguuucag, miR-1234:
(SEQ ID NO: 12)
ucggccugaccacccaccccac, -continued miR-9-5p:
(SEQ ID NO: 13)
ucuuugguuaucuagcuguauga, miR-1915-5p:
(SEQ ID NO: 14)
accuugccuugcugcccgggcc, miR-4286:
(SEQ ID NO: 15)
accccacuccugguacc, miR-575:
(SEQ ID NO: 16)
gagccaguuggacaggagc, miR-630:
(SEQ ID NO: 17)
aguauucuguaccagggaaggu, wherein miR-145-5p, miR-18a-5p, miR-455-3p, miR-107, miR-15b-5p, miR-221-3p, miR-551b-3p are down-expressed in the resistance to MAPK pathway (or more specifically BRAF/MEK pathway) inhibiting drugs, whereas miR-1234, miR-9-5p, miR-1915-5p, miR-4286, miR-575, miR-630 are over-expressed in the resistance to MAPK pathway (or more specifically BRAF/MEK pathway) inhibiting drugs in comparison with their expression in controls which do not present said resistance.

The biological sample can be a liquid biological sample such as blood, serum, plasma, urine.

The method according to the present invention can be carried out for example by Real Time PCR, Droplet Digital PCR, Microarray, RNA Hybridization Methods such as Northern Blot or Dot Blot, RNA Next Generation Sequencing.

The present invention concerns also the use of at least two, three or all of the following microRNAs:

miR-199b-5p:
(SEQ ID NO: 1)
cccaguguuuagacuaucuguuc, miR-204-5p:
(SEQ ID NO: 2)
uucccuuugucauccuaugccu, miR-4443:
(SEQ ID NO: 10)
uuggaggcgugggguuuu, miR-4488:
(SEQ ID NO: 11)
aggggggcgggcuccggcg, as biomarkers for the in vitro diagnosis of the resistance of tumors to MAPK pathway (or more specifically BRAF/MEK pathway) inhibiting drugs, wherein miR-199b-5p and miR-204-5p are down-expressed in the resistance to MAPK pathway (or more specifically BRAF/MEK pathway) inhibiting drugs, whereas miR-4443, miR-4488 are over-expressed. As mentioned above the tumors which are resistant to the drugs are those which are BRAF mutated tumors and are treated with MAPK pathway (or more specifically BRAF/MEK pathway) inhibiting drugs. For example, the tumors are chosen from the group consisting of melanoma, Colorectal cancer, papillary thyroid carcinoma, non small cell lung cancer, brain tumors, non-Hodgkin lymphoma. Specifically, the above-mentioned tumors are those which are BRAF mutated.

According to an embodiment of the present invention, said two or three of the microRNAs can be the following combinations of miRNAs listed from the most preferred: miR-199b-5p and miR-4488; miR-199b-5p and miR-4443; miR-4488 and miR-4443; miR-199b-5p, miR-4443 and miR-4488; miR-199b-5p and miR-204-5p.

In addition, the use according to the present invention can further comprise the use of at least one of the following miRNAs as biomarkers for the in vitro diagnosis of the resistance to MAPK pathway (or more specifically BRAF/MEK pathway) inhibiting drugs:

miR-145-5p:
(SEQ ID NO: 3)
guccaguuuucccaggaaucccu, miR-18a-5p:
(SEQ ID NO: 4)
uaaggugcaucuagugcagauag, miR-455-3p:
(SEQ ID NO: 5)
gcaguccaugggcauauacac, miR-107:
(SEQ ID NO: 6)
agcagcauuguacagggcuauca, miR-15b-5p:
(SEQ ID NO: 7)
uagcagcacaucaugguuuaca, miR-221-3p:
(SEQ ID NO: 8)
agcuacauugucugcugggguuuc, miR-551b-3p:
(SEQ ID NO: 9)
gcgacccauacuuggguuucag, miR-1234:
(SEQ ID NO: 12)
ucggccugaccacccacccac, miR-9-5p:
(SEQ ID NO: 13)
ucuuugguuaucuagcuguauga, miR-1915-5p:
(SEQ ID NO: 14)
accuugccuugcugcccgggcc, miR-4286:
(SEQ ID NO: 15)
accccacuccugguacc, miR-575:
(SEQ ID NO: 16)
gagccaguuggacaggagc, miR-630:
(SEQ ID NO: 17)
aguauucuguaccagggaaggu, wherein miR-145-5p, miR-18a-5p, miR-455-3p, miR-107, miR-15b-5p, miR-221-3p, miR-551b-3p are down-expressed in the resistance to MAPK pathway (or more specifically BRAF/MEK pathway) inhibiting drugs, whereas miR-1234, miR-9-5p, miR-1915-5p, miR-4286, miR-575, miR-630 are over-expressed in the resistance to MAPK pathway (or more specifically BRAF/MEK pathway) inhibiting drugs in comparison with their expression in controls which do not present said resistance.

A further object of the present invention is an antagonist of at least one of miR-4443 and miR-4488 and/or a miRNA mimic of at least one of miR-199b-5p and miR-204-5p for use in the treatment of tumors which are resistant to MAPK pathway (or more specifically BRAF/MEK pathway) inhibiting drugs, wherein said antagonist is chosen from the group consisting of Locked Nucleic Acid (LNA) targeting miR-4443, Locked Nucleic Acid (LNA) targeting miR-4488, antimiR-4443: aaaacccacgcctccaa (SEQ ID NO:18), anti-miR-4488: cgccggagcccgcccct (SEQ ID NO:19), whereas said miRNA mimic is chosen from the group consisting of miR-199b-5p mimic: cccaguguuuagacuaucuguuc (SEQ ID NO:1), miR-204-5p mimic: uucccuuugucauccuaugccu (SEQ ID NO:2). As mentioned above the tumors are those which are BRAF mutated tumors and are treated with MAPK pathway (or more specifically BRAF/MEK pathway) inhibiting drugs.

Antagonists and miRNA mimics, preferably miRNA mimics, according to the present invention can be administered and delivered by lipid nanoparticles since the use of naked RNA-based molecules in therapy is hampered by their rapid enzymatic degradation in biological fluids and poor efficiency in crossing cell membranes. For example antagonists and miRNA mimics according to the present invention can be administered and delivered by stable nucleic acid lipid particles (SNALPs). The route of administration can be intravenous administration (17).

According to the present invention, when a mixture of said antagonist and/or miRNA mimic is used (i.e. a mixture of more than one antagonist or a mixture of more than one miRNA mimic or a mixture of one or more antagonists with one or more miRNA mimics is used), said mixture can be: miR-199b-5p, miR-204-5p and miR-579-3p; miR-199b-5p and miR-204-5p; antimiR-4443 or LNA targeting miR-4443 and antimiR-4488 or LNA targeting miR-4488; antimiR-4488 or LNA targeting miR-4488 and miR-204-5p; antimiR-4443 or LNA targeting miR-4443 and miR-204-5p; miR-199b-5p and antimiR-4443 or LNA targeting miR-4443; miR-199b-5p and antimiR-4488 or LNA targeting miR-4488, wherein the mixtures are listed from the most preferable.

In addition, said antagonist and/or miRNA mimic can be in combination with at least one of the following antagonists and/or miRNA mimic:

```
antimiR-1234:
                                    (SEQ ID NO: 20)
gtggggtgggtggtcaggccga
or LNA targeting miR-1234, antimiR-9-5p:
                                    (SEQ ID NO: 21)
tcatacagctagataaccaaaga
or LNA targeting miR-9-5p, antimiR-1915-5p:
                                    (SEQ ID NO: 22)
ggcccgggcagcaaggcaaggt
or LNA targeting miR-1915-5p, antimiR-4286:
                                    (SEQ ID NO: 23)
ggtaccaggagtggggt
or LNA targeting miR-4286, antimiR-575:
                                    (SEQ. ID. NO. 24)
gctcctgtccaactggctc
or LNA targeting miR-575, antimiR-630:
                                    (SEQ ID NO: 25)
accttccctggtacagaatact
or
```

```
-continued
LNA targeting miR-630, miR145-5p mimic:
                                    (SEQ ID NO: 3)
guccaguuuucccaggaaucccu, miR-18a-5p mimic:
                                    (SEQ ID NO: 4)
uaaggugcaucuagugcagauag, miR-455-3p mimic:
                                    (SEQ ID NO: 5)
gcaguccaugggcauauacac, miR-107 mimic:
                                    (SEQ ID NO: 6)
agcagcauuguacagggcuauca, miR-15b-5p mimic:
                                    (SEQ ID NO: 7)
uagcagcacaucaugguuuaca, miR-221-3p mimic:
                                    (SEQ ID NO: 8)
agcuacauugucugcugggauuc, miR-551b-3p mimic:
                                    (SEQ ID NO: 9)
gcgacccauacuuggauucag.
```

The present invention concerns also a combination of an antagonist of at least one of miR-4443 and miR-4488 and/or of a miRNA mimic of at least one of miR-199b-5p and miR-204-5p with at least one MAPK pathway (or more specifically BRAF/MEK pathway) inhibiting drug for the simultaneous, sequential or separate use in the treatment of tumors which are resistant to MAPK pathway (or more specifically BRAF/MEK pathway) inhibiting drugs, wherein said antagonist is chosen from the group consisting of Locked Nucleic Acid (LNA) targeting miR-4443, Locked Nucleic Acid (LNA) targeting miR-4488, antimiR-4443: aaaacccacgcctccaa (SEQ ID NO:18), antimiR-4488: cgccggagcccgcccct (SEQ ID NO:19), whereas said miRNA mimic is chosen from the group consisting of miR-199b-5p mimic: cccaguguuuagacuaucuguuc (SEQ ID NO:1), miR-204-5p mimic: uucccuuugucauccuaugccu (SEQ ID NO:2), wherein said antagonist and/or miRNA mimic is used against the resistance to MAPK pathway (or more specifically BRAF/MEK pathway) inhibiting drugs.

According to the present invention, the MAPK pathway (or more specifically BRAF/MEK pathway) inhibiting drugs can be for example vemurafenib, Trametinib(GSK1120212), dabrafenib, sorafenib (a Raf kinase inhibitor), other Raf inhibitors such as SB590885, PLX4720, XL281, RAF265, encorafenib, MEK inhibitors such as cobimetinib, CI-1040, PD0325901, Binimetinib (MEK162), selumetinib.

The term "simultaneous use" according to the present invention is understood as meaning the administration of at least one MAPK pathway inhibiting drug (first component of the combination) and the antagonist and/or mimic of miRNAs of the present invention (second component of the combination) in a single and identical pharmaceutical form.

The term "separate use" is understood as meaning the administration, at the same time, of the above mentioned first and second component of the combination according to the invention in distinct pharmaceutical forms.

The term "sequential use" is understood as meaning the successive administration of the above mentioned first and second component or second and first component of the combination according to the invention, each in a distinct pharmaceutical form.

According to the combination of the present invention for the above mentioned use, when more than one of said antagonist and/or miRNA mimic is used (i.e. a mixture of more than one antagonist or a mixture of more than one miRNA mimic or a mixture of one or more antagonists with one or more miRNA mimics is used), the following mixtures of said antagonist and/or miRNA mimic can be used: miR-199b-5p, miR-204-5p and miR-579-3p; miR-199b-5p and miR-204-5p; antimiR-4443 or LNA targeting miR-4443 and antimiR-4488 or LNA targeting miR-4488; antimiR-4488 or LNA targeting miR-4488 and miR-204-5p; antimiR-4443 or LNA targeting miR-4443 and miR-204-5p; miR-199b-5p and antimiR-4443 or LNA targeting miR-4443; miR-199b-5p and antimiR-4488 or LNA targeting miR-4488, wherein the mixtures are listed from the most preferable.

In addition, the combination can further comprise at least one of the following antagonists and/or miRNA mimics:

```
antimiR-1234:
                                    (SEQ ID NO: 20)
gtggggtgggtggtcaggccga
or LNA targeting miR-1234, antimiR-9-5p:
                                    (SEQ ID NO: 21)
tcatacagctagataaccaaaga
or LNA targeting miR-9-5p, antimiR-1915-5p:
                                    (SEQ ID NO: 22)
ggcccgggcagcaaggcaaggt
or LNA targeting miR-1915-5p, antimiR-4286:
                                    (SEQ ID NO: 23)
ggtaccaggagtggggt
or LNA targeting miR-4286, antimiR-575:
                                    (SEQ. ID. NO. 24)
gctcctgtccaactggctc
or LNA targeting miR-575, antimiR-630:
                                    (SEQ ID NO: 25)
accttccctggtacagaatact
or LNA targeting miR-630, miR145-5p mimic:
                                    (SEQ ID NO: 3)
guccaguuuucccaggaaucccu, miR-18a-5p mimic:
                                    (SEQ ID NO: 4)
uaaggugcaucuagugcagauag, miR-455-3p mimic:
                                    (SEQ ID NO: 5)
gcaguccaugggcauauacac, miR-107 mimic:
                                    (SEQ ID NO: 6)
agcagcauuguacagggcuauca, miR-15b-5p mimic:
                                    (SEQ ID NO: 7)
uagcagcacaucaugguuuaca, miR-221-3p mimic:
                                    (SEQ ID NO: 8)
agcuacauugucugcuggguuuc, miR-551b-3p mimic:
                                    (SEQ ID NO: 9)
gcgacccauacuugguuucag.
```

The present invention concerns also a pharmaceutical composition comprising or consisting of antagonist of at least one of miR-4443 and miR-4488 and/or miRNA mimic of at least one of miR-199b-5p and miR-204-5p, in association with one or more excipients and/or adjuvants, said pharmaceutical composition being for use in the treatment of tumors which are resistant to MAPK pathway inhibiting drugs, wherein said antagonist is chosen from the group consisting of Locked Nucleic Acid targeting miR-4443, Locked Nucleic Acid targeting miR-4488, antimiR-4443: aaaacccacgcctccaa (SEQ ID NO:18), antimiR-4488: cgccggagcccgccccct (SEQ ID NO:19), whereas said miRNA mimic is chosen from the group consisting of miR-199b-5p mimic: cccaguguuuagacuaucuguuc (SEQ ID NO:1), miR-204-5p mimic: uucccuuugucauccuaugccu (SEQ ID NO:2).

According to an embodiment, when a mixture of said antagonist and/or miRNA mimic is used in the pharmaceutical composition, said mixture can be: miR-199b-5p, miR-204-5p and miR-579-3p; miR-199b-5p and miR-204-5p; antimiR-4443 or LNA targeting miR-4443 and antimiR-4488 or LNA targeting miR-4488; antimiR-4488 or LNA targeting miR-4488 and miR-204-5p; antimiR-4443 or LNA targeting miR-4443 and miR-204-5p; miR-199b-5p and antimiR-4443 or LNA targeting miR-4443; miR-199b-5p and antimiR-4488 or LNA targeting miR-4488.

According to a further embodiment of the present invention, said antagonist and/or miRNA mimic which is in the pharmaceutical composition can be in combination with at least one of the following antagonists and/or miRNA mimics:

```
antimiR-1234:
                                    (SEQ ID NO: 20)
gtggggtgggtggtcaggccga
or LNA targeting miR-1234, antimiR-9-5p:
                                    (SEQ ID NO: 21)
tcatacagctagataaccaaaga
or LNA targeting miR-9-5p, antimiR-1915-5p:
                                    (SEQ ID NO: 22)
ggcccgggcagcaaggcaaggt
or LNA targeting miR-1915-5p, antimiR-4286:
                                    (SEQ ID NO: 23)
ggtaccaggagtggggt
or LNA targeting miR-4286, antimiR-575:
                                    (SEQ. ID. NO. 24)
gctcctgtccaactggctc
or LNA targeting miR-575, antimiR-630:
                                    (SEQ ID NO: 25)
accttccctggtacagaatact
or LNA targeting miR-630, miR145-5p mimic:
                                    (SEQ ID NO: 3)
guccaguuuucccaggaaucccu, miR-18a-5p mimic:
                                    (SEQ ID NO: 4)
uaaggugcaucuagugcagauag, miR-455-3p mimic:
                                    (SEQ ID NO: 5)
gcaguccaugggcauauacac, miR-107 mimic:
                                    (SEQ ID NO: 6)
agcagcauuguacagggcuauca,
```

```
miR-15b-5p mimic:
                                    (SEQ ID NO: 7)
uagcagcacaucaugguuuaca, miR-221-3p mimic:
                                    (SEQ ID NO: 8)
agcuacauugucugcuggguuuc, miR-551b-3p mimic:
                                    (SEQ ID NO: 9)
gcgacccauacuugguuucag.
```

The pharmaceutical composition according to the present invention can further comprise at least one MAPK pathway inhibiting drug, wherein said antagonist and/or miRNA mimic is used against the resistance to MAPK pathway inhibiting drugs.

For example, MAPK pathway inhibiting drugs can be chosen from the group consisting of vemurafenib, Trametinib, dabrafenib, sorafenib, SB590885, PLX4720, XL281, RAF265, encorafenib, cobimetinib, Cl-1040, PD0325901, Binimetinib, selumetinib.

The present invention concerns also a method for in vitro diagnosis of resistance to MAPK pathway (or more specifically BRAF/MEK pathway) inhibiting drugs in tumors, said method comprising measuring the expression, in a biological sample, of at least two, three or all of the following microRNAs:

```
miR-199b-5p:
                                    (SEQ ID NO: 1)
cccaguguuuagacuaucuguuc, miR-204-5p:
                                    (SEQ ID NO: 2)
uucccuuugucauccuaugccu, miR-4443:
                                    (SEQ ID NO: 10)
uuggaggcguggguuuu, miR-4488:
                                    (SEQ ID NO: 11)
aggggggcgggcuccggcg, miR-145-5p:
                                    (SEQ ID NO: 3)
guccaguuuucccaggaaucccu, miR-18a-5p:
                                    (SEQ ID NO: 4)
uaaggugcaucuagugcagauag, miR-455-3p:
                                    (SEQ ID NO: 5)
gcaguccaugggcauauacac, miR-107:
                                    (SEQ ID NO: 6)
agcagcauuguacagggcuauca, miR-15b-5p:
                                    (SEQ ID NO: 7)
uagcagcacaucaugguuuaca, miR-221-3p:
                                    (SEQ ID NO: 8)
agcuacauugucugcuggguuuc, miR-551b-3p:
                                    (SEQ ID NO: 9)
gcgacccauacuugguuucag, miR-1234:
                                    (SEQ ID NO: 12)
ucggccugaccacccaccccac, miR-9-5p:
                                    (SEQ ID NO: 13)
ucuuugguuaucuagcuguauga, miR-1915-5p:
                                    (SEQ ID NO: 14)
accuugccuugcugcccgggcc, miR-4286:
                                    (SEQ ID NO: 15)
accccacuccugguacc, miR-575
                                    (SEQ ID NO: 16)
gagccaguuggacaggagc, miR-630
                                    (SEQ ID NO: 17)
aguauucuguaccagggaaggu,
``` wherein miR-199b-5p, miR-204-5p, miR-145-5p, miR-18a-5p, miR-455-3p, miR-107, miR-15b-5p, miR-221-3p, miR-551b-3p are down-expressed in the resistance to MAPK pathway (or more specifically BRAF/MEK pathway) inhibiting drugs, whereas miR-4443, miR-4488, miR-1234, miR-9-5p, miR-1915-5p, miR-4286, miR-575, miR-630 are over-expressed in the resistance to MAPK pathway (or more specifically BRAF/MEK pathway) inhibiting drugs in comparison with their expression in controls which do not present said resistance; preferably, said at least two microRNAs are different from miR-4443 and miR-18a-5p when the expression of only two microRNAs is measured. The tumors can be those which are BRAF mutated tumors and are treated with MAPK pathway (or more specifically BRAF/MEK pathway) inhibiting drugs.

It is a further object of the present invention, the use of at least two, three or all of the following microRNAs:

```
miR-199b-5p:
                                    (SEQ ID NO: 1)
cccaguguuuagacuaucuguuc, miR-204-5p:
                                    (SEQ ID NO: 2)
uucccuuugucauccuaugccu, miR-4443:
                                    (SEQ ID NO: 10)
uuggaggcguggguuuu, miR-4488:
                                    (SEQ ID NO: 11)
aggggggcgggcuccggcg, miR-145-5p:
                                    (SEQ ID NO: 3)
guccaguuuucccaggaaucccu, miR-18a-5p:
                                    (SEQ ID NO: 4)
uaaggugcaucuagugcagauag, miR-455-3p:
                                    (SEQ ID NO: 5)
gcaguccaugggcauauacac, miR-107:
                                    (SEQ ID NO: 6)
agcagcauuguacagggcuauca,
```

-continued miR-15b-5p:
(SEQ ID NO: 7)
uagcagcacaucaugguuuaca, miR-221-3p:
(SEQ ID NO: 8)
agcuacauugucugcugggvuuc, miR-551b-3p:
(SEQ ID NO: 9)
gcgacccauacuugguuucag, miR-1234:
(SEQ ID NO: 12)
ucggccugaccacccaccccac, miR-9-5p:
(SEQ ID NO: 13)
ucuuugguuaucuagcuguauga, miR-1915-5p:
(SEQ ID NO: 14)
accuugccuugcugcccgggcc, miR-4286:
(SEQ ID NO: 15)
accccacuccugguacc, miR-575
(SEQ ID NO: 16)
gagccaguuggacaggagc, miR-630
(SEQ ID NO: 17)
aguauucuguaccagggaaggu, as biomarkers for the in vitro diagnosis of the resistance of tumors to MAPK pathway (or more specifically BRAF/MEK pathway) inhibiting drugs, wherein miR-199b-5p, miR-204-5p, miR-145-5p, miR-18a-5p, miR-455-3p, miR-107, miR-15b-5p, miR-221-3p, miR-551b-3p are down-expressed in the resistance to MAPK pathway (or more specifically BRAF/MEK pathway) inhibiting drugs, whereas miR-4443, miR-4488, miR-1234, miR-9-5p, miR-1915-5p, miR-4286, miR-575, miR-630 are over-expressed in the resistance to MAPK pathway (or more specifically BRAF/MEK pathway) inhibiting drugs in comparison with their expression in controls which do not present said resistance; preferably said at least two microRNAs are different from miR-4443 and miR-18a-5p when are used only two microRNAs. As mentioned above the tumors can be those which are BRAF mutated tumors and are treated with MAPK pathway (or more specifically BRAF/MEK pathway) inhibiting drugs.

The present invention concerns also an antagonist of at least one of miR-4443, miR-4488, miR-1234, miR-9-5p, miR-1915-5p, miR-4286, miR-575, miR-630 and/or a miRNA mimic of at least one of miR-199b-5p, miR-204-5p, miR-145-5p, miR-18a-5p, miR-455-3p, miR-107, miR-551b-3p, miR-221-3p, miR-15b-5p for use in the treatment of tumors which are resistant to MAPK pathway (or more specifically BRAF/MEK pathway) inhibiting drugs, wherein said antagonist is chosen from the group consisting of antimiR-4443: aaaacccacgcctccaa (SEQ ID NO:18), antimiR-4488: cgccggagcccgccccct (SEQ ID NO:19), antimiR-1234: gtggggtgggtggtcaggccga (SEQ ID NO:20), antimiR-9-5p: tcatacagctagataaccaaaga (SEQ ID NO:21), antimiR-1915-5p: ggcccgggcagcaaggcaaggt (SEQ ID NO: 22), antimiR-4286: ggtaccaggagtggggt (SEQ ID NO:23), antimiR-575: gctcctgtccaactggctc (SEQ. ID. NO. 24), antimiR-630: accttccctggtacagaatact (SEQ ID NO:25), or the corresponding LNA of the above-mentioned antimiRNAs, whereas said miRNA mimic is chosen from the group consisting of miR-199b-5p mimic: cccaguguuuagacuaucuguuc (SEQ ID NO:1), miR-204-5p mimic: uucccuuugucauccuaugccu (SEQ ID NO:2), miR145-5p mimic: guccaguuuucccaggaaucccu (SEQ ID NO:3), miR-18a-5p mimic: uaaggugcaucuagugcagauag (SEQ ID NO:4), miR-455-3p mimic: gcaguccaugggcauauacac (SEQ ID NO: 5), miR-107 mimic: agcagcauuguacagggcuauca (SEQ ID NO:6), miR-15b-5p mimic: uagcagcacaucaugguuuaca (SEQ ID NO:7), miR-221-3p mimic: agcuacauugucugcugggvuuc (SEQ ID NO:8), miR-551b-3p mimic: gcgacccauacuugguuucag (SEQ ID NO:9). The tumors can be those which are BRAF mutated tumors and are treated with MAPK pathway (or more specifically BRAF/MEK pathway) inhibiting drugs.

The present invention concerns also a combination of an antagonist of at least one of miR-4443, miR-4488, miR-1234, miR-9-5p, miR-1915-5p, miR-4286, miR-575, miR-630 and/or of a miRNA mimic of at least one of miR-199b-5p, miR-204-5p, miR-145-5p, miR-18a-5p, miR-455-3p, miR-107, miR-551b-3p, miR-221-3p, miR-15b-5p with at least one MAPK pathway (or more specifically BRAF/MEK pathway) inhibiting drug for the simultaneous, sequential or separate use in the treatment of tumors which are resistant to MAPK pathway (or more specifically BRAF/MEK pathway) inhibiting drugs, wherein said antagonist is chosen from the group consisting of antimiR-4443: aaaacccacgcctccaa (SEQ ID NO:18), antimiR-4488: cgccggagcccgccccct (SEQ ID NO:19), antimiR-1234: gtggggtgggtggtcaggccga (SEQ ID NO:20), antimiR-9-5p: tcatacagctagataaccaaaga (SEQ ID NO:21), antimiR-1915-5p: ggcccgggcagcaaggcaaggt (SEQ ID NO: 22), antimiR-4286: ggtaccaggagtggggt (SEQ ID NO:23), antimiR-575: gctcctgtccaactggctc (SEQ. ID. NO. 24), antimiR-630: accttccctggtacagaatact (SEQ ID NO:25), or the corresponding LNA of the above-mentioned antimiRNAs, whereas said miRNA mimic is chosen from the group consisting of miR-199b-5p mimic: cccaguguuuagacuaucuguuc (SEQ ID NO:1), miR-204-5p mimic: uucccuuugucauccuaugccu (SEQ ID NO:2), miR145-5p mimic: guccaguuuucccaggaaucccu (SEQ ID NO:3), miR-18a-5p mimic: uaaggugcaucuagugcagauag (SEQ ID NO:4), miR-455-3p mimic: gcaguccaugggcauauacac (SEQ ID NO: 5), miR-107 mimic: agcagcauuguacagggcuauca (SEQ ID NO:6), miR-15b-5p mimic: uagcagcacaucaugguuuaca (SEQ ID NO:7), miR-221-3p mimic: agcuacauugucugcugggvuuc (SEQ ID NO:8), miR-551b-3p mimic: gcgacccauacuugguuucag (SEQ ID NO:9).

BRIEF DESRIPTION OF THE DRAWINGS

The present invention now will be described by an illustrative, but not limitative way, according to preferred embodiments thereof, with particular reference to the enclosed drawings, wherein:

FIG. 1 Schematic representation of the in vitro selection of two BRAF-mutated melanoma cell lines (i.e. M14 and WM266) until the development of resistance to a BRAFi by treating cells to increasing doses of the drug for about two months. At each step of drug increase total RNAs were extracted to perform Nanostring Platform analysis.

Figure 2:
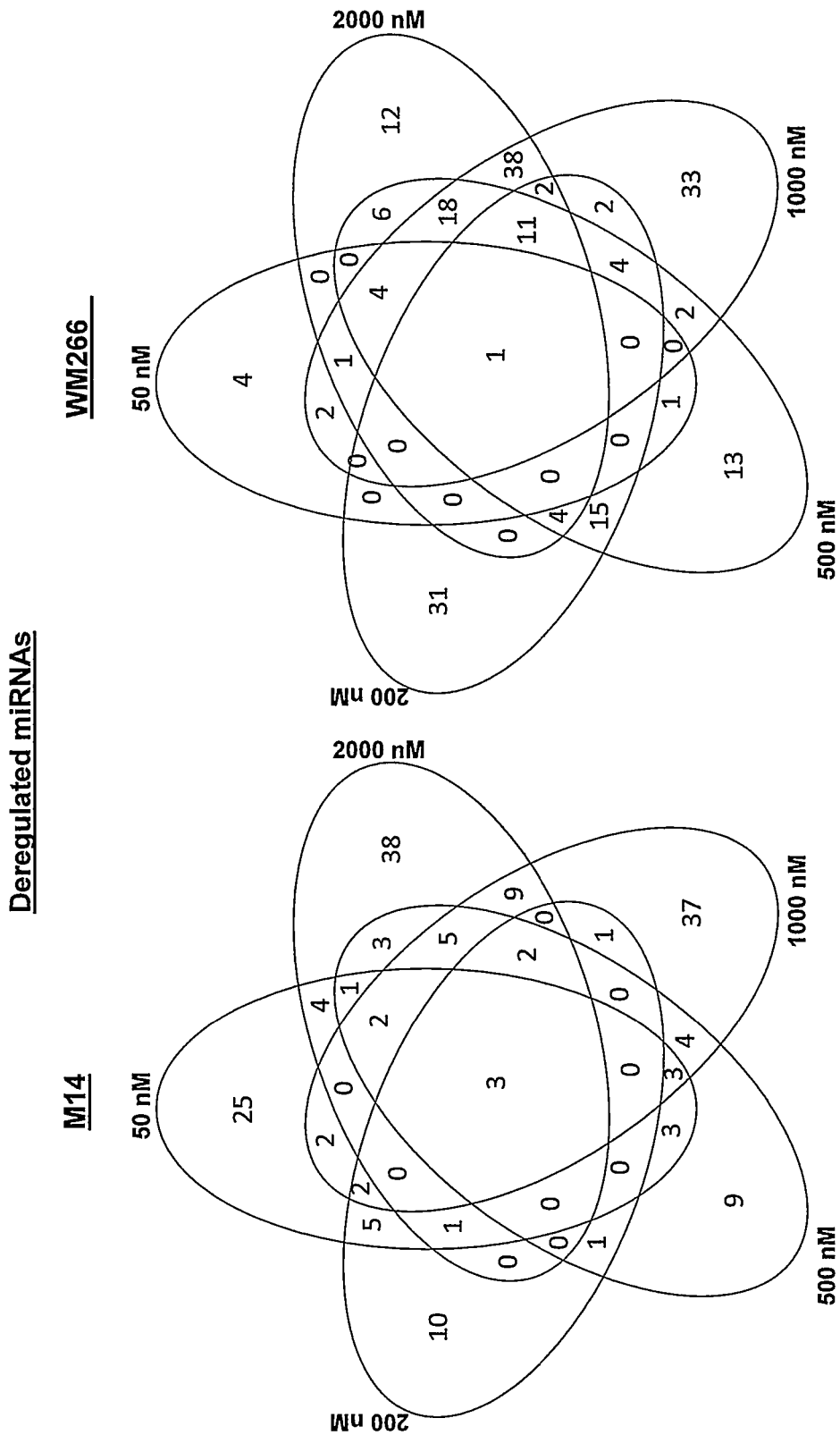

FIG. 2 Venn Diagrams show that each selection step is characterized by a distinct set of miRNAs expression changes.

Figure 3:
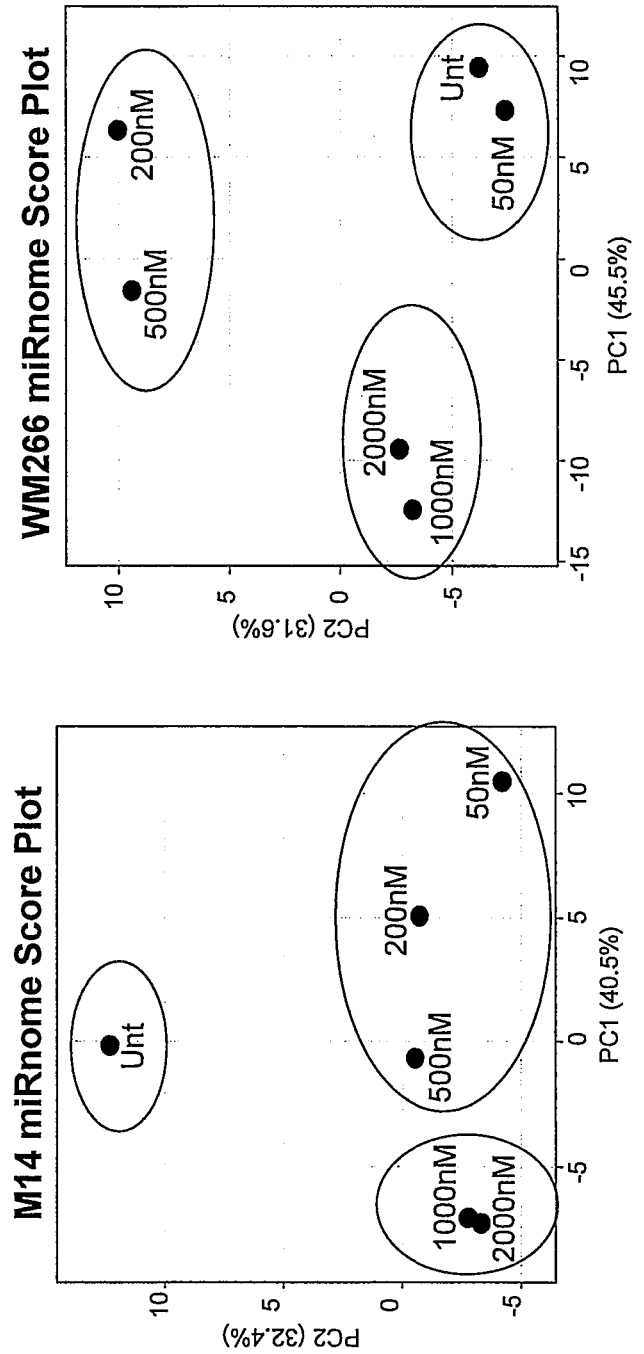

FIG. 3 Principal Component Analysis (PCA) of Nanostring data show that changes of the entire miRNome expression (n=800 miRNAs, black dots) are able to distinguish different drug sensitivity states.

Figure 4:
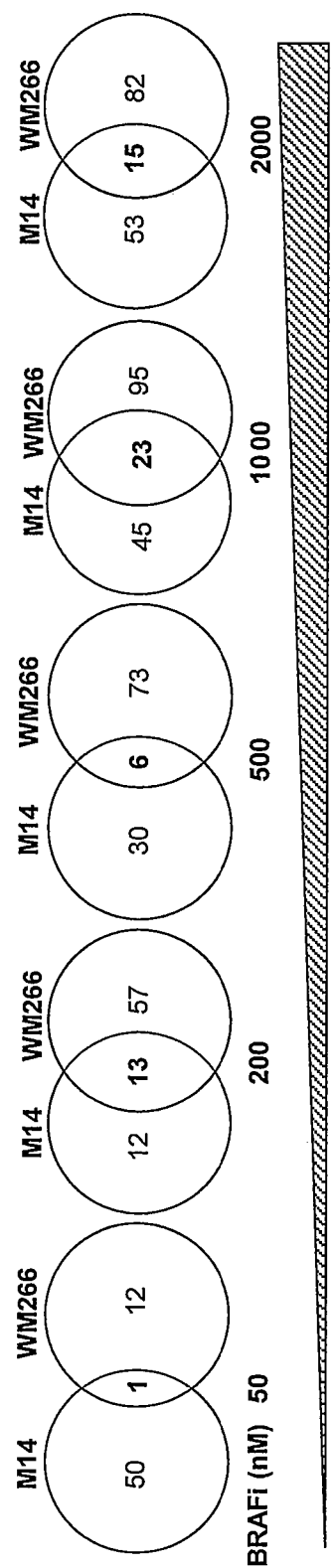

FIG. 4 Venn Diagrams show the common deregulated miRNAs between M14 and WM266 melanoma cells among the different steps of BRAFi selection (from 50 nM to 2000 nM).

Figure 5:
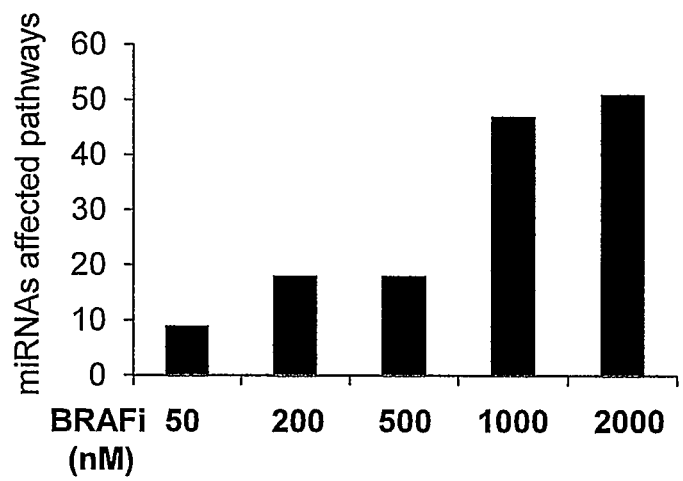

FIG. 5 Histogram shows that the last two steps of BRAFi selection (i.e. 1 uM and 2 uM BRAFi) are characterized by the highest number of pathways affected by commonly deregulated miRNAs.

Figure 6:
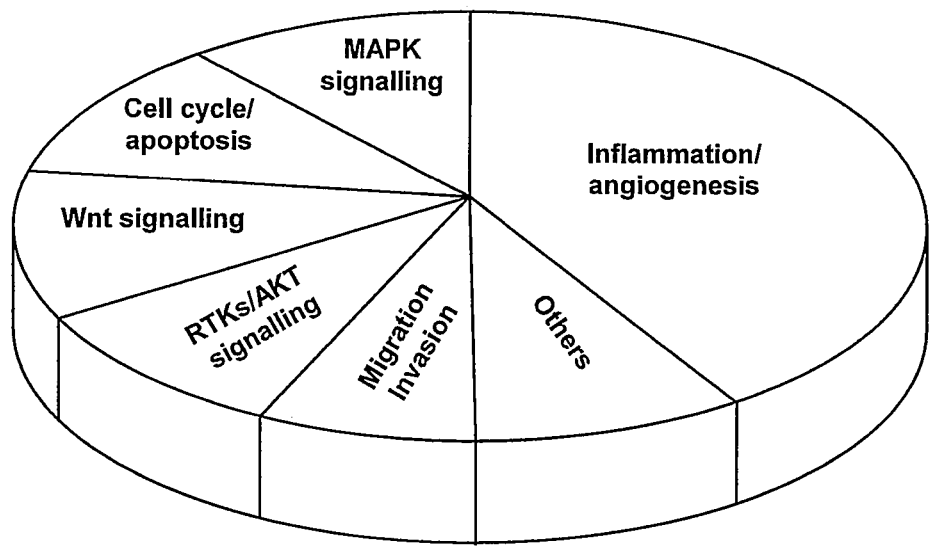

FIG. 6 Cake Graph show the main molecular pathways affected by the deregulated miRNAs identified through Nanostring analysis.

Figure 7:
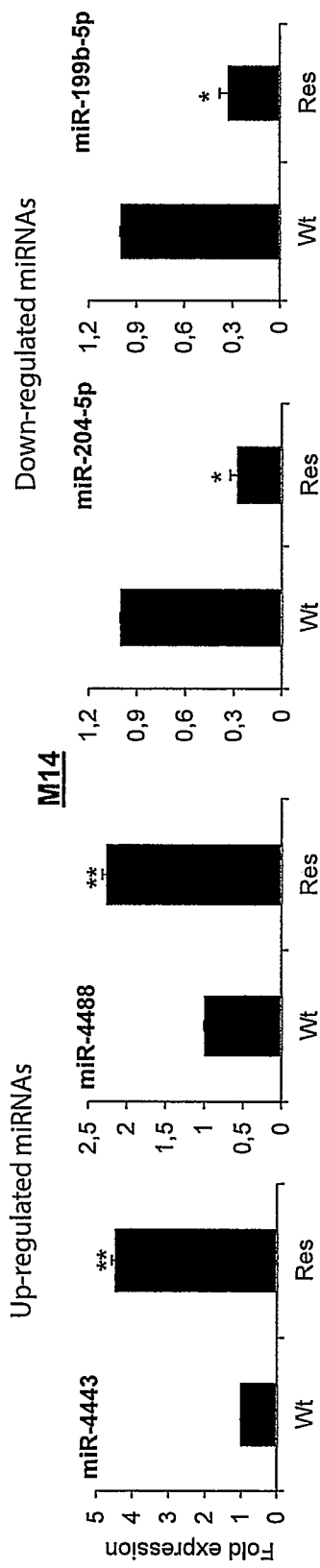

FIG. 7 Quantitative Real Time PCR analysis of miR-4443, miR-4488, miR-204-5p and miR-199b-5p expression levels between M14 BRAFi-sensitive melanoma cells and their BRAFi-resistant counterparts. Data are mean±s.d. from three independent experiments. P<0.05.

Figure 8:
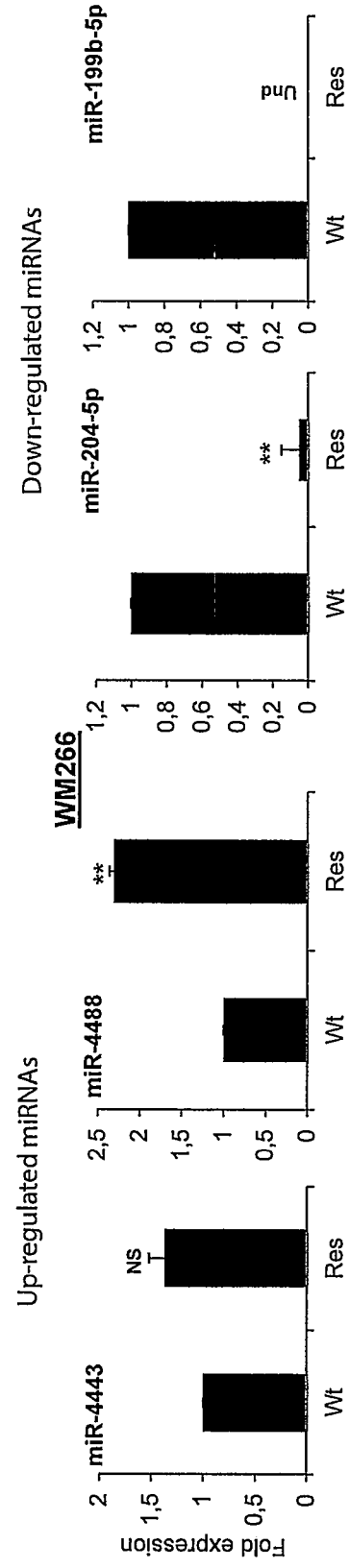

FIG. 8 Quantitative Real Time PCR analysis of miR-4443, miR-4488, miR-204-5p and miR-199b-5p expression levels between WM266 BRAFi-sensitive melanoma cells and their BRAFi-resistant counterparts. Data are mean±s.d. from three independent experiments. P<0.05.

Figure 9:
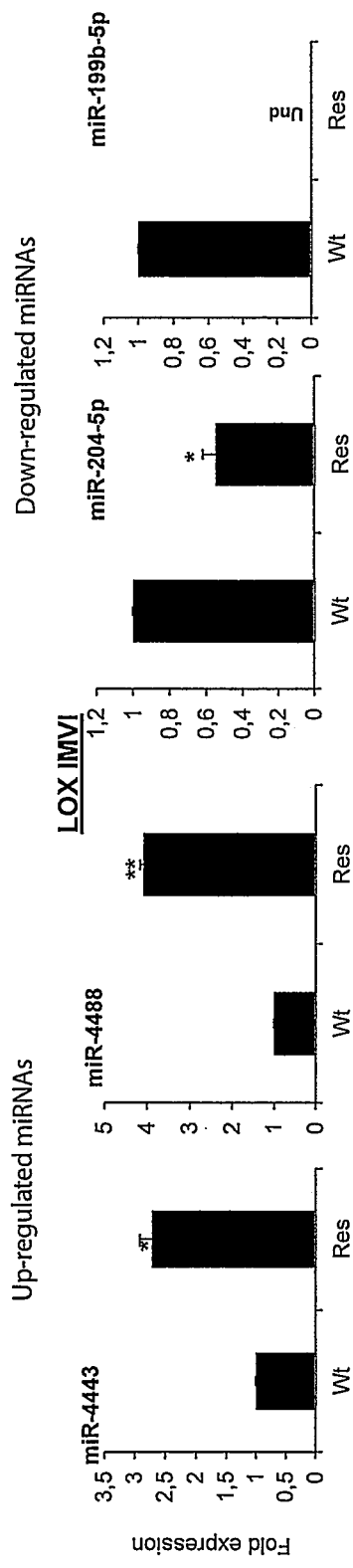

FIG. 9 Quantitative Real Time PCR analysis of miR-4443, miR-4488, miR-204-5p and miR-199b-5p expression levels between LOX IMVI BRAFi-sensitive melanoma cells and their BRAFi-resistant counterparts. Data are mean±s.d. from three independent experiments. P<0.05.

Figure 10:
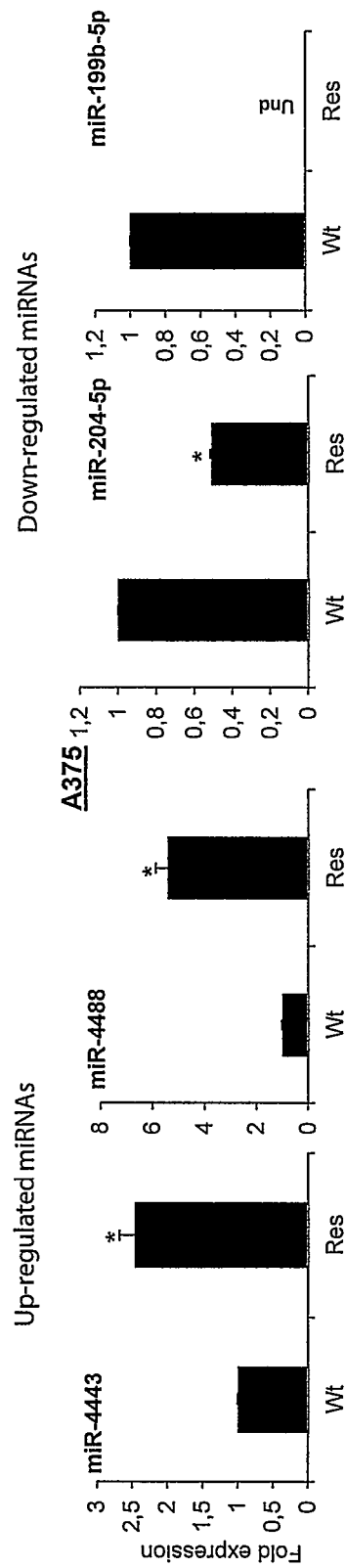

FIG. 10 Quantitative Real Time PCR analysis of miR-4443, miR-4488, miR-204-5p and miR-199b-5p expression levels between A375 BRAFi-sensitive melanoma cells and their BRAFi-resistant counterparts. Data are mean±s.d. from three independent experiments. P<0.05.

Figure 11:
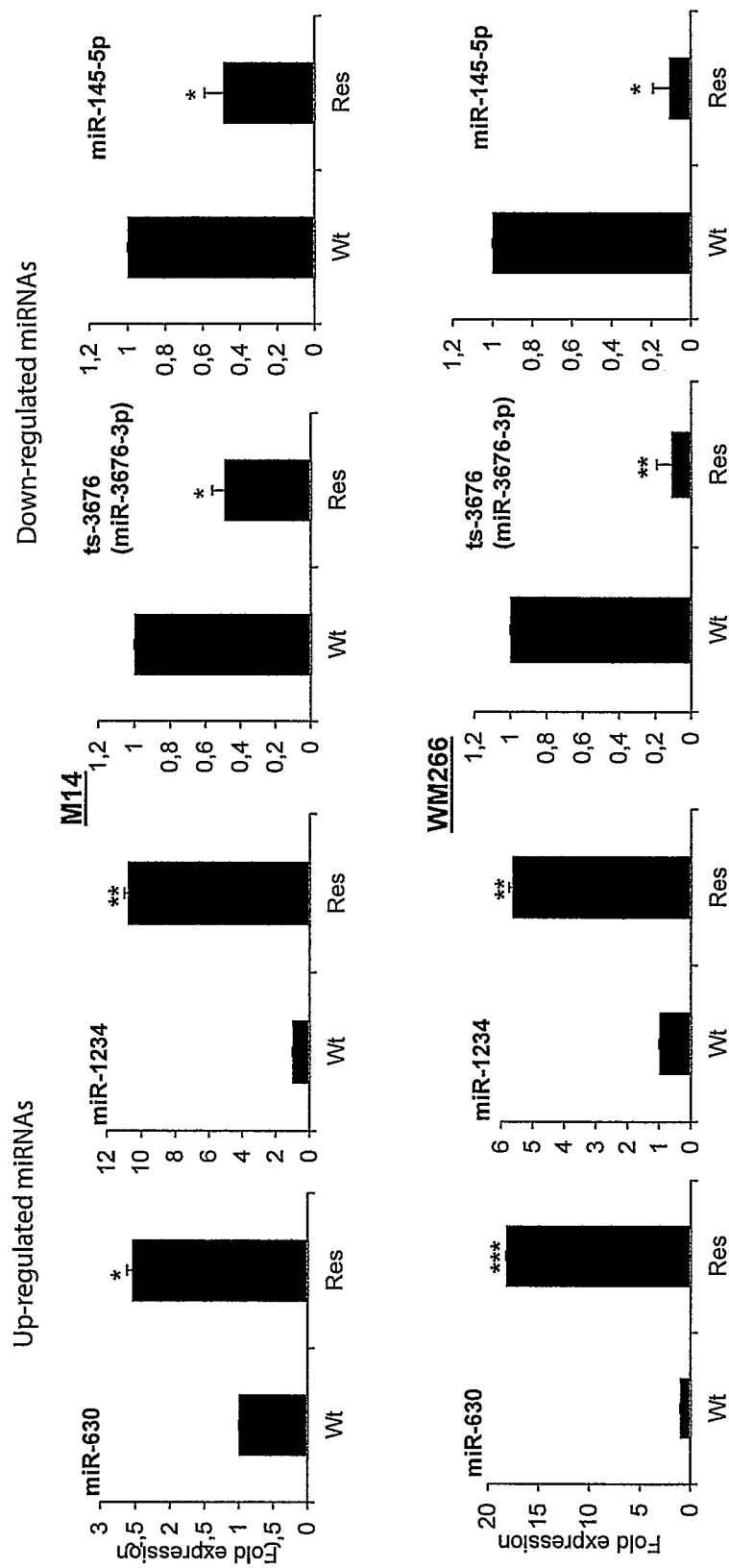

FIG. 11 Quantitative Real Time PCR analysis of miR-630, miR-1234, miR-3676-3p and miR-145-5p expression levels between M14 and WM266 BRAFi-sensitive melanoma cells and their BRAFi-resistant counterparts. Data are mean±s.d. from three independent experiments. P<0.05. miR-3676-3p originally identified as a miRNA is a tsRNA.

Figure 12:
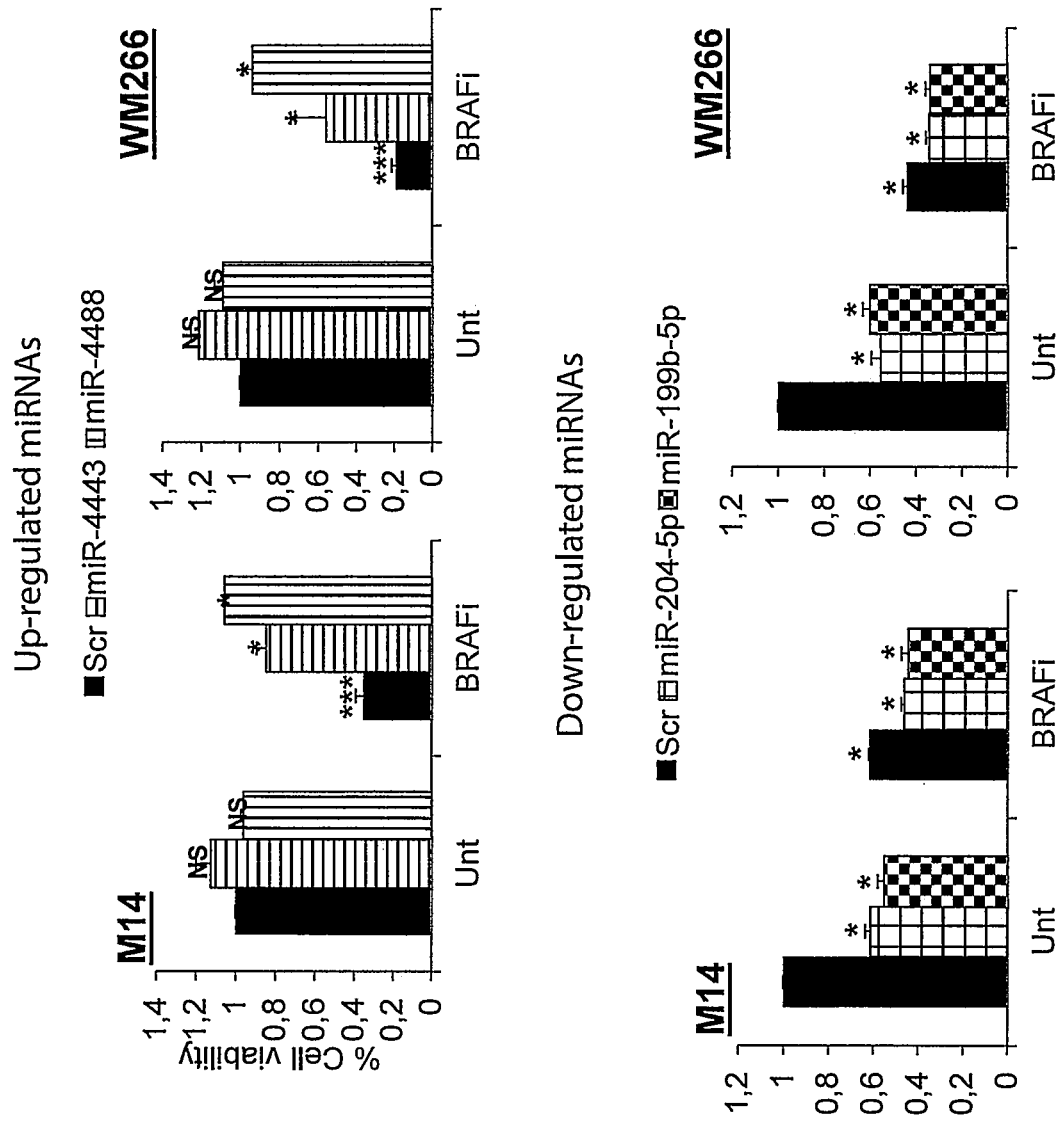

FIG. 12 Histograms show that enforced expression of the two UPMIRNAs (i.e. miR-4443 and miR-4488) and of the two DOWNMIRNAs (i.e. miR-204-5p and miR-199b-5p) differently affects BRAFi action on cell viability. Data are mean±s.d. from three independent experiments. P<0.05.

Figure 13:
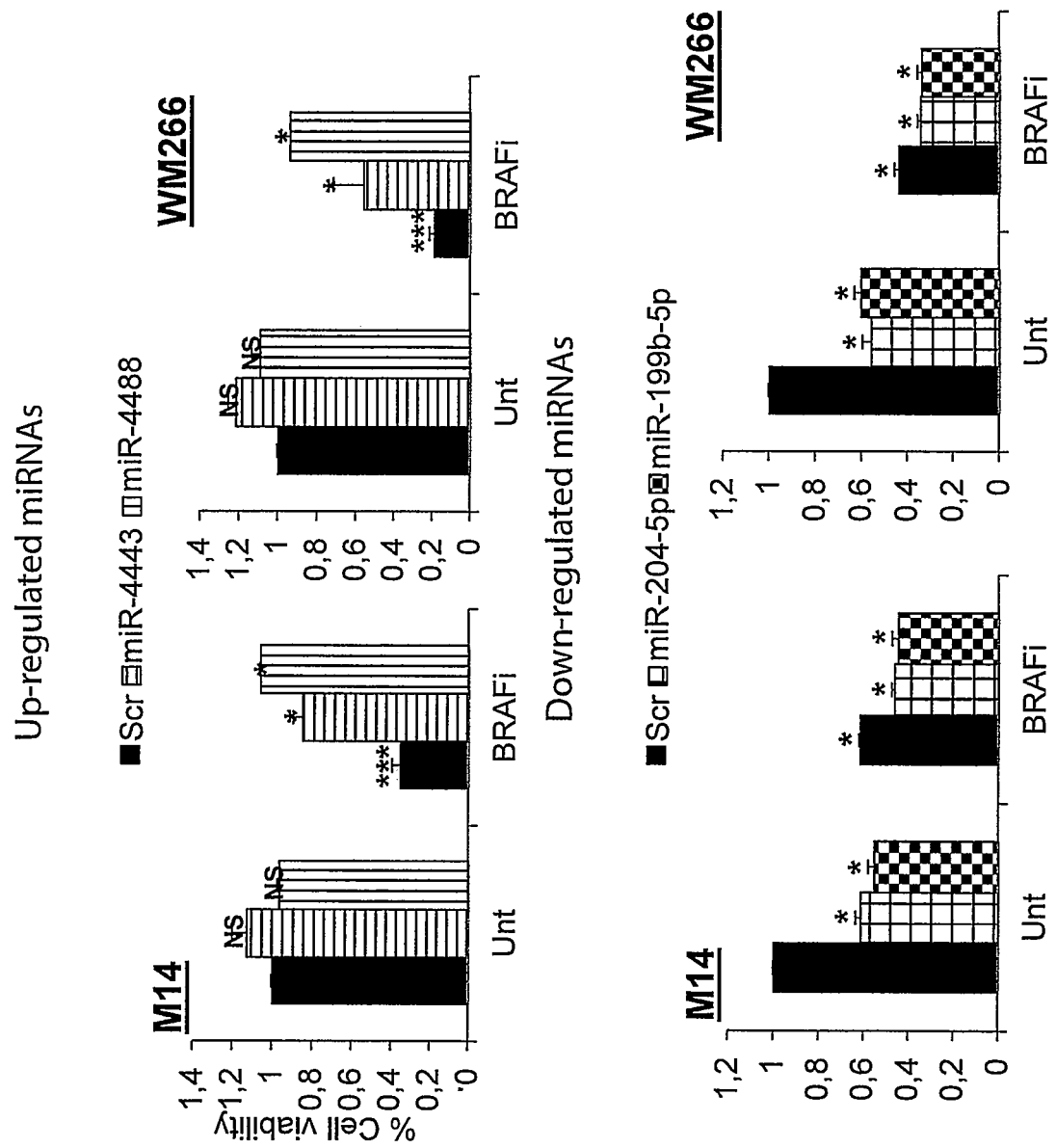

FIG. 13 Histograms show that enforced expression of the two UPMIRNAs (i.e. miR-4443 and miR-4488) and of the two DOWNMIRNAs (i.e. miR-204-5p and miR-199b-5p) differently affects BRAFi induction of apoptosis, measured through caspase 3/7 activation. Data are mean±s.d. from three independent experiments. P<0.05.

FIG. 14 Histograms show that the inhibition of the UPMIRNAS (i.e. miR-4443 and miR-4488) through specific antagomiRs inhibits both $M14^S$ and $M14^R$ melanoma cell colony formation. Data are mean±s.d. from three independent experiments. P<0.05.

FIG. 15 Histogram show that enforced expression of the two DOWNMIRNAs (i.e. miR-204-5p and miR-199b-5p) inhibits $M14^R$ melanoma cell colony formation. Data are mean±s.d. from three independent experiments. P<0.05.

Figure 16:
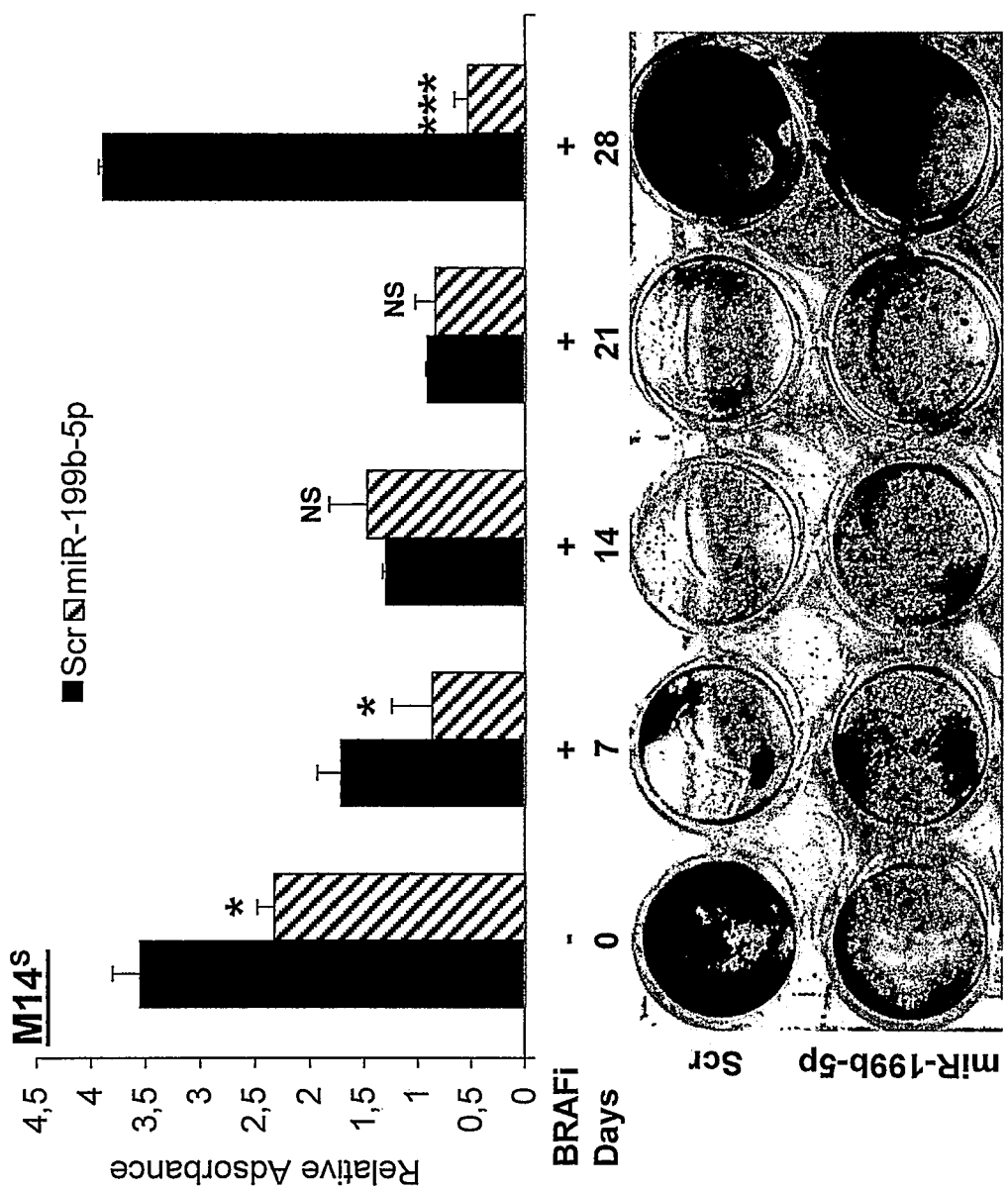

FIG. 16 $M14^S$ melanoma cells were transfected with the indicated miRNAs for 72 h and then stained with Crystal violet (day 0). The remaining plates were treated with 1 µM vemurafenib every 48 h and then stained after 7, 14, 21 and 28 days. Data are mean±s.d. from three independent experiments. P<0.05. The pictures shown are representative of three independent experiments.

Figure 17:
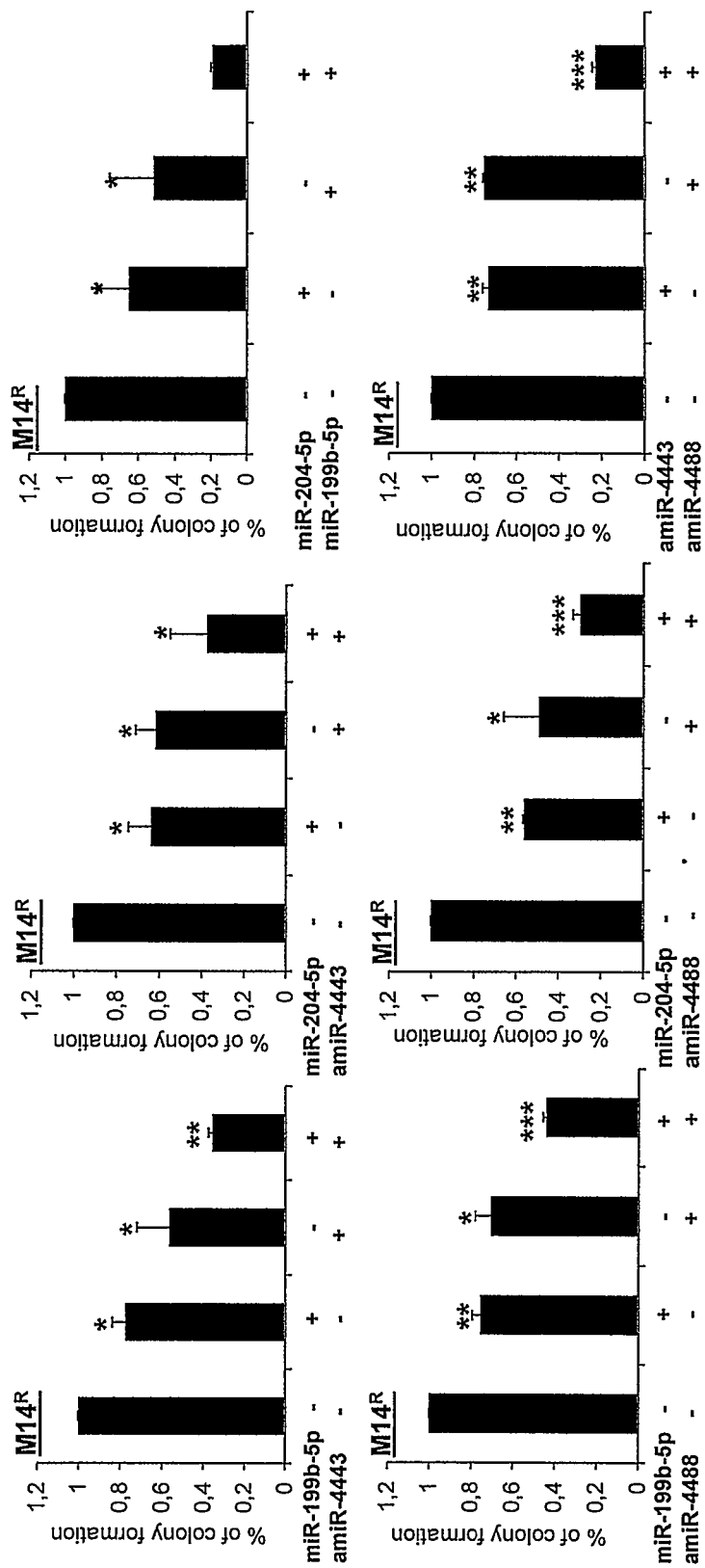

FIG. 17 Histograms show that targeting miRNAs in different combinations either through UPMIRNAS inhibition (i.e. amiR-4443 and amiR-4488) and/or DOWNMIRNAs enforced expression (i.e. miR-204-5p and miR-199b-5p) strongly inhibit $M14^R$ melanoma cell growth as compared to single treatments. Data are mean±s.d. from three independent experiments. P<0.05.

Figure 18:
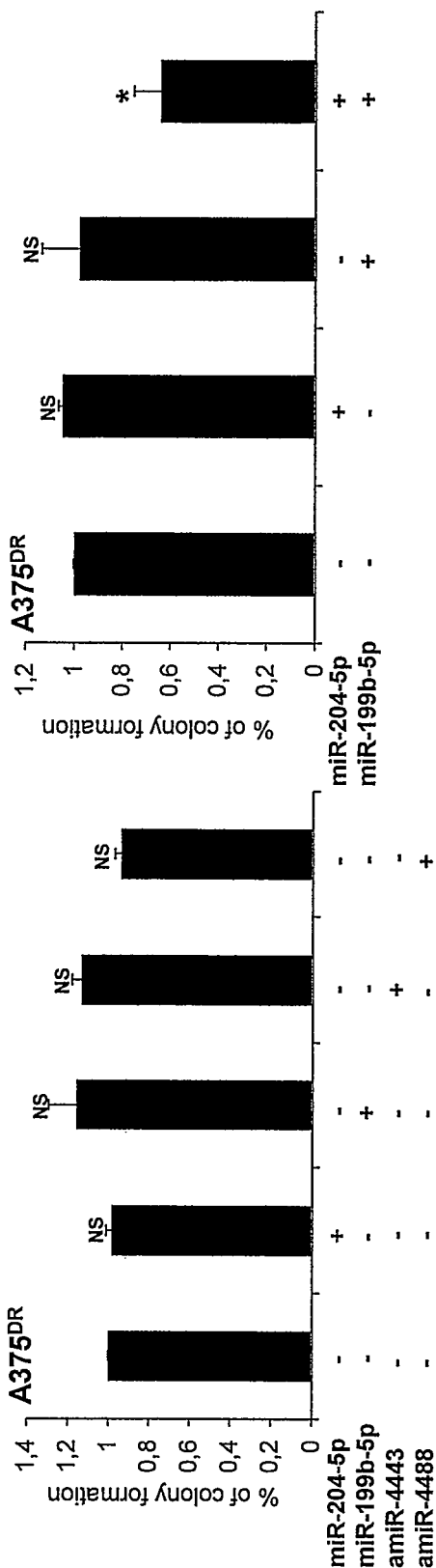

FIG. 18 Left histogram shows that targeting single miRNAs either through UPMIRNAS inhibition (i.e. amiR-4443 and amiR-4488) or DOWNMIRNAs enforced expression (i.e. miR-204-5p and miR-199b-5p) is not able to affect $A375^{DR}$ melanoma cell (resistant to BRAF and MEK inhibitors) colony formation. In contrast, the combinatorial treatment of miR-204-5p and miR-199b-5p strongly reduces $A375^{DR}$ colony formation as compared to single transfections. Data are mean±s.d. from three independent experiments. P<0.05.

Figure 19:
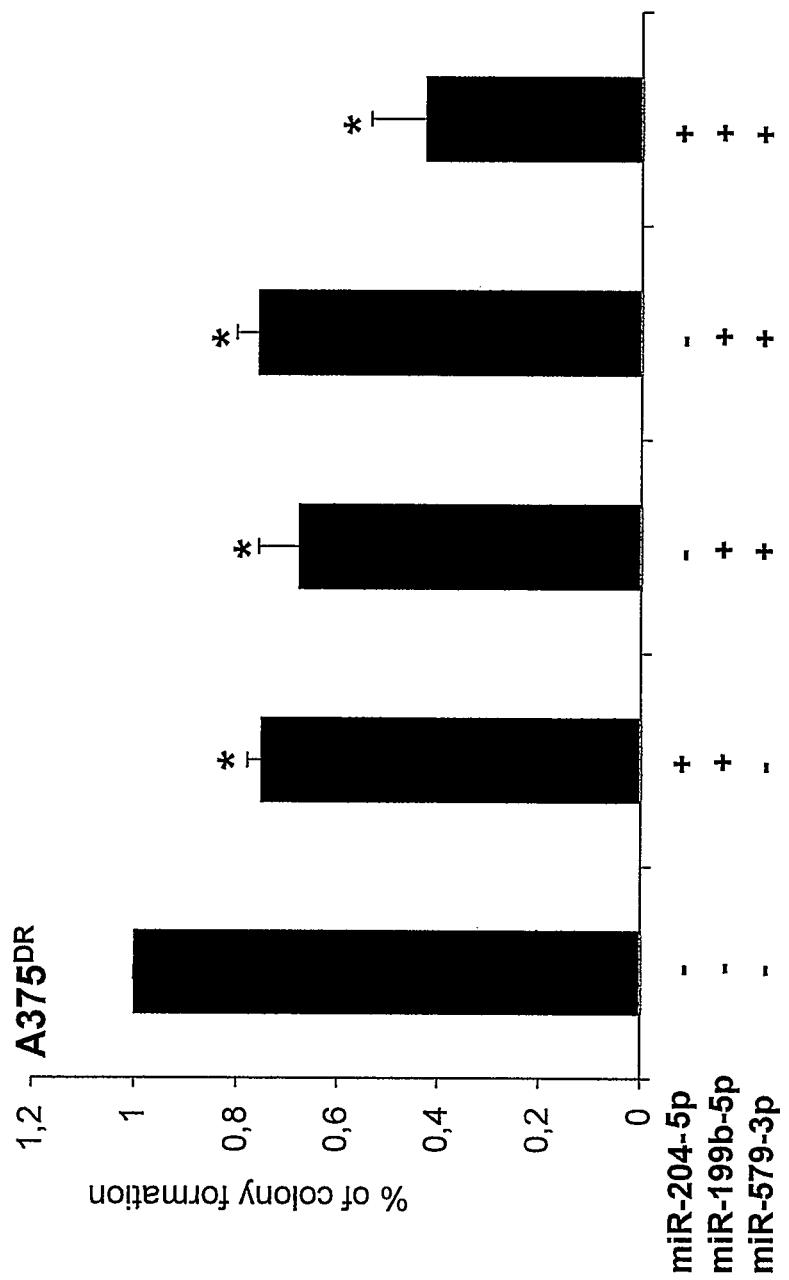

FIG. 19 The combinatorial treatment of miR-204-5p, miR-199b-5p and miR-579-3p strongly reduces $A375^{DR}$ colony formation as compared to double transfections. Data are mean±s.d. from three independent experiments. P<0.05.

Figure 20:
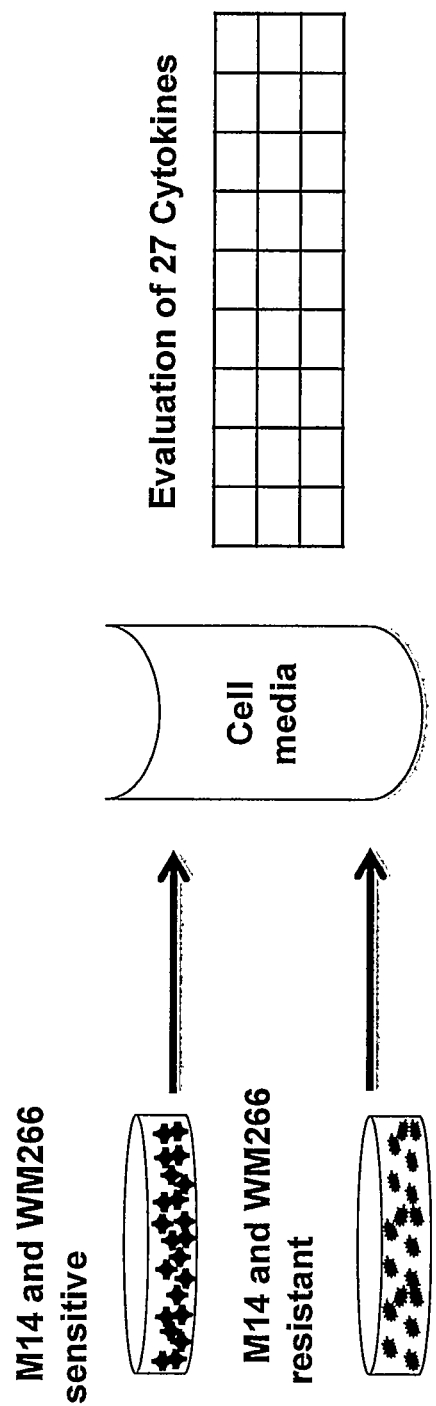

FIG. 20 Schematic representation of the evaluation of 27 cytokines in cell-derived supernatants through an ELISA-based approach.

Figure 21:
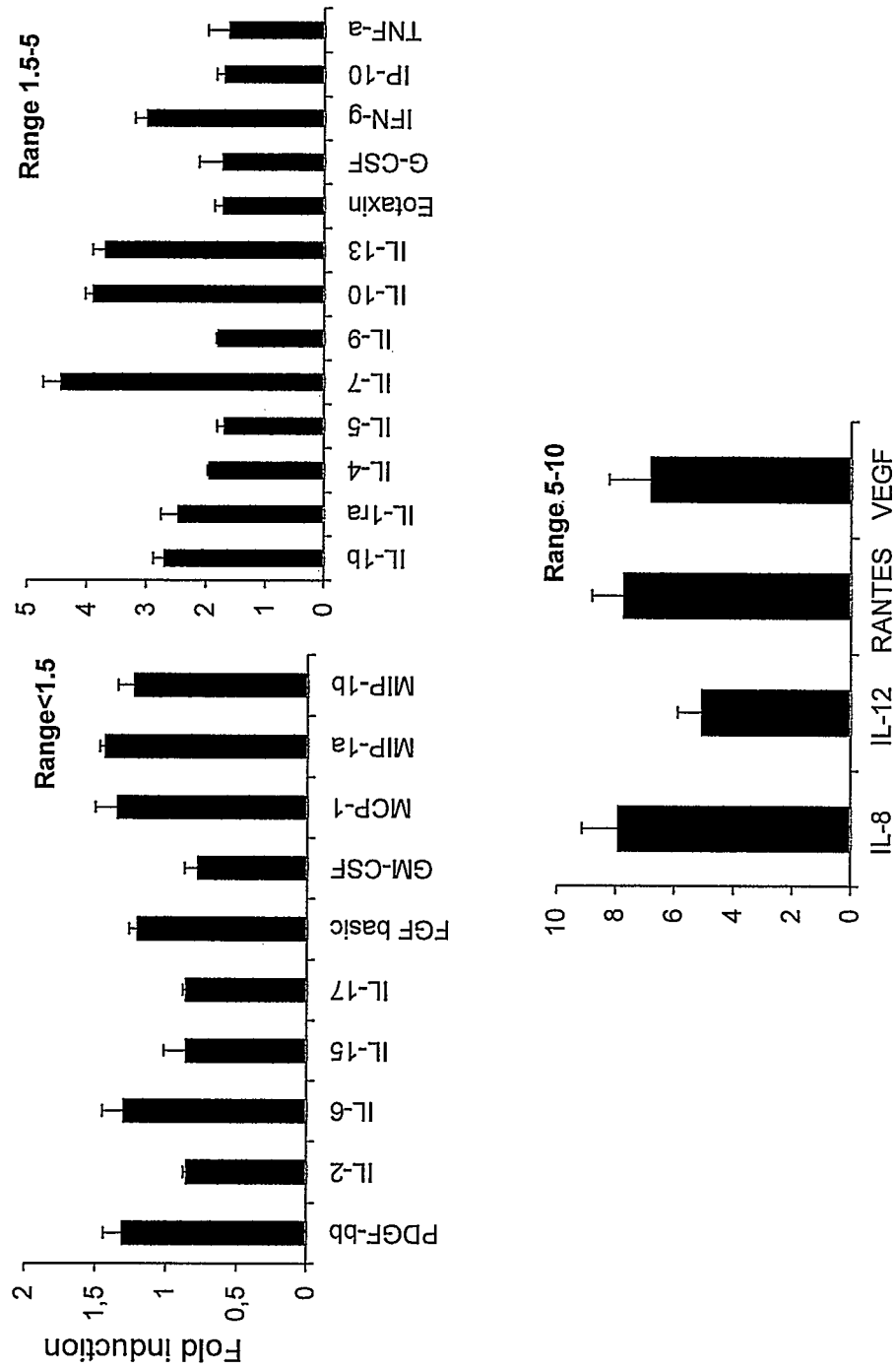

FIG. 21 Histograms of the fold induction of cytokines and chemokines in $M14^R$ cell-derived supernatants compared to their sensitive counterparts are divided in three distinct groups with a high, medium and low degree of upregulation respectively. A fold change greater than 1.3 was considered significant by evaluating the ratio between the cytokine levels in drug resistant cells compared to drug sensitive cells.

FIG. 22 Histograms of the fold induction of cytokines and chemokines in $WM266^R$ cell-derived supernatants compared to their sensitive counterparts are divided in three distinct groups with a high, medium and low degree of upregulation respectively. A fold change greater than 1.3 was considered significant by evaluating the ratio between the cytokine levels in drug resistant cells compared to drug sensitive cells.

Figure 23:
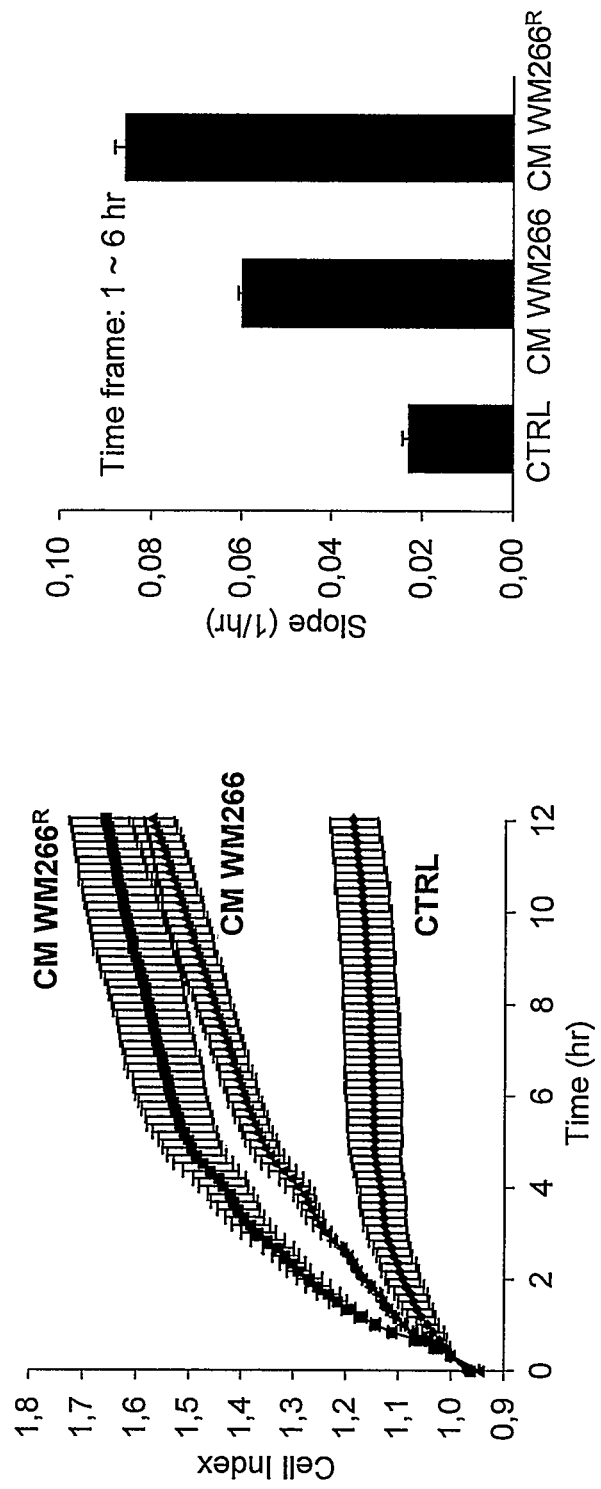

FIG. 23 Cell Index and Slope induction results indicate that conditioned media from $WM266^R$ melanoma cells is able to induce cell migration as compared to cell media from sensitive counterparts and CTRL media.

FIG. 24 Conditioned media from $WM266^R$ melanoma cells induce endothelial tube formation differently from the conditioned medium derived from $WM266^S$. For the quantitative analysis only tubular structures formed by cord-like structures exceeding 100 µm in length are considered. Data are mean±s.d. from three independent experiments. P<0.05. The pictures shown are representative of three independent experiments.

Figure 25:
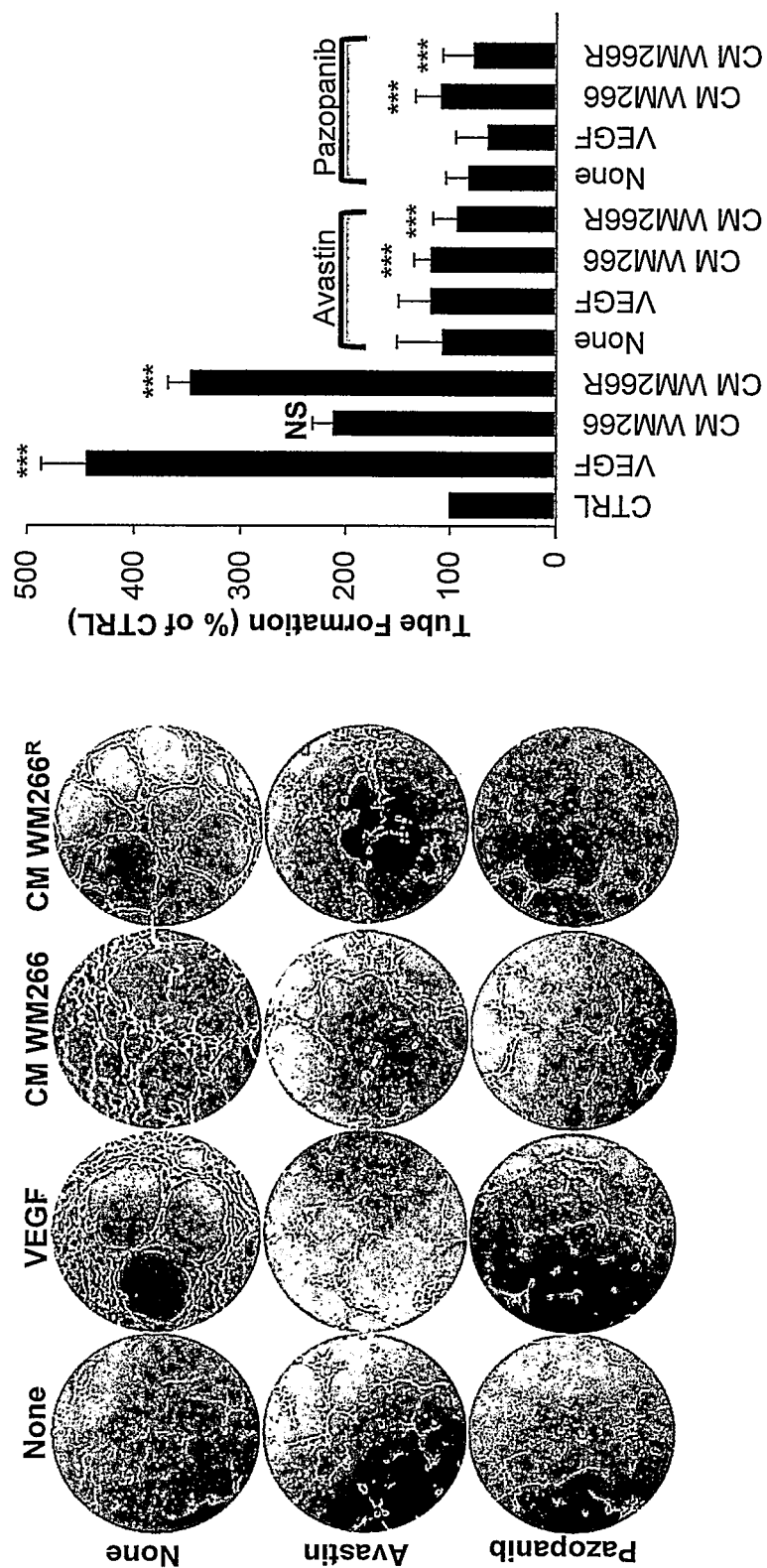

FIG. 25 Conditioned media from $WM266^R$ melanoma cells-induced endothelial tube formation is blocked by VEGFR inhibitors Avastin and Pazopanib. Quantitative analysis of tubular structures has been performed as previously reported. Data are mean±s.d. from three independent experiments. P<0.05. The pictures shown are representative of three independent experiments.

Figure 26:
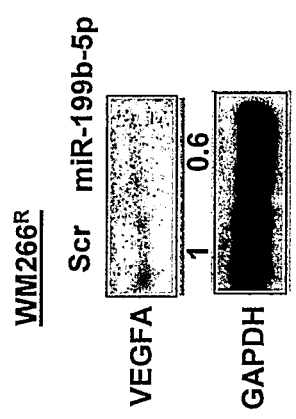

FIG. 26 $WM266^R$ melanoma cells transfected with Scrambled miRNA or miR-199b-5p were harvested and subjected to Western blot analysis to detect VEGFA and GAPDH protein levels.

Figure 27:
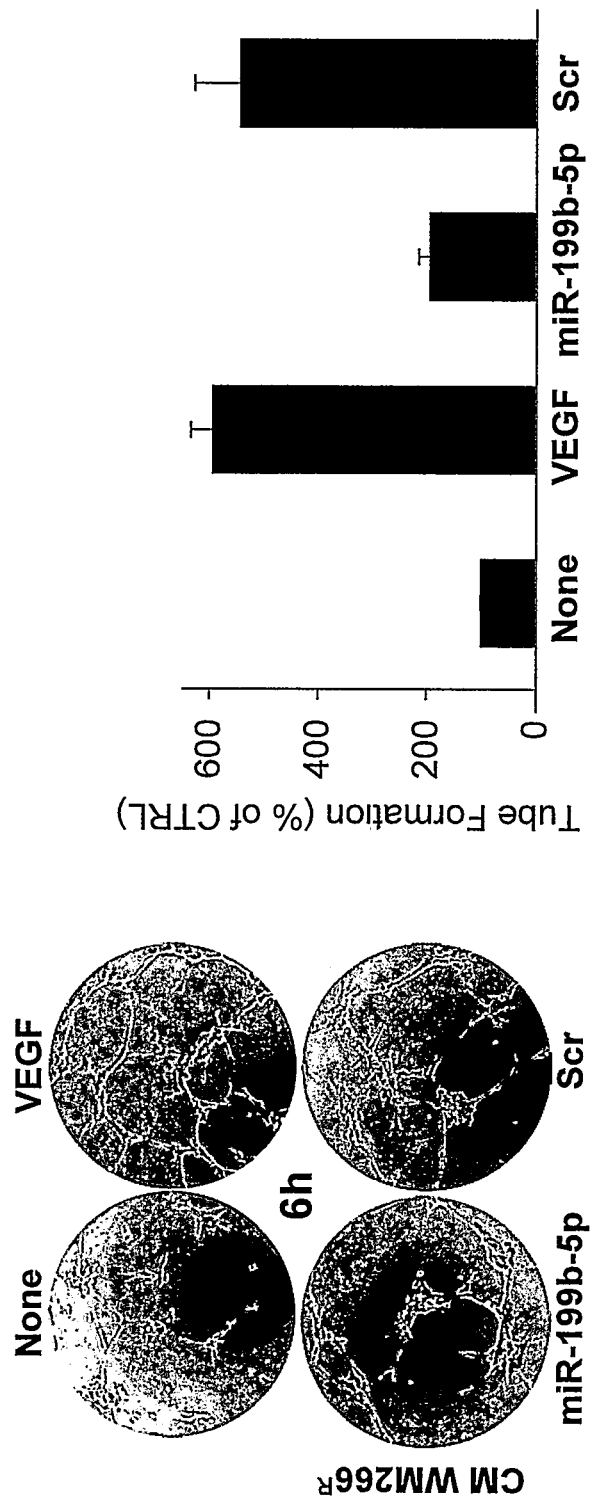

FIG. 27 Conditioned media from $WM266^R$ transfected with Scrambled miRNA or miR-199b-5p was used to induce endothelial tube formation. Quantitative analysis of tubular structures has been performed as previously reported. Data are mean±s.d. from three independent experiments. P<0.05. The pictures shown are representative of three independent experiments.

Figure 28:
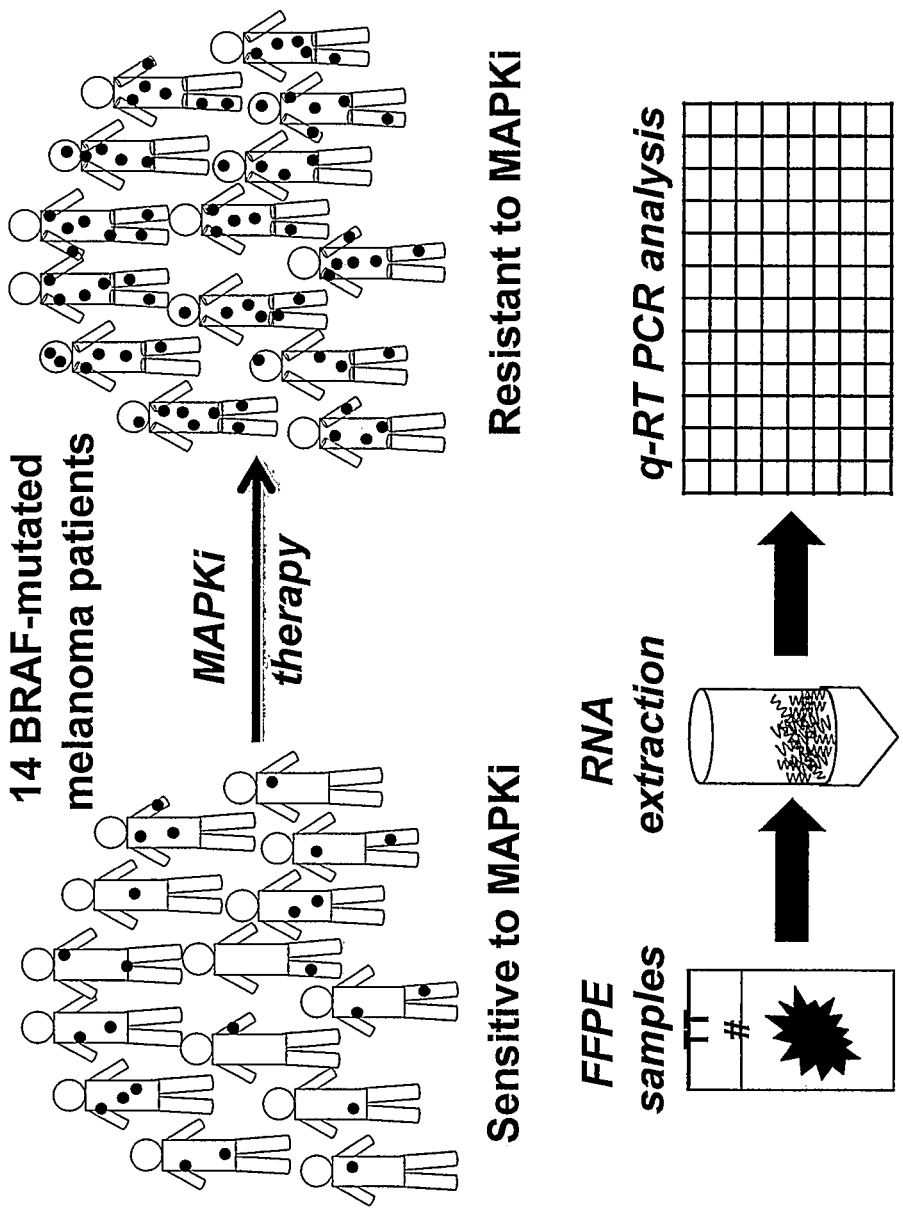

FIG. 28 Total RNA from 14 matched tumour samples before initiation of targeted therapy and after tumour progression was extracted and subjected to qRT-PCR for miRNA expression levels.

Figure 29:
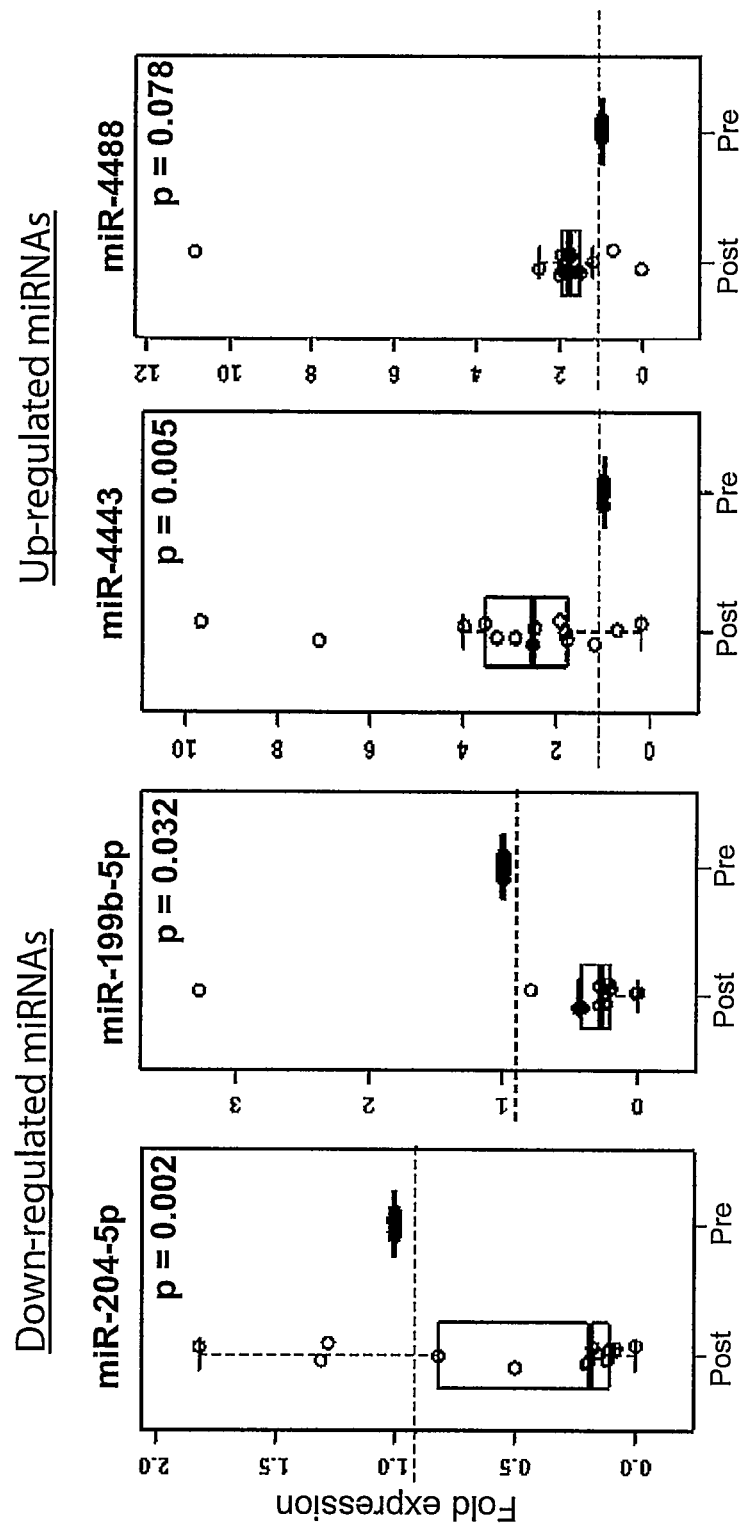

FIG. 29 Box-whisker plots show that miR-204-5p and miR-199b-5p are down-regulated in MAPKi-resistant tumours, whereas miR-4443 and miR-4488 are up-regulated.

Figure 30:
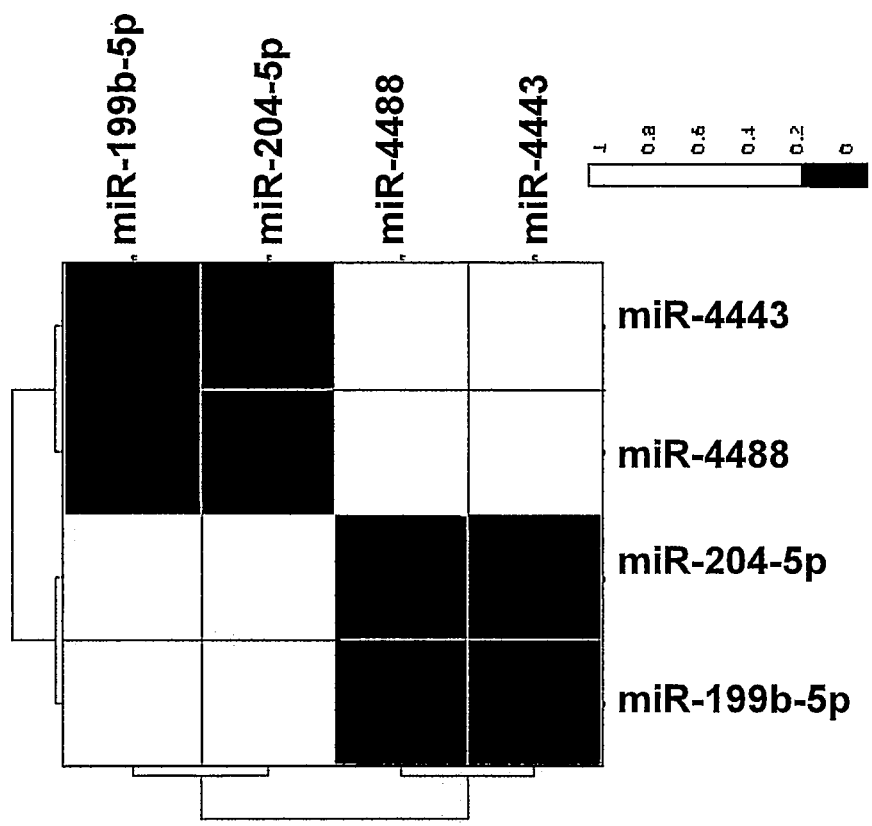

FIG. 30 Heatmap evaluates the correlation of the expression values of the four miRNAs between them by Pearson correlation coefficients. Low and high expression levels are evidenced by black and white colors, respectively.

Figure 31:
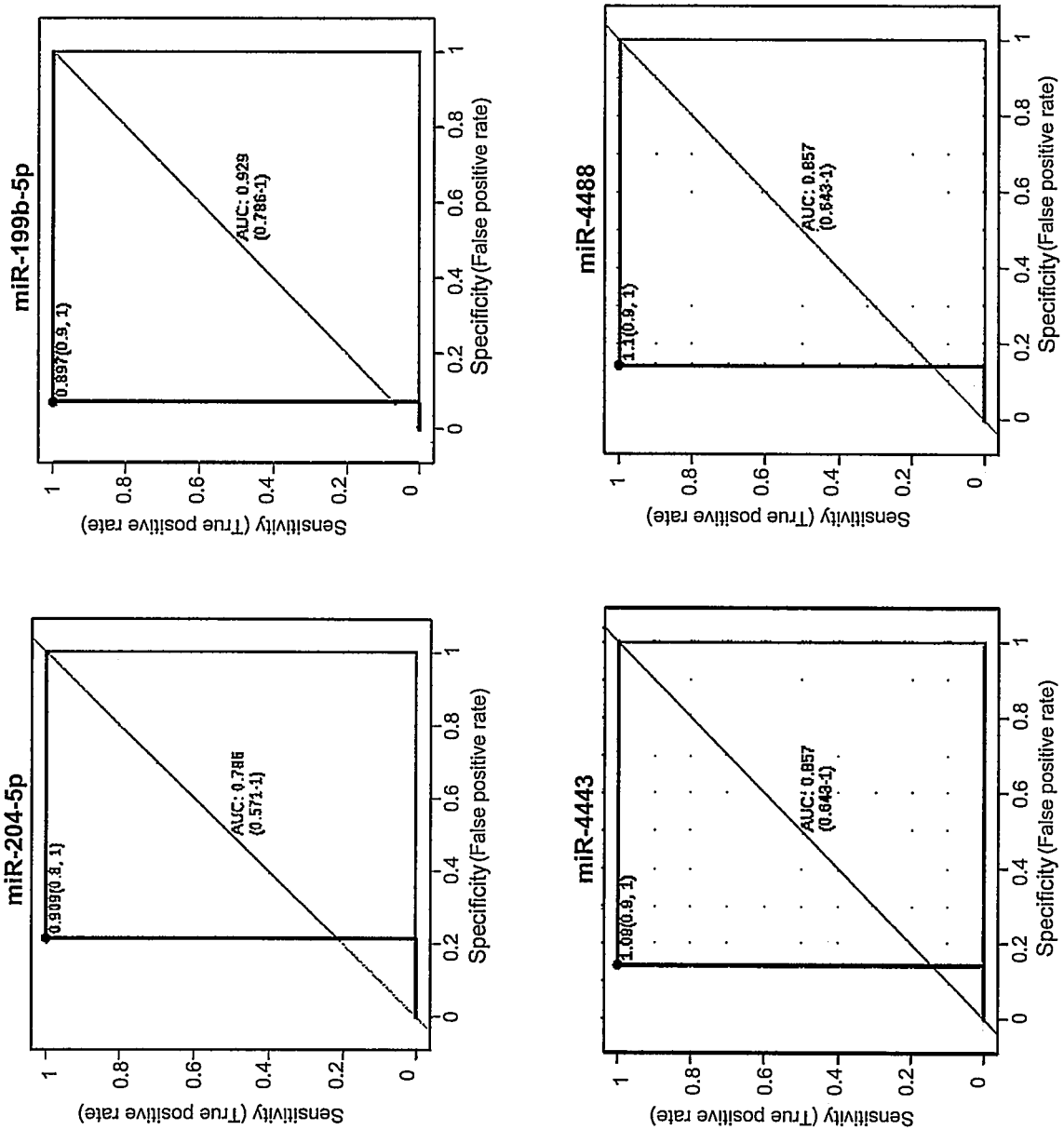

FIG. 31 Area Under Curve (AUC) evaluates the sensitivity, specificity and accuracy of the classifier. miR-199b-5p and miR-204-5p yield an AUC of 0.929 and 0.786; miR-4488 and miR-4443 yield an AUC of 0.857.

Figure 32:
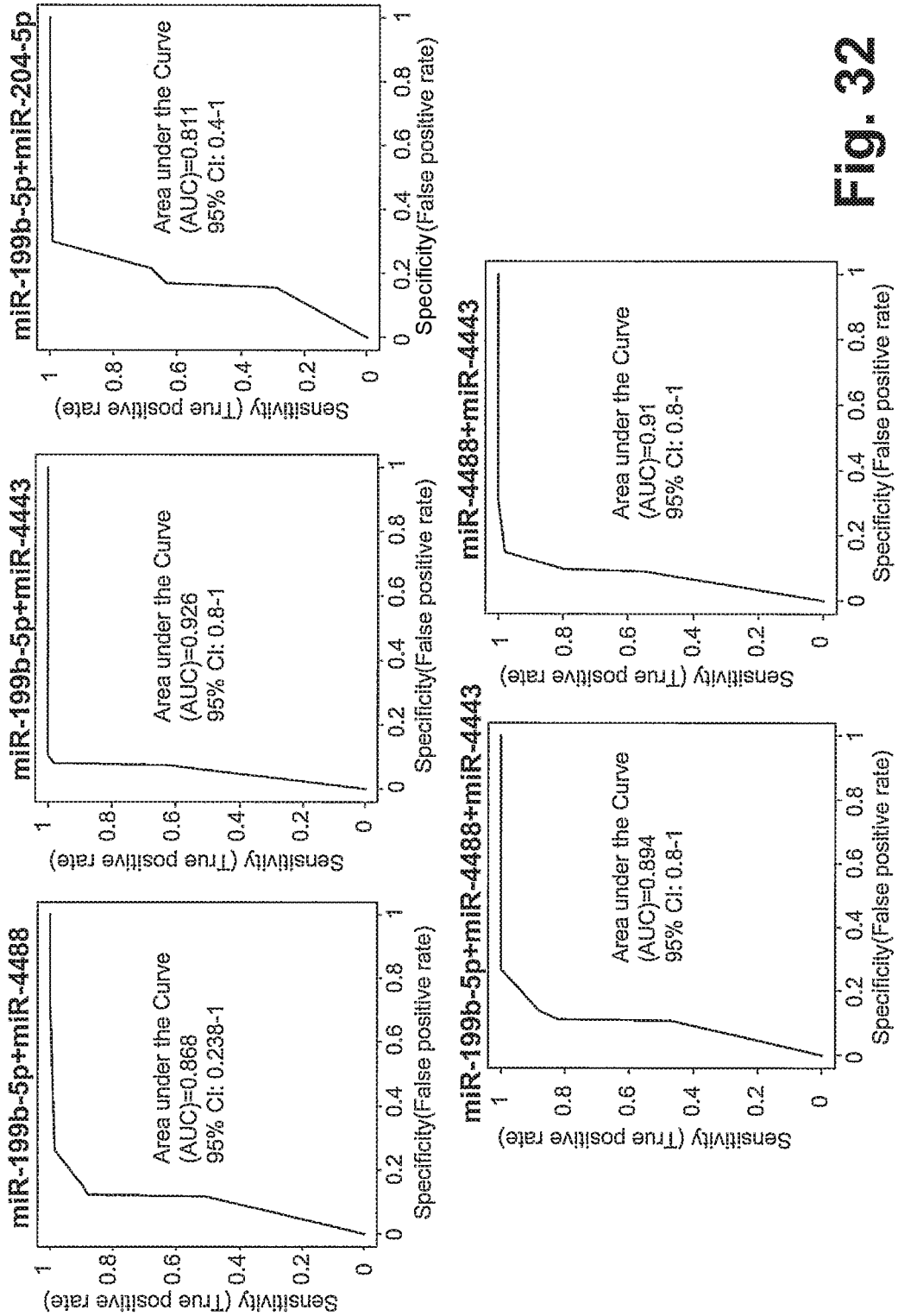

FIG. 32 Significant AUC values have been obtained for the combinations: miR-199b-5p+miR4488 (0.868), miR-199b-5p+miR-4443 (0.926), miR-199b-5p+miR-204-5p (0.811), miR-199b-5p+miR-4443+miR-4488 (0.894) and miR-4443+miR-4488 (0.91) in tumor biopsies from melanoma patients.

Figure 33:
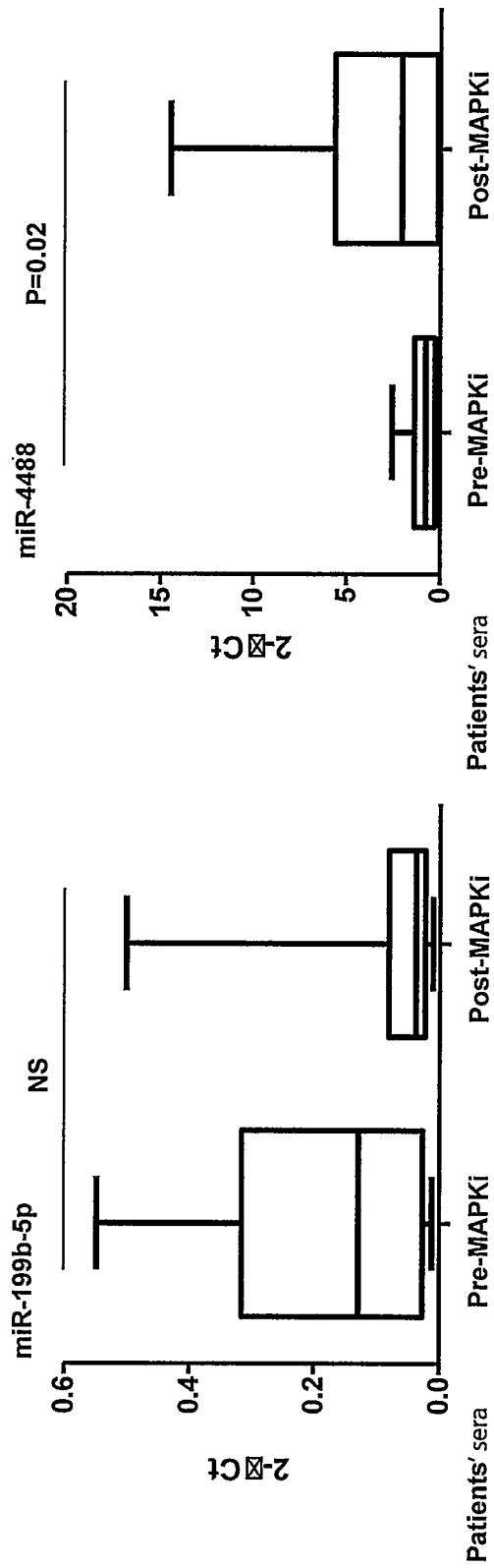

FIG. 33 Cell-free miRNAs were isolated from patients' sera before and after MAPKi targeted therapies and qRT-PCR performed on the expression levels of miR-199b-5p and miR-4443. Results are shown as box-whisker plots.

Figure 34:
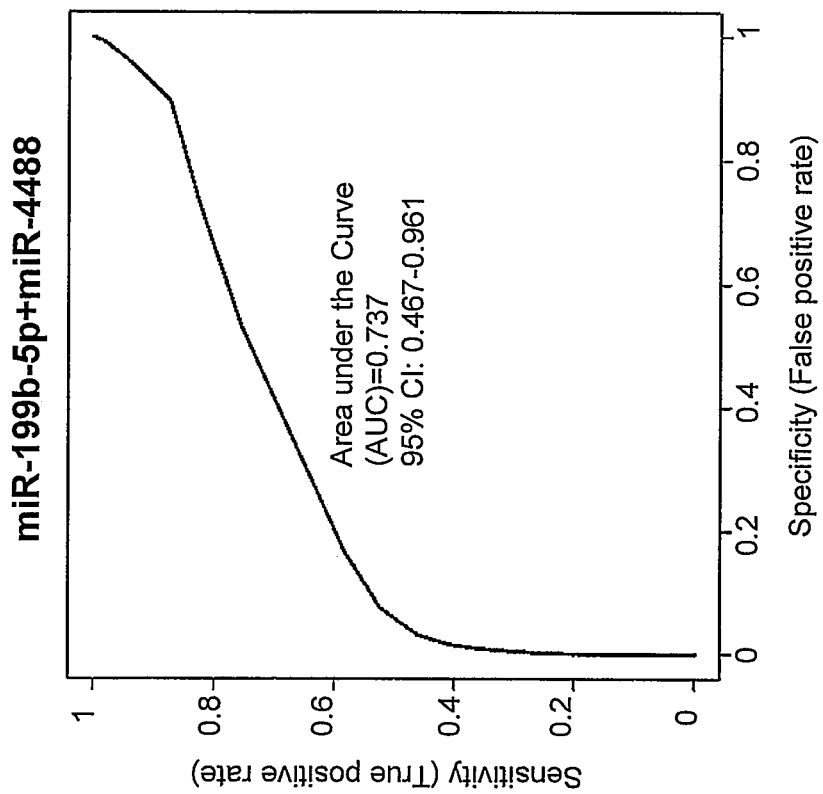

FIG. 34 miR-199b-5p+miR4488 combined detection in the sera of melanoma patients is characterized by a significant AUC value of 0.737.

Figure 35:
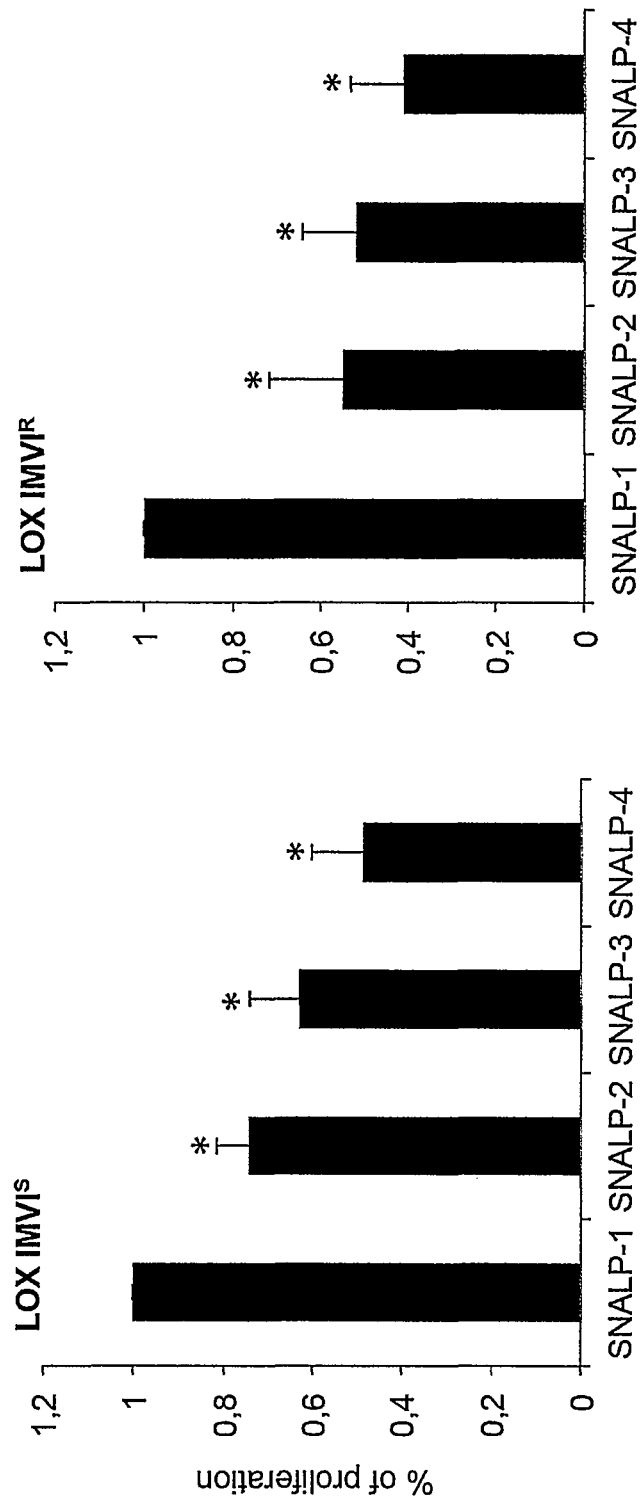

FIG. 35 LOX IMVIS (BRAFi sensitive) and LOX IMVIR (BRAFi-resistant) were exposed to SNALP-1 (Empty), SNALP-2 (miR-204-5p), SNALP-3 (miR-199b-5p) or SNALP-4 (carrying both miRNAs) and cell proliferation was determined with crystal violet and the adsorbance (595 nm) measured with ELISA reader. Data are means±SD. P values were calculated using Student's t-test (significance p<0.05).

Figure 36:
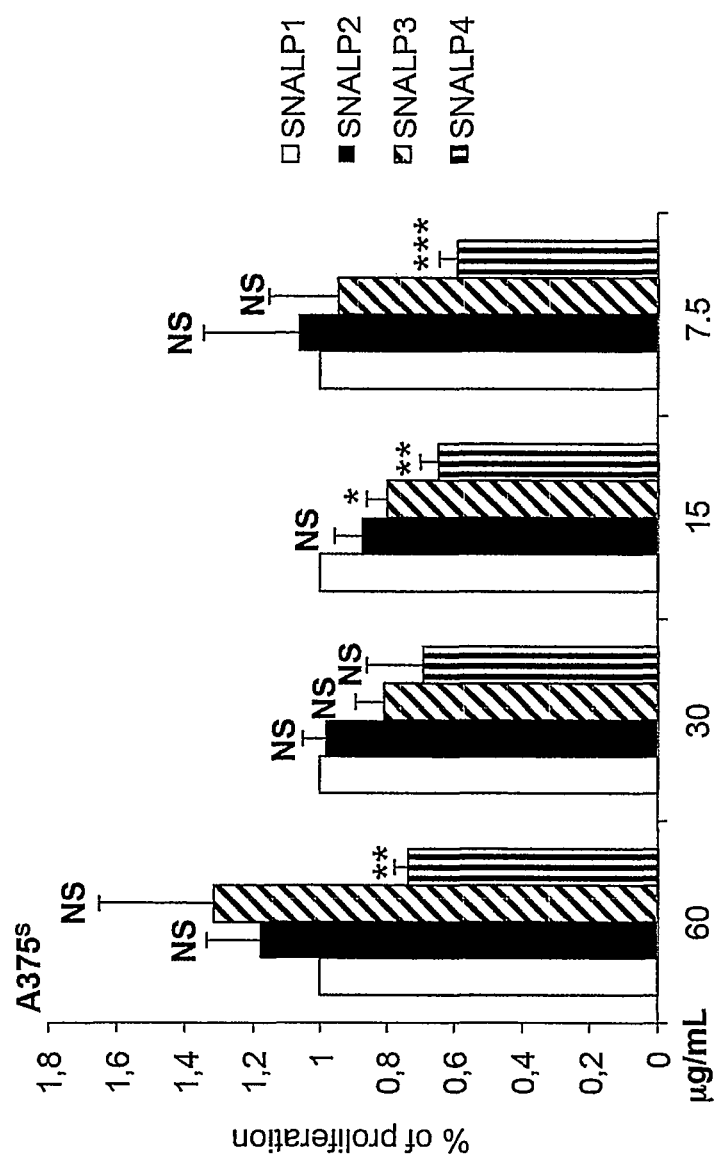

FIG. 36 A375S (BRAFi sensitive) were exposed to different doses of SNALP-1 (Empty), SNALP-2 (miR-204-5p), SNALP-3 (miR-199b-5p) or SNALP-4 (carrying both miR-NAs) and cell proliferation was determined with crystal violet and the adsorbance (595 nm) measured with ELISA reader. Data are means±SD. P values were calculated using Student's t-test (significance p<0.05).

Figure 37:
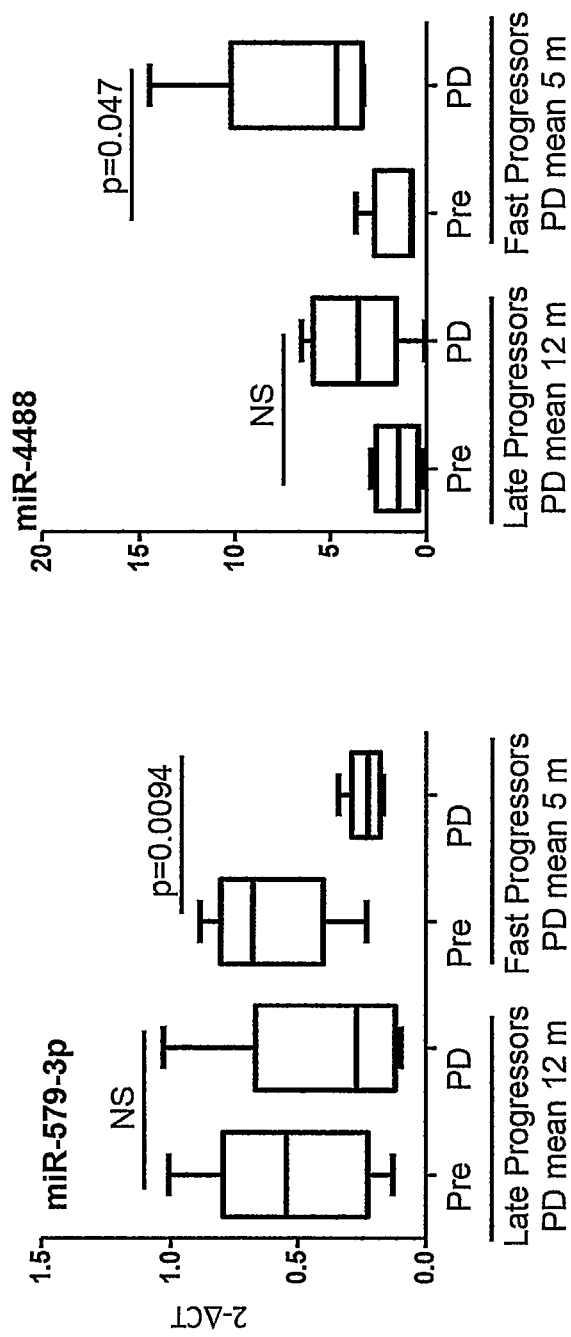

FIG. 37 RNA extracted from plasma samples derived from 10 melanoma patients before initiation of targeted therapy and after progression disease (PD) were subjected to qRT-PCR for the indicated miRNAs. Hence, patients have been clustered in Late Progressors (PD mean 12 months) and Fast Progressors (PD mean 5 months). Results confirm miR-4488 up-regulation and, in contrast, miR-579-3p down-regulation despite their dysregulations occur in statistically significative manner only in Fast Progressors. qRT-PCR results as box-whisker plots; data normalized through Global Mean and Normfinder methods (p<0.05).

DETAILED DESCRIPTION

Example 1: Study of miRNAa Responsible for the Development of Drug Resistance in BRAF Mutated Melanoma Through the Activation of Both Cell Intrinsic and Cell Extrinsic Mechanisms Materials and Methods
Cell Lines
Human melanoma cell lines M14 (ATCC® HTB-129™) and A375 (ATCC® CRL-1619™) (both V600E) were from American Type Culture Collection (ATCC®). LOX IMVI (V600E) melanoma cell line (EZT-LOXI-1) was from EZ Byosistems™. WM266 melanoma cell line (V600D) (WM266-4-01-0001) was from ROCKLAND™ antibodies & assays. Resistant melanoma cells were selected by treating them for about two months with increasing drug concentrations every two weeks (from 50 nM to 2 µM). A375$^{DR}$ cells were selected in the presence of both BRAF and MEK inhibitors, as previously done for M14$^R$, WM266$^R$, LOX IMVI$^R$ and A375$^R$. All human melanoma cell lines used in the present work were cultured in RPMI supplemented with 10% (vol/vol) FBS. Human umbilical vein endothelial cells (HUVEC)s, were employed between the third and the seventh passage, were grown in Eagle Basal Medium (EBM) supplemented with 4% FBS, 0.1% gentamicin, 1 µg/mL hydrocortisone, 10 µg/mL epidermal growth factor and 12 µg/mL bovine brain extract (Cambrex, Bio Science).

Antibodies, Western Blot and Reagents
Antibodies against VEGFA and GAPDH were obtained from Santa Cruz Biotechnology. Vemurafenib and trametinib were obtained from Selleck Chemicals. TaqMan probes for GAPDH, VEGF, BCL2, miR-4443, miR-4488, miR-204-5p, miR-199b-5p, miR-630, miR-1234, is-3676 (previously named miR-3676-3p), miR-145-5p and RNU48 were purchased from Applied Biosystems. Melanoma cells were lysed with RIPA buffer; 50 µg of total protein were resolved under reducing conditions by 8% SDS-PAGE and transferred to reinforced nitrocellulose (BA-S 83, Schleider and Schuell, Keene, N.H., USA). The membranes were blocked with 5% non fat dry milk in PBS 0.1% Tween 20, and incubated with the different primary antibodies. The membranes were rehydrated and probed with anti-GAPDH, to estimate the protein equal loading. Densitometric analysis was performed using Quantity One Program (Bio-Rad Laboratories GmbH) and results were expressed as mean values from three independent experiments.

RNA Extraction and Real-Time PCR Analysis.
RNA was extracted using TRIzol method (Invitrogen) and quantitated by spectrophotometry. Real-time PCR was performed by TaqMan Gene Expression Assays (Applied Biosystems). Circulating Rna from patients' sera was extracted through miRNeasy Mini Kit following the manufacturer's instructions.

Nanostring® Analysis
To perform Nanostring® analysis two melanoma cell lines were exposed to increasing concentrations of a BRAFi for about two months. In each step when the drug doses were increased cells were harvested and total RNA was extracted. For each point of the selection 100 ng of total RNA were hybridized to the array in the nCounter miRNA Expression Assay v1 (NanoString® Technologies, Seattle, Wash., USA) following the manufacturer's instructions. This technology allows direct and digital counting of 800 human miRNAs without amplification reactions. Bioinformatic analysis considers the significantly up- or down-regulated miRNAs with at least two-fold changes as compared to controls.

Target Genes Prediction of miRNAs and Pathway Analysis
Predictions of miRNA complementarity to 3' untranslated regions (UTRs) in mRNAs were performed by using three commonly used tools for target prediction: TargetScanHuman 6.2 (on the World-Wide Web at targetscan.org), PITA, and Miranda (on the World-Wide Web at microrna.org). This analysis was based on searching for the presence of conserved sites that match the seed region of each miRNAs (corresponding to the position of 2-8 nucleotides in a mature miRNAs). In details, the list of the putative targets for each given miRNA was obtained and selected for further functional analysis those predicted from at least two out three tools. Then a functional annotation analysis of pathways by PANTHER was performed.

Cytokinome Evaluation

Levels of cytokines, chemokines, and growth factors were evaluated by the multiplex biometric ELISA-based immunoassay, according to the manufacturer's instructions (Bio-Plex Bio-Rad). In detail, the levels of 27 following cytokines were evaluated in the supernatants of wild type (drug sensitive) M14 and WM266 cell lines and in the respective BRAF inhibitor resistant cells: IL-1β, IL-1ra, IL-2, IL-4, IL-5, IL-6, IL-7, CCL2, CCL11, CXCL10, CXCL8, IFN-γ, IL-9, IL-10, IL-12 (p70), IL-13, IL-15, IL-17, basic FGF, G-CSF, GM-CSF, MIP-1α, MIP-1β, PDGF-ββ, RANTES, TNF-α, and VEGF. Protein levels were quantified using a Bio-Plex array reader (Luminex, Austin, Tex., USA) and a standard curve. A fold change greater than 1.3 was considered significant by evaluating the ratio between the cytokine levels in drug resistant cells compared to drug sensitive cells.

ROC Curves

Receiver operating characteristic (ROC) curves were plotted to estimate the predictive value of four miRNAs, to compute optimal cutoffs for any given feature, to generate performance tables for sensitivity, specificity, and confidence intervals at different cutoffs and to select combinations of features to create biomarker models.

Cell Proliferation Assays and In Vitro Colony Formation Assays

Viability of cells was examined with 3-(4,5-dimethylthiazol-2-yl)-2,5-diphenyltetrazolium bromide Cell Titer 96 AQueous One Solution Cell Proliferation Assay (Promega), according to the manufacturer's protocol. The plates were analyzed in a Multilabel Counter (Bio-Rad Laboratories). Cell viability was also determined by crystal violet staining. Briefly, the cells were stained for 20 min at room temperature with staining solution (0.5% crystal violet in 30% methanol), washed four times with water and then dried. Cells were then dissolved in a Methanol/SDS solution and the adsorbance (595 nm) was read using a microplate ELISA reader.

Tissue Samples

Total RNA was extracted from the FFPE samples from 14 matched tumors from patients before and after the development of resistance to MAPKi, as described in the work by Ma et al. (18). Real-time PCR was assayed as described above. The use of human samples was approved by Istituto Pascale's Ethical Committee with the protocol DSC/2893 on Apr. 11, 2015. All patients signed a general informed consent, which allowed use of this material for research purposes and which was analyzed in an anonymous manner at the Istituto Nazionale per la Cura dei Tumori "Fondazione G. Pascale".

Statistical Analysis

Data from at least three separate experiments are presented as means±SD. P values were calculated using Student's t test and significance level has been defined as $P<0.05$. All experiments shown, except for the ones that involve clinical samples, were performed independently at least three times. Heatmap was evaluated to correlate the expression values of four miRNAs between them by Pearson correlation coefficients. Low and high expression levels are evidenced by black and white colors, respectively. The levels of miR-199b-5p and miR-4488 in melanoma patients' serum were normalized through global mean normalization (GMN) and NormFinder model (19).

Cell Migration Assays

Cell migration was monitored in real time using the xCELLigence Real Time Cell Analysis (RTCA) technology (Acea Bioscience) (20). For these experiments we used CIM-plates which are provided with interdigitated gold microelectrodes on the bottom side of a filter membrane interposed between a lower and an upper compartment. Lower chambers were filled with serum-free medium (CTRL) or undiluted conditioned media from wild type WM266 or resistant WM266 (WM266R) cells. WM266 cells ($2\times10^4$ cells/well) were seeded on filters in serum-free medium. Cell migration was monitored for 12 h, and each experiment was performed at least twice in quadruplicate. Slope represents the change rate of cell index values generated in a 0-6 h time frame.

Tube Formation in a Non-Contact Co-Culture System

Drug sensitive WM266 ($WM266^S$) cells or their BRAFi resistant counterparts ($WM266^R$) were grown to 80% confluence ($1.5\times10^5$ cells/well) on 24 well plates and kept serum free for 18 h prior to the experiment. Growth factor reduced matrigel (100 μl/well) (Becton Dickinson, cat. 356230) was allowed to polymerize for 1 h on a polyester membrane in an intercup chamber. Subsequently, the intercup chamber was introduced in the wells. HUVEC ($2\times10^4$ cells/sample) were seeded on matrigel at 37° C., 5% CO2 for 4 h.

Tube Formation Assay

Growth factor reduced Matrigel (10 μL/well) was allowed to polymerize for 1 h on angiogenesis 96 well μ-plates (ibidi, GmbH) at 37° C., 5% CO2. HUVEC ($5\times10^3$ cells/well) suspended in 50 μL of pre-warmed Eagle Basal Medium (CTRL), 10% FBS, or conditioned media from $WM266^S$, or $WM266^R$ cells, were seeded on matrigel and allowed to form tubes at 37° C. in humidified air with 5% CO2 for 6 h. In order to quantify tube formation, images were acquired and the number of tubes formed by cord-like structures exceeding 100 μm in length were visualized using Axiovision 4.8 software (Carl Zeiss) and counted.

Results

Significant Changes in Whole miRNome Expression Take Place During Evolution of Drug Resistance to BRAF Inhibitors in Human Melanoma.

In order to address this question the "road to resistance" approach depicted in FIG. 1 has been followed. Two human BRAF mutated and drug sensitive cell lines bearing different BRAF gene mutations (V600D-M14-vs V600E-WM266-) were exposed to increasing drug concentrations (from 50 nM to 2 μM every two weeks for a total period of 2 months). At each stepwise drug increase total RNA was extracted and subjected to total miRNome profiling using the Nanostring® platform (nCounter Human v1) analysis (FIG. 1). This technology allows direct and digital counting of 800 human miRNAs without amplification reactions. Bioinformatic analysis of the results allowed the identification of miRNAs significantly up- or down-regulated with at least two-fold changes as compared to controls. The results, depicted as Venn Diagrams in FIG. 2, show that each selection step is characterized by a distinct set of miRNAs expression changes, with a shared set of miRNAs deregulated between the different selection steps. Of note, only three miRNAs in M14 and only one miRNA in WM266 resulted constantly deregulated throughout all selection steps. The most relevant finding was the progressive deregulation (up or down) of a growing number of miRNAs during the selection process. At the highest drug concentration (i.e. 1 uM and 2 uM BRAFi), 118 and 97 miRNAs (>14% and >12% of total miRNAs analyzed) in WM266 whereas 70 and 68 miRNAs (approaching 8% in both cases of miRNAs analyzed) in M14 were deregulated as compared to the starting sensitive cells (the entire list of statistically significant deregulated miRNAs is reported in the Table 1 below).

TABLE 1

| BRAFi nM | 1 microM | 2 microM |
|---|---|---|
| M14 | miR-18a-5p (MIMAT0000072), miR-24-3p (MIMAT0000080), miR-204-5p (MIMAT0000265), miR-652-3p (MIMAT0003322), miR-197-3p (MIMAT0000227), miR-92a-3p (MIMAT0000092), miR-15b-5p (MIMAT0000417), miR-19a-3p (MIMAT0000073), miR-221-3p (MIMAT0000278), miR-584-5p (MIMAT0003249), miR-107 (MI0000114), miR-106a-5p(MIMAT0000103) +miR-17-5p (MIMAT0000070), miR-3676-3p (removed from miRBase 20), miR-363-3p (MIMAT0000707), miR-18b-5p (MIMAT0001412), miR-19b-3p (MIMAT0000074), miR-182-5p (MIMAT0000259), miR-455-3p (MIMAT0004784), miR-96-5p (MIMAT0000095), miR-3127-5p (MIMAT0014990), miR-135b-5p (MIMAT0000758), miR-208a (MI0000251), miR-514a-3p (MIMAT0002883), miR-518e-3p (MIMAT0002861), miR-604 (MI0003617), miR-320d (MI0008190), miR-573 (MI0003580), miR-506-3p (MIMAT0002878), miR-432-5p (MIMAT0002814), miR-4516 (MI0016882), miR-4286 (MI0015894), miR-4532 (removed from miRBase 20), miR-1273f (removed from miRBase 20), miR-4792 (removed from miRBase 20), miR-1273e (removed from miRBase 20), miR-320e (MI0014234), miR-548w (MI0014222), miR-542-5p (MIMAT0003340), miR-143-3p (MIMAT0000435), miR-143-3p (MIMAT0000435), miR-508-3p (MIMAT0002880), miR-575 (MI0003582), miR-509-3p (MIMAT0002881), miR-433 (MI0001723), miR-1278 (MI0006425), miR-874 (MI0005532), miR-152 (MI0000462), miR-619 (MI0003633), miR-548i (MI0006421), miR-1245a (MI0006380), miR-300 (MI0005525), miR-21-5p (MIMAT0000076), miR-630 (MI0003644), miR-514b-3p (MIMAT0015088), miR-596 (MI0003608), miR-582-5p (MIMAT0003247), miR-513c-5p (MIMAT0005789), miR-513b (MI0006648), miR-617 (MI0003631), miR-1302 (MI0006362), miR-1976 (MI0009986), miR-544b (MI0014159), miR-10b-5p (MIMAT0000254), miR-4488 (MI0016849), miR-1915-3p (MIMAT0007892), miR-143-3p (MIMAT0000435), miR-1246 (MI0006381), | miR-4443 (MI0016786), miR-204-5p (MIMAT0000265), miR-372 (MI0000780), miR-766-3p (MIMAT0003888), miR-493-3p (MIMAT0003161), miR-576-5p (MIMAT0003241), miR-1301 (MI0003815), miR-512-3p (MIMAT0002823), miR-455-3p (MIMAT0004784), miR-485-3p (MIMAT0002176), miR-767-3p (MIMAT0003883), miR-378b (MI0014154), miR-1972 (MI0009982), miR-199b-3p (MIMAT0004563), miR-652-3p (MIMAT0003322), miR-513a-3p (MIMAT0004777), miR-539-5p (MIMAT0003163), miR-892a (MI0005528), miR-339-3p (MIMAT0004702), miR-18a-5p (MIMAT0000072), miR-551b-3p (MIMAT0003233), miR-142-5p (MIMAT0000433), miR-217 (MI0000293), miR-1245b-5p (MIMAT0019950), miR-761 (MI0003941), miR-1255b-5p (MIMAT0005945), miR-486-3p (MIMAT0004762), miR-335-5p (MIMAT0000765), miR-4431 (MI0016771), miR-302f (MI0006418), miR-1908 (MI0008329), miR-548am-3p (MIMAT0019076), miR-758 (MI0003757), miR-526a (MI0003157 )+miR-520c-5p (MIMAT0005455)+miR-518d-5p (MIMAT0005456), miR-369-3p (MIMAT0000721), miR-520b (MI0003155), miR-141-3p (MIMAT0000432), miR-588 (MI0003597), miR-487a (MI0002471), miR-548d-5p (MIMAT0004812), miR-455-5p (MIMAT0003150), miR-1261 (MI0006396), miR-770-5p (MIMAT0003948), miR-1225-5p (MIMAT0005572), miR-367-3p (MIMAT0000719), miR-145-5p (MIMAT0000437), miR-21-5p (MIMAT0000076), miR-593-3p (MIMAT0004802), miR-194-5p (MIMAT0000460), miR-187-3p (MIMAT0000262), miR-432-5p (MIMAT0002814), miR-542-5p (MIMAT0003340), miR-877-5p (MIMAT0004949), miR-596 (MI0003608), miR-4532 (removed from miRBase 20), miR-10b-5p (MIMAT0000254), miR-3195 (MI0014240), miR-1302 (MI0006362), miR-1268a (MI0006405), miR-874 (MI0005532), miR-4516 (MI0016882), miR-582-5p (MIMAT0003247), miR-143-3p (MIMAT0000435), miR-4488 (MI0016849), miR-1915-3p (MIMAT0007892), miR-1253 (MI0006387), miR-1246 (MI0006381), miR-1234 (MI0006324) |

TABLE 1-continued

| BRAFi nM | 1 microM | 2 microM |
|---|---|---|
| | miR-1234 (MI0006324), miR-4443 (MI0016786), miR-1253 (MI0006387) | |
| WM266 | miR-34a-5p (MIMAT0000255), miR-199b-5p (MIMAT0000263), miR-221-3p (MIMAT0000278), miR-100-5p (MIMAT0000098), miR-204-5p (MIMAT0000265), miR-15a-5p (MIMAT0000068), miR-107 (MI0000114), miR-196b-5p (MIMAT0001080), miR-130a-3p (MIMAT0000425), miR-4454 (MI0016800), miR-720 (removed from miRBase 20), miR-16-5p (MIMAT0000069), miR-196a-5p (MIMAT0000226), miR-548aa (MI0016689), miR-582-5p (MIMAT0003247), miR-27b-3p (MIMAT0000419), miR-4455 (MI0016801), miR-18a-5p (MIMAT0000072), miR-3147 (MI0014173), miR-551b-3p (MIMAT0003233), miR-1178 (MI0006271), miR-15b-5p (MIMAT0000417), miR-507 (MI0003194), miR-3676-3p (removed from miRBase 20), miR-548f (MI0006374), miR-301a-3p (MIMAT0000688), miR-10b-5p (MIMAT0000254), miR-320e (MI0014234), miR-424-5p (MIMAT0001341), miR-148b-3p (MIMAT0000759), miR-125b-5p (MIMAT0000423), miR-181b-5p (MIMAT0000257)+miR-181d (MI0003139), miR-210 (MI0000286), miR-764 (MI0003944), miR-873-5p (MIMAT0004953), miR-708-5p (MIMAT0004926), miR-145-5p (MIMAT0000437), miR-1470 (MI0007075), miR-199a-3p (MIMAT0000232)+miR-199b-3p (MIMAT0004563), miR-148a-3p (MIMAT0000243), miR-455-3p (MIMAT0004784), miR-548am-3p (MIMAT0019076), miR-548al (MI0016851), miR-1290 (MI0006352), miR-656 (MI0003678), miR-150-5p (MIMAT0000451), miR-206 (MI0000490), miR-374b-5p (MIMAT0004955), miR-126-3p (MIMAT0000445), miR-920 (MI0005712), miR-562 (MI0003568), miR-3127-5p (MIMAT0014990), miR-188-5p (MIMAT0000457), miR-1251 (MI0006386), miR-125a-5p (MIMAT0000443), miR-645 (MI0003660), miR-1183 (MI0006276), miR-512-3p (MIMAT0002823), miR-217 (MI0000293), miR-135b-5p (MIMAT0000758), miR-369-3p (MIMAT0000721), miR-1258 (MI0006392), miR-222-3p (MIMAT0000279), miR-1248 (MI0006383), miR-2115-5p (MIMAT0011158), miR-493-3p (MIMAT0003161), miR-23a-3p (MIMAT0000078), miR-618 (MI0003632), miR-92a-3p (MIMAT0000092), miR-634 (MI0003649), miR-637 (MI0003652), | miR-34a-5p (MIMAT0000255), miR-199b-5p (MIMAT0000263), miR-204-5p (MIMAT0000265), miR-196b-5p (MIMAT0001080), miR-221-3p (MIMAT0000278), miR-551b-3p (MIMAT0003233), miR-130a-3p (MIMAT0000425), miR-145-5p (MIMAT0000437), miR-107 (MI0000114), miR-548aa (MI0016689), miR-100-5p (MIMAT0000098), miR-720 (removed from miRBase 20), miR-27b-3p (MIMAT0000419), miR-15a-5p (MIMAT0000068), miR-301a-3p (MIMAT0000688), miR-582-5p (MIMAT0003247), miR-196a-5p (MIMAT0000226), miR-211-5p (MIMAT0000268), miR-199a-3p (MIMAT0000232)+miR-199b-3p (MIMAT0004563), miR-4454 (MI0016800), miR-148a-3p (MIMAT0000243), miR-708-5p (MIMAT0004926), miR-455-3p (MIMAT0004784), miR-143-3p (MIMAT0000435), miR-320e (MI0014234), miR-4455 (MI0016801), miR-1253 (MI0006387), miR-152 (MI0000462), miR-3147 (MI0014173), miR-148b-3p (MIMAT0000759), miR-3676-3p (removed from miRBase 20), miR-10b-5p (MIMAT0000254), miR-519e-3p (MIMAT0002829), miR-520g (MI0003166), miR-338-3p (MIMAT0000763), miR-125b-5p (MIMAT0000423), miR-1178 (MI0006271), miR-507 (MI0003194), miR-1280 (removed from miRBase 20), miR-1266 MI0006403), miR-18a-5p (MIMAT0000072), miR-1258 (MI0006392), miR-520d-3p (MIMAT0002856), miR-144-3p (MIMAT0000436), miR-197-3p (MIMAT0000227), miR-518e-3p (MIMAT0002861), miR-920 (MI0005712), miR-548al (MI0016851), miR-640 (MI0003655), miR-625-5p (MIMAT0003294), miR-639 (MI0003654), miR-1183 (MI0006276), miR-526b-5p (MIMAT0002835), miR-770-5p (MIMAT0003948), miR-125a-5p (MIMAT0000443), miR-580 (MI0003587), miR-135b-5p (MIMAT0000758), miR-342-3p (MIMAT0000753), miR-4508 (MI0016872), miR-4485 (MI0016846), miR-628-5p (MIMAT0004809), miR-126-3p (MIMAT0000445), miR-192-5p (MIMAT0000222), miR-3178 (MI0014212), miR-326 (MI0000808), miR-1182 (MI0006275), miR-151b (MI0003772), miR-4488 (MI0016849), miR-132-3p (MIMAT0000426), miR-761 (MI0003941), miR-185-5p (MIMAT0000455), |

TABLE 1-continued

| BRAFi nM | 1 microM | 2 microM |
|---|---|---|
| | miR-625-5p (MIMAT0003294), | miR-374a-5p (MIMAT0000727), |
| | miR-892a (MI0005528), | miR-222-3p (MIMAT0000279), |
| | miR-518b (MI0003156), | miR-1207-3p (MIMAT0005872), |
| | miR-581 (MI0003588), | miR-34c-3p (MIMAT0004677), |
| | miR-1245b-3p (MIMAT0019951), | miR-518b (MI0003156), |
| | miR-655 (MI0003677), | miR-374b-5p (MIMAT0004955), |
| | miR-3182 (MI0014224), | miR-630 (MI0003644), |
| | miR-339-3p (MIMAT0004702), | miR-361-3p (MIMAT0004682), |
| | miR-132-3p (MIMAT0000426), | miR-598 (MI0003610), |
| | miR-326 (MI0000808), | miR-23a-3p (MIMAT0000078), |
| | miR-1229 (MI0006319), | let-7g-5p (MIMAT0000414), |
| | miR-429 (MI0001641), | miR-663b (MI0006336), |
| | miR-598 (MI0003610), | miR-649 (MI0003664), |
| | miR-192-5p (MIMAT0000222), | miR-26b-5p (MIMAT0000083), |
| | miR-215 (MI0000291), | let-7d-5p (MIMAT0000065), |
| | miR-4488 (MI0016849), | miR-378a-3p (MIMAT0000732)+miR-378i (MI0016902), |
| | miR-640 (MI0003655), | |
| | miR-1207-3p (MIMAT0005872), | miR-32-5p (MIMAT0000090), |
| | miR-378a-3p (MIMAT0000732)+miR-378i (MI0016902), | miR-378g (MI0016761), |
| | | miR-96-5p (MIMAT0000095), |
| | miR-1915-3p (MIMAT0007892), | miR-194-5p (MIMAT0000460), |
| | miR-649 (MIMAT0003319), | miR-182-5p (MIMAT0000259), |
| | miR-580 (MI0003587), | miR-363-3p (MIMAT0000707), |
| | miR-34c-3p (MIMAT0004677), | miR-1234 (MI0006324), |
| | miR-1973 (MI0009983), | let-7f-5p (MIMAT0000067), |
| | miR-663b (MI0006336), | miR-4443 (MI0016786), |
| | miR-32-5p (MIMAT0000090), | miR-9-5p (MIMAT0000441) |
| | miR-520a-3p (MIMAT0002834), | |
| | let-7g-5p (MIMAT0000414), | |
| | miR-1182 (MI0006275), | |
| | miR-363-3p (MIMAT0000707), | |
| | miR-361-3p (MIMAT0004682), | |
| | miR-575 (MI0003582), | |
| | miR-342-3p (MIMAT0000753), | |
| | let-7d-5p (MIMAT0000065), | |
| | miR-26b-5p (MIMAT0000083), | |
| | miR-4508 (MI0016872), | |
| | miR-1234 (MI0006324), | |
| | miR-96-5p (MIMAT0000095), | |
| | miR-378g (MI0016761), | |
| | miR-194-5p (MIMAT0000460), | |
| | miR-4443 (MI0016786), | |
| | miR-182-5p (MIMAT0000259), | |
| | miR-4286 (MI0015894), | |
| | let-7f-5p (MIMAT0000067), | |
| | miR-4485 (MI0016846), | |
| | miR-630 (MI0003644), | |
| | miR-9-5p (MIMAT0000441) | |

This finding underscores a major rewiring of the entire miRNome population in fully resistant vs sensitive cells.

To confirm this finding, Principal Component Analysis (PCA) of Nanostring data was carried out. The results (FIG. 3, every dot represents cell populations at a given drug dose), confirmed that changes of the entire miRNome expression (n=800 miRNAs) are able to distinguish different drug sensitivity states. In particular, it is possible to separate fully sensitive cells (untreated or untreated plus 50 nM depending upon cell line) vs mildly resistant (100-200 nM drug) vs strongly resistant (1-2 μM) based on the global pattern of miRNAs expression. Overall this shows that the miRnome of highly resistant cells is significantly different from that of the drug sensitive cells and that it is possible to detect changes in different states of drug sensitivity by measuring miRNA expression levels.

Given the high degree of heterogeneity of melanomas, further studies were focused on a subset of commonly deregulated miRNAs in both cell lines. Data, schematically shown as Venn Diagrams in FIG. 4, indicate also in this case that the highest steps of selection (i.e. 1 μM and 2 μM BRAFi), correspond to the highest number of commonly deregulated miRNAs (n=38 in total). The entire list of miRNAs, commonly deregulated between M14 and WM266 is reported in Table 2.

TABLE 2

| BRAF (nM) | 50 | 200 | 500 | 1000 | 2000 |
|---|---|---|---|---|---|
| Common Deregulated miRNAs | miR-4443 | miR-124, miR-134, miR-143-3p, miR-204-5p, miR-224-5p, | miR-143-3p, miR-512-3p, miR-518e-3p, miR-611, miR-1253, | miR-10b-5p, miR-15b-5p, miR-18a-5p, miR-92a-3p, miR-96-5p, | miR-10b-5p, miR-18a-5p, miR-1234, miR-143-3p, miR-145-5p, |

TABLE 2-continued

| BRAF (nM) 50 | 200 | 500 | 1000 | 2000 |
|---|---|---|---|---|
| | miR-300, miR-519b-3p, miR-548ag, miR-720, miR-1253, miR-1289, miR-3147, miR-4454 | miR-4443 | miR-107, miR-135b-5p, miR-182-5p, miR-204-5p, miR-221-3p, miR-320e, miR-363-3p, miR-455-3p, miR-575, miR-582-5p, miR-630, miR-1234, miR-1915-3p, miR-3127-5p, miR-3676-3p, miR-4286, miR-4443, miR-4488 | miR-199b-5p, miR-204-5p, miR-455-3p, miR-551b-3p, miR-582-5p, miR-761, miR-770-5p, miR-1253, miR-4443, miR-4488 |

An analysis of the predicted molecular targets of the commonly deregulated miRNAs was performed. To this purpose, three available prediction algorithms, TargetScan-Human 6.2, PITA and Miranda, were used and only target genes predicted by at least two out of the three algorithms were considered. The resulting gene list was used for a functional annotation analysis of pathways using the PANTHER software. Of notice, the number of pathways affected by commonly deregulated miRNAs between the two cell lines is relatively low at low drug concentrations up to 500 nM but dramatically increases at the highest drug exposures of 1 and 2 µM respectively (FIG. 5). In particular, at the dose of 2 µM 176 predicted targets of commonly deregulated miRNAs between the two cell lines (see Table 3) were identified. Among them both known oncogenes such as BCL2, MDM4 and KRAS targeted by down-regulated miRNAs and oncosuppressor geneses, such as MAPK13, NCOR2 and BAX, targeted by up-regulated miRNAs were found. However, besides the involvement of intracellular pathways responsible for cell intrinsic growth deregulation such as MAPK, AKT, Wnt signaling and cell cycle/apoptosis, a prominent involvement was observed for pathways responsible for cancer cell extrinsic deregulation of pro-angiogenic and pro-inflammatory phenotypes (FIG. 7). These findings are of great interest since perturbation of the tumor microenvironment could constitute a hallmark of melanoma drug resistance (21).

TABLE 3

Predicted targets of commonly deregulated miRNAs at the dose of 2 µM (M14 and WM266)

MAPK13, DAB2IP, EDN3, CISH, NCOR2, TOLLIP, XDH, PLCB2, ADRA2B, VAMP2, STX6, PHC2, ABAT, SCML4, PIK3C2B, EPHB1, PRKD3, MAP3K1, PDGFB, KRAS, F3, JUN, PIK3R1, NOTCH2, NOTCH1, PAK2, ADRBK2, AGTR1, GNAQ, GNB5, ARRB1, ZNF12, BAX, MAP2K3, BCL2, MCL1, BCL2L11, BAG1, BAG3, CASP10, CREB1, BCL2L1, CAD, CD6, ABL1, ENAH, NFATC4, VAV1, PLAT, PLAU, THBD, THRB, F8, GP5, PCDH9, FZD10, PCDH1, FZD4, FBXO44, CDH16, FBXO2, CSNK2A1, TCF7L1, GNG2, CAMKK1, IER3, ADCY1, EIF4E, PTK2B, TACR1, TCF4, CSNK1A1, CCNE2, PSME3, CLOCK, RHOU, SSH2, AK2, AK1, RRM2B, XRN1, YWHAG, CBL, YWHAH, SPRY1, PPP2R5E, TGFA, RHOQ, PPP2CB, YWHAQ, SEC11C, EDNRA, PRKY, LMNB2, PARP3, FGFR3, FGF7, PPP2R2A, FGFR2, HK2, EARS2, COX10, ALAD, RGS6, SSR1, CLTCL1, CLTC, ADORA1, RGS5, KCNJ9, PHKB, PLCD4, VHL, EGLN2, IL10RB, CCL3, COL6A1, PTAFR, CXC3CR1, CAMK2A, SOCS6, COL6A6, IGF1, RPS6KA4, COL11A1, ITGA3, COL5A1, SOCS3, IL16, CDKN1A, MKNK2, LIAS, NAT10, HEYL,

TABLE 3-continued

Predicted targets of commonly deregulated miRNAs at the dose of 2 µM (M14 and WM266)

PSEN1, HEY1, POFUT1, EEF2K, VAMP8, CACNA1C, PML, SUMO1, HDAC2, SIRT1, PERP, HMGB, STARD8, ERG, ELF5, PKN2, ELF3, ME1, STXBP1, SYN2, HLA-DOA, CD80, CD3E, ACVR2B, TLL2, SMAD2, ACVR1B, BMPR1A, BMP6, TIRAP, TNFAIP3, PSMD8, UBE2L6, WWP2, PPARD, CSNK1g2, TTBK2, KREMEN2, BCL9, LRP6, TLE4, NKD1.

Next, Nanostring® data were validated by Real Time-PCR (qRT-PCR) on a subset of deregulated miRNAs. To this purpose a total of four matched BRAF sensitive vs drug resistant cell lines, namely both the initial M14 and WM266 cells, and LOX IMVI and A375) were used. Again, resistant cells were selected for two months in the presence of increasing concentrations of a BRAFi and RNA was extracted at each step. Four miRNAs were chosen: two up-regulated (miR-4443 and miR-4488, called also UPMIR-NAs) and two down-regulated (miR-204-5p and miR-199b-5p, called also DOWNMIRNAs) in the initial Nanostring® study at the highest drug concentrations.

Results (FIG. 7, 8, 9, 10) confirm that miR-4443 and miR-4488 are strongly increased in all four BRAFi-resistant melanoma cell lines tested whereas miR-204-5p and miR-199b-5p are significantly down-regulated in the same conditions. These data strongly suggest that miR-4443 and miR-4488 could act as facilitators of melanoma drug resistance, while miR-204-5p and miR-199b-5p could antagonize drug resistance. Furthermore, it is important to point out that Nanostring® data of at least other 4 miRNAs (FIG. 11) were validated in M14 and WM266 melanoma cells. Hence, in summary qRT-PCR data showed excellent agreement with Nanostring® analysis, validating the magnitude and the directionality observed for the deregulation of most miR-NAs. Interestingly, among them, miR-3676-3p, originally described as a miRNA, but recently demonstrated to belong to a new class of small noncoding RNAs, tRNA-derived small RNAs (tsRNAs) (22) was also identified and validated.

Deregulated miRNAs Identified by Whole miRNAome Analysis of Drug Resistant Melanoma Cells Potently Affect Drug Sensitivity.

Next, the biological consequences of overexpressing or inhibiting the expression of the four selected miRNAs above miR-4443, miR-4488, miR-204-5p and miR-199b-5p were assessed by transient transfections in sensitive M14 and WM266 melanoma cells in the presence or not of a BRAFi in order to evaluate melanoma cell proliferation and apoptosis induction. Results show that enforced expression of the two UPMIRNAs (miR-4443 and miR-4488) decreases the effect of BRAFi on cell viability (FIG. 12) and induction of apoptosis, measured by Caspase 3/7 activation (FIG. 13). On the opposite, enforced expression of the two DOWNMIR-NAs (miR-204-5p and miR-199b-5p) not only inhibits cell proliferation and induces apoptosis but also potentiates BRAFi activity (FIGS. 12 and 13).

Furthermore, the effect of inhibiting UPMIRNAs expression by transient transfection of their respective antagomiRs in both drug sensitive and resistant M14 cells was evaluated by in vitro short term colony formation assays. Data quantification (FIG. 14) clearly shows that the inhibition of these oncogenic miRNAs was able to strongly reduce colony formation. Likewise using the same assay overexpression of both miR-204-5p and miR-199b-5p strongly impaired colony formation in BRAFi drug resistant cells (FIG. 15).

Hereafter, the effects of the DOWNMIRNAs on the development of drug resistance in vitro were determined. Hence, miR-199b-5p as representative oncosuppressive miRNA was overexpressed in M14$^S$ melanoma cells exposed chronically to a BRAFi for 28 days. Data, shown in FIG. 16, demonstrated that melanoma cells where miR-199b-5p was overexpressed completely lost the ability to form BRAFi-resistant colonies. In contrast, growth of control cells transfected with scrambled-miRNA was initially impaired by the presence of a BRAF inhibitor (from 7 to 21 days of drug exposure), but gave rise to resistant colonies at later times (day 28) (FIG. 16).

Next, the growth inhibitory effect of simultaneously targeting miRNAs combinations was determined. In detail, for these experiments antagomiRs recognising the UPMIRNAs (amiR-4443: aaaacccacgcctccaa (SEQ ID NO: 10) and amiR-4488: cgccggagcccgccccct (SEQ ID NO: 11)) in different combinations with DOWNMIRNAs mimics (miR-204-5p: uucccuuugucauccuaugccu (SEQ ID NO: 2) and miR-199b-5p cccaguguuuagacuaucuguuc (SEQ ID NO: 1)) were transiently transfected in melanoma cell lines. Results, shown in FIG. 17, demonstrate that all the combinations tested (miR-199b-5p+amiR-4443; miR-204-5p+amiR-4443; miR-204-5p+miR-199b-5p; miR-199b-5p+amiR-4488; miR-204-5p+amiR-4488; amiR-4443+amiR-4488) are able to strongly reduce M1 RR melanoma cell growth as compared to single treatments. In addition, the effect of targeting miRNAs individually or in combinations was assessed in a cell line rendered double resistant to both BRAF and MEK inhibitors (called A375$^{DR}$). Other investigators have previously reported that double drug resistant melanoma cell lines are more difficult to growth inhibit (5). In fact no growth inhibition was observed effect on A375$^{DR}$ when the four selected miRNAs were targeted individually (FIG. 18, left panel). In contrast, the simultaneous transfection of the two DOWNMIRNAs mimics results in a strong inhibition of A375$^{DR}$ melanoma cell growth (FIG. 18, right panel). Finally, when both these DOWNMIRNAs were combined with the previously identified oncosuppressive miRNA, miR-579-3p, a stronger inhibitory effect on A375$^{DR}$ cell growth compared to double treatments was observed (FIG. 19). These data demonstrate that in order to inhibit growth of double drug resistant melanomas it is necessary to deliver combinations of selected miRNAs.

Drug Resistant Melanoma Cells Overproduce a Wide Array of Pro-Inflammatory and Pro-Angiogenic Factors.

As reported above bioinformatic analysis of the predicted molecular targets of the commonly deregulated miRNAs in BRAF inhibitor resistant cells highlighted a prominent involvement of targets responsible for the activation of pro-angiogenic and pro-inflammatory pathways. In order to validate these predictions the cytokinome profile of drug resistant WM266 and M14 melanoma cells was compared to that of their drug sensitive counterparts. To this purpose, as depicted in FIG. 20, the levels of 27 cytokines were determined in cell-derived supernatants. Both in M14 (FIG. 21) and, more pronounced (up to several-hundred folds) in WM266 (FIG. 22), a statistically significant (fold change significance greater than 1.3) increased secretion of a wide range of cytokines and chemokines was observed in drug resistant vs drug sensitive cells. For each cell line was it possible to divide up-regulated cytokines and chemokines in three distinct groups with a high, medium and low degree of upregulation respectively.

In summary it was observed that: i) eleven interleukins (IL-1β, IL-1ra, IL-4, IL-5, IL-6, IL-7, IL-8, IL-9, IL-10, IL-12 and IL-13), four chemokines (Eotaxin, IP-10, RANTES and MIP-1α), three growth factors (G-CSF, PDGF-ββ, and VEGF), and the proinflammatory cytokines IFN-γ and TNF-α were overexpressed in both resistant melanoma cells as compared to their sensitive counterparts; ii) MCP-1, was up-regulated only in M14 drug resistant cells; iii) two interleukins (IL-15 and IL-17), the growth factor bFGF and the chemokine MIP-1, were up-regulated only in WM266 resistant cells.

Since several of the upregulated chemokines, cytokines and growth factors are involved in cell migration and metastasis, the capability of cell media from drug sensitive vs resistant WM266 to elicit melanoma cell migration was determined. Briefly, WM266 cells were seeded on the bottom of a filter membrane, in which interdigitated gold microelectrodes were located (13) interposed between a lower and an upper compartment in contact with serum-free medium (CTRL), conditioned media from WM266$^S$ or WM266$^R$ melanoma cells. Thereafter, cell migration was measured in real time for 12 hours through the measurement of the impedance-based detection of electrode surface occupation. Results, expressed as Cell Index and Slope induction showed that conditioned media from WM266$^R$ melanoma cells was able to strongly induce cell migration as compared to cell media from sensitive counterparts and CTRL media (FIG. 23, right and left panels).

Downmodulation of miR-199b-5p in Drug Resistant Melanoma Cells is Responsible for Increased VEGF Release and Acquisition of a Pro-Angiogenic Status.

VEGF was one of the most upregulated factors intercepted by the cytokinome analysis of drug resistant melanoma cells. This finding was of particular interest in the light of the known involvement of VEGF in melanoma progression and resistance to therapy (23). Hence the pro-angiogenic potential of the conditioned media (CM) of drug sensitive vs drug resistant WM266 cells to induce endothelial tube formation on human umbilical vein endothelial cells (HUVEC) plated on matrigel was tested; the appearance of tubular branches was measured after 6 h. Of note, for our results only tube-like structures exceeding 100 μm in length were considered. As shown in FIG. 25, the CM from WM266$^R$ triggered a strong endothelial tube formation, whereas conditioned medium from WM266$^S$ was inactive in this assay. As control, 10% FBS employed as a source of angiogenic growth factors, elicited a considerable response rising to 204% over basal (FIG. 24). To further confirm VEGF involvement, VEGFR activity was specifically inhibited with Avastin or Pazopanib (24). Results, reported in FIG. 26, confirmed that tube formation induced by CM from WM266$^R$ melanoma cells was as efficient as recombinant VEGF and was significantly inhibited by the addition of either drug (FIG. 25). In order to find a correlation between miRNAs deregulation and VEGF increased expression and release members of miR-199 family were considered (25). Of notice, one of the most downregulated miRNA emerging from the Nanostring® analysis of drug resistant cells was miR-199b-5p. Therefore, miR-199b-5p was overexpressed in WM266$^R$ cells. In order to assess whether this miRNA was able to reduce specifically VEGF expression, Western Blot analysis was performed. Results (FIG. 26) showed that this was indeed the case. Finally, the CM from WM266$^R$ cells transfected with miR-199b-5p lost the capability to induce tube formation (FIG. 27).

All together these findings support the notion that BRAFi resistant melanoma cells are able to sustain pro-angiogenic stimuli through the increased release of VEGF, caused by down-regulation of the oncosuppressive miR-199b-5p.

Specific miRNAs Signatures Characterize the Acquisition of Drug Resistance to Target Therapy.

The observations above suggest that measuring changes in the expression of selected miRNAs could be used as an approach to identify BRAF mutated melanoma patients ab initio or de novo resistant to therapy with inhibitors of the MAPK pathway.

Since miRNAs are very stable in formalin-fixed paraffin embedded (FFPE) samples (11) total RNA from 14 matched tumour samples (before initiation of targeted therapy and after tumour progression from the same patients) was extracted and subjected to qRT-PCR to determine the expression levels of mir-4443, miR-4488, miR-204b-5p and miR-199b-5p (FIG. 28). Results, shown as box-whisker plots, confirm in tumour samples previous results obtained in drug resistant vs sensitive cell lines: miR-204-5p and miR-199b-5p are strongly down-regulated in MAPKi-resistant tumours, whereas in contrast miR-4443 and miR-4488 are strongly up-regulated (FIG. 29).

Moreover, the correlation index of the two DOWNMIRNAs and of the two UPMIRNAs was assessed as a heatmap, through the measure of Pearson correlation coefficients. miR-199b-5p and miR-204-5p were found to be correlated with each other (identified by white squares in FIG. 30) and anti-correlated to up-regulated miRNAs (see black squares in FIG. 31). In contrast, miR-4443 and miR-4488 were found to have the opposite correlation.

A challenging issue is the development of powerful diagnostic tools able to predict patients' response to drugs. In this context, miRNAs could represent suitable candidates for the development of a non-invasive and reproducible diagnostic tool for their great stability in several human fluids (26). Hence, the diagnostic potential of the four identified up-or down-regulated miRNAs was assessed. Their expression levels before therapy and after tumour progression were used to construct receiver operating characteristic (ROC) curves in order to estimate the predictive value of their deregulation as a marker of drug resistance. Sensitivity, specificity and accuracy of classifier was evaluated together by means of the Area Under Curve (AUC). Of importance, the two DONWMIRNAS, miR-199b-5p and miR-204-5p, yielded an area under the curve (AUC) of 0.929 and 0.786, with sensitivity reaching 100% and cut-off values of 0.897 and 0.909, respectively (FIG. 32, upper panels). On the other hand, two UPMIRNAs, miR-4488 and miR-4443, yielded an AUC of 0.857 with sensitivity reaching 100% and cut-off values of 1.1 and 1.09, respectively (FIG. 31, lower panels).

Thereafter, the predictive value of changes in the expression of combinations of miRNAs was measured as diagnostic measure. Again, ROC curves were plotted for the best combinations of the four miRNAs and a 95% of power at a significance level of 0.05 was considered to detect a value of AUC of 0.75 as significant with respect to the null hypothesis value of 0.50.

Interestingly, as shown in FIG. 32 significant AUC values were obtained for several combinations: miR-199b-5p+miR4488, miR-199b-5p+miR-4443, miR-199b-5p+miR-204-5p, miR-199b-5p+miR-4443+miR-4488 and miR-4443+miR-4488. The highest AUC values of 0.926 and 0.91 were observed in the case of miR-199b-5p+miR-4443 and miR-4488+miR-4443, respectively.

Finally, the level of expression of miR-199b-5p and miR-4488 in the sera of melanoma patients were determined. Coherently with the previous findings, miR-199b-5p expression levels were down-regulated in sera of melanoma patients post-MAPKi treatment as compared to sera from untreated patients (see FIG. 33, left panel). Again, coherently with previous data, miR-4488 levels were significantly increased in patients after MAPKi treatment (FIG. 33, right panel). The expression levels of these two miRNA were used to plot ROC curves. This resulted in a significant AUC value of 0.737 (FIG. 34) coherently to what observed in tumor samples (FIG. 32, first panel). These findings suggest the possibility that the simultaneous assessment of miR-4488 and miR-199b-5p in human samples could represent a valuable diagnostic tool to identify melanoma patients sensitive vs resistant to therapy with MAPK inhibitors.

Example 2: Study of the Effects of SNALP Carrying miRNA Mimics According to the Present Invention on Melanoma Cell Growth Materials and Methods Cell Lines Human melanoma cell line LOX IMVI (V600E) (EZT-LOXI-1) was from EZ Byosistems™, whereas A375 cells (ATCC® CRL-1619) were from American Type Culture Collection®. Resistant melanoma cells were selected by treating them for about two months with increasing drug concentrations every two weeks (from 50 nM to 2 μM). All human melanoma cell lines used in the present work were cultured in RPMI supplemented with 10% (vol/vol) FBS.

RNA Extraction and Real-Time PCR Analysis.

Real-time PCR was performed by TaqMan Gene Expression Assays (Applied Biosystems). Circulating Rna from patients' sera was extracted through miRNeasy Mini Kit following the manufacturer's instructions.

Cell Proliferation Assays and In Vitro Colony Formation Assays

Viability of cells was examined with 3-(4,5-dimethylthiazol-2-yl)-2,5-diphenyltetrazolium bromide Cell Titer 96 AQueous One Solution Cell Proliferation Assay (Promega), according to the manufacturer's protocol. The plates were analyzed in a Multilabel Counter (Bio-Rad Laboratories). Cell viability was also determined by crystal violet staining. Briefly, the cells were stained for 20 min at room temperature with staining solution (0.5% crystal violet in 30% methanol), washed four times with water and then dried. Cells were then dissolved in a Methanol/SDS solution and the adsorbance (595 nm) was read using a microplate ELISA reader.

Statistical Analysis Data from at least three separate experiments are presented as means±SD. P values were calculated using Student's t test and significance level has been defined as P<0.05. All experiments shown, except for the ones that involve clinical samples, were performed independently at least three times. The levels of circulating miRNAs in melanoma patients' plasma were normalized through global mean normalization (GMN) and NormFinder model.

Results

SNALPs Carrying Therapeutic miRNAs Potently Affect Melanoma Cell Growth miRNA mimics can be administered and delivered by lipid nanoparticles since the use of naked RNA-based molecules in therapy is hampered by their rapid enzymatic degradation in biological fluids (14,15). Hence the biological consequences of miRNA mimics (i.e. single miRNA or a mixture of more than one mimic) encapsulated in stable nucleic acid lipid particles (SNALPs) was tested on melanoma cells in vitro. Results obtained on SNALPs2 carrying miR-204-5p (SEQ ID NO:1) and SNALP3/miR-199b-5p (SEQ ID NO:1; SNALP3) indicate that they are able to inhibit the growth of either LOX IMVI (BRAF-V600E) BRAFi-sensitive and resistant melanoma cells as compared to SNALP1 with no content of therapeutic miRNA mimics (FIG. 1). Of note, SNALP4 which contains both miR-204-5p and miR-199b-5p has the strong inhibitory effect on both melanoma cell lines tested (FIG. 1). Hereafter, the effects of such therapeutic SNALPs were assayed on a more aggressive and metastatic melanoma cell line, namely A375 (BRAF-V600E). Results obtained at different doses of the therapeutic nanoparticles show that only SNALP4 (containing both miR-204-5p and miR-199b-5p) is able to reduce melanoma cell growth, in line with the assumption that A375 are more difficult to growth inhibit (FIG. 2).

Liquid Biopsy of Circulating microRNAs Predict Response to Therapy in Metastatic Melanoma Liquid biopsy of circulating nucleic acids promises to be a highly sensitive and specific non-invasive diagnostic modality to predict drug response or resistance. MicroRNAs (miRs) are ideal biomarkers since they can be easily detected in the circulation (11). It has been previously demonstrated that the deregulation of several miRNAs in human blood is associated with therapeutic resistance with significant AUC predictive values (10). Here, plasma liquid biopsies from melanoma patients divided into Late Progressors (LPs) upon target therapy with mean Progression Disease (PD)= or >12 months and Fast Progressors (FPs) with PD mean of = or <5 months were evaluated. Results confirm miR-4488 up-regulation and, in contrast, miR-579-3p down-regulation upon development of PD in melanoma patients' derived plasma. Of note, their dysregulations occur in statistically significative manner only in FPs as compared to LPs. These data suggest the possibility to develop miRNA-based signatures capable to distinguish drug responding from non responding patients. These initial results are being validated in a prospective study on an enlarged cohort of patients.

REFERENCES

1. A. M. Menzies, G. V. Long, Systemic treatment for BRAF-mutant melanoma: where do we go next? Lancet Oncol. 15 (August (9)) (2014) e371-e381.
2. Franklin C, Livingstone E, Roesch A, et al. Immunotherapy in melanoma: Recent advances and future directions. Eur J Surg Oncol. 2017 March; 43(3):604-611. doi: 10.1016/j.ejso.2016.07.145.
3. P. A. Ascierto, J. M. Kirkwood, J. J. Grob, E. Simeone, A. M. Grimaldi, M. Maio, et al., The role of BRAF V600 mutation in melanoma, J. Transl. Med. 10 (2012) 85.
4. Robert C., Karaszewska B., Schachter J., et al. Improved overall survival in melanoma with combined dabrafenib and trametinib. N Engl J Med. 2015 Jan. 1; 372(1):30-9. doi: 10.1056/NEJMoa1412690.
5. Moriceau G., Hugo W., Hong A., et al. Tunable-combinatorial mechanisms of acquired resistance limit the efficacy of BRAF/MEK targeting but result in melanoma drug addiction. Cancer Cell. 2015 Feb. 9; 27(2): 240-56. doi: 10.1016/j.ccell.2014.11.018.
6. Zhang G, Frederick D T, Wu L, et al. Targeting mitochondrial biogenesis to overcome drug resistance to MAPK inhibitors. J Clin Invest. 2016 May 2; 126(5): 1834-56. doi: 10.1172/JCI82661.
7. Roesch A. Tumor heterogeneity and plasticity as elusive drivers for resistance to MAPK pathway inhibition in melanoma. Oncogene. 2015 Jun. 4; 34(23):2951-7. doi: 10.1038/onc.2014.249.
8. Fattore L., Mancini R., Acunzo M., et al. miR-579-3p controls melanoma progression and resistance to target therapy. Proc Natl Acad Sci U S A. 2016 Aug. 23; 113(34): E5005-13. doi: 10.1073/pnas.1607753113.
9. Kozar I., Cesi G. et al., Impact of BRAF kinase inhibitors on the miRNomes and transcriptomes of melanoma cells, BBA—General Subjects 1861 (2017) 2980-2992.
10. Fattore L, Ruggiero C F, Pisanu M E, et al. Reprogramming miRNAs global expression orchestrates development of drug resistance in BRAF mutated melanoma. Cell Death Differ. 2018 Sep. 25. doi: 10.1038/s41418-018-0205-5.
11. Mumford S L, Towler B P, Pashler A L, et al. Circulating MicroRNA biomarkers in melanoma: tools and challenges in personalised medicine. Biomolecules. 2018 Apr. 23; 8(2):21.
12. Mansoori B, Shotorbani S S, and Baradaran B. RNA Interference and its Role in Cancer Therapy. Adv Pharm Bull, 2014, 4(4), 313-321 doi: 10.5681/apb.2014.046.
13. Bora R S, Gupta D, Mukkur T K, et al. RNA interference therapeutics for cancer: challenges and opportunities (review). Mol Med Rep. 2012 July; 6(1):9-15. doi: 10.3892/mmr.2012.871. Epub 2012 Apr. 18.
14. Wittrup A, Lieberman J. Knocking down disease: a progress report on siRNA therapeutics. Nat Rev Genet. 2015 September; 16(9):543-52. doi: 10.1038/nrg3978.
15. Di Martino M T, Campani V, Misso G, et al. In vivo activity of miR-34a mimics delivered by stable nucleic acid lipid particles (SNALPs) against multiple myeloma. PLoS One. 2014 Feb. 27; 9(2):e90005. doi: 10.1371/journal.pone.0090005. eCollection 2014.
16. Semple S C, Klimuk S K, Harasym T O, et al. Efficient encapsulation of antisense oligonucleotides in lipid vesicles using ionizable aminolipids: formation of novel small multilamellar vesicle structures. Biochim Biophys Acta. 2001 Feb. 9; 1510(1-2):152-66.
17. Campani V, De Rosa G, Misso G, et al., Lipid Nanoparticles to Deliver miRNA in Cancer. Curr Pharm Biotechnol. 2016; 17(8):741-9.
18. Ma Z, Lui W O, Fire A, Dadras S S (2009) Profiling and discovery of novel miRNAs from formalin-fixed, paraffin-embedded melanoma and nodal specimens. J Mol Diagn 11(5):420-429.

19. Fogli S, Polini B, Carpi S, et al. Identification of plasma microRNAs as new potential biomarkers with high diagnostic power in human cutaneous melanoma. Tumour Biol. 2017 May; 39(5):1010428317701646. doi: 10.1177/1010428317701646.
20. Di Costanzo E, Ingangi V, Angelini C, Carfora M F, et al. A Macroscopic Mathematical Model for Cell Migration Assays Using a Real-Time Cell Analysis. PLoS One. 2016 Sep. 28; 11(9):e0162553. doi: 10.1371/journal.pone.0162553.
21. V. S. Jones, R. Y. Huang, L. P. Chen, Z. S. Chen, L. Fu, R. P. Huang, Cytokines in cancer drug resistance: cues to new therapeutic strategies, Biochim. Biophys. Acta 1865 (April (2)) (2016) 255-265.
22. Balatti V, Nigita G, Veneziano D, Drusco A, et al. tsRNA signatures in cancer. Proc Natl Acad Sci U S A. 2017 Jul. 25; 114(30):8071-8076. doi: 10.1073/pnas.1706908114.
23. Rajabi P, Neshat A, Mokhtari M, et al. The role of VEGF in melanoma progression. J Res Med Sci. 2012 June; 17(6):534-9.
24. Sharma P S, Sharma R, Tyagi T. VEGF/VEGFR pathway inhibitors as anti-angiogenic agents: present and future. Curr Cancer Drug Targets. 2011 June; 11(5):624-53.
25. Dai L, Lou W, Zhu J, Zhou X, Di W. MiR-199a inhibits the angiogenic potential of endometrial stromal cells under hypoxia by targeting HIF-1α/VEGF pathway. Int J Clin Exp Pathol. 2015 May 1; 8(5):4735-44.
26. Schwarzenbach H, Nishida N, Calin G A, Pantel K (2014) Clinical relevance of circulating cell-free microRNAs in cancer. Nat Rev Clin Oncol 11(3):145-156

---

The invention claimed is:

1. A method of diagnosing and treating a tumor that is resistant to MAPK pathway inhibiting drugs in a subject, comprising:

obtaining a measurement of the expression, in a biological sample from the subject, of at least two, three or all of the following microRNAs:

miR-199b-5p:
(SEQ ID NO: 1)
cccaguguuuagacuaucuguuc, miR-204-5p:
(SEQ ID NO: 2)
uucccuuugucauccuaugccu, miR-4443:
(SEQ ID NO: 10)
uuggaggcguggguuuu, miR-4488:
(SEQ ID NO: 11)
aggggcgggcuccggcg, identifying the tumor as resistant to MAPK pathway inhibiting drugs based on miR-199b-5p or miR-204-5p being down-expressed in comparison with their expression in controls which do not present said resistance, or based on miR-4443 or miR-4488 being over-expressed in comparison with their expression in controls which do not present said resistance; and treating the subject by simultaneously, sequentially or separately administering to the subject a combination of:

an antagonist of at least one of miR-4443 and miR-4488 and/or a miRNA mimic of at least one of miR-199b-5p and miR-204-5p, and at least one MAPK pathway inhibiting drug, wherein said antagonist is selected from the group consisting of Locked Nucleic Acid targeting miR-4443, Locked Nucleic Acid targeting miR-4488, antimiR-4443: aaaacccacgcctccaa (SEQ ID NO:18), and antimiR-4488: cgccggagcccgccccct (SEQ ID NO:19), and wherein said miRNA mimic is selected from the group consisting of miR-199b-5p mimic: cccaguguuuagacuaucuguuc (SEQ ID NO:1), and miR-204-5p mimic: uucccuuugucauccuaugccu (SEQ ID NO:2).

2. The method of claim 1, wherein the tumor that is resistant to MAPK pathway inhibiting drugs is a melanoma tumor.

3. A method of treating a melanoma in a subject, wherein the melanoma is resistant to MAPK pathyway inhibiting drugs, the method comprising the simultaneous, sequential or separate administration to the subject a combination of:
- an antagonist of at least one of miR-4443 and miR-4488 and/or a miRNA mimic of at least one of miR-199b-5p and miR-204-5p, and
- at least one MAPK pathway inhibiting drug,
- wherein said antagonist is selected from the group consisting of Locked Nucleic Acid targeting miR-4443, Locked Nucleic Acid targeting miR-4488, antimiR-4443: aaaacccacgcctccaa (SEQ ID NO:18), and antimiR-4488: cgccggagcccgccccct (SEQ ID NO:19), and
- wherein said miRNA mimic is selected from the group consisting of miR-199b-5p mimic: cccaguguuuagacuaucuguuc (SEQ ID NO:1), and miR-204-5p mimic: uucccuuugucauccuaugccu (SEQ ID NO:2).

4. The method according to claim 3, wherein said MAPK pathway inhibiting drugs are selected from the group consisting of vemurafenib, Trametinib, dabrafenib, sorafenib, SB590885, PLX4720, XL281, RAF265, encorafenib, cobimetinib, CI-1040, PD0325901, Binimetinib, and selumetinib.

5. The method according to claim 3, wherein, when a mixture of said antagonist and/or miRNA mimic is used, said mixture is: miR-199b-5p mimic, miR-204-5p mimic and miR-579-3p mimic; miR-199b-5p mimic and miR-204-5p mimic; antimiR-4443 or LNA targeting miR-4443 and antimiR-4488 or LNA targeting miR-4488; antimiR-4488 or LNA targeting miR-4488 and miR-204-5p mimic; antimiR-4443 or LNA targeting miR-4443 and miR-204-5p mimic; miR-199b-5p mimic and antimiR-4443 or LNA targeting miR-4443; miR-199b-5p mimic and antimiR-4488 or LNA targeting miR-4488.

6. The method according to claim 3, wherein said combination is administered with at least one of the following antagonists and/or miRNA mimics:

```
antimiR-1234:
                               (SEQ ID NO: 20)
gtggggtgggtggtcaggccga
or LNA targeting miR-1234, antimiR-9-5p:
                               (SEQ ID NO: 21)
tcatacagctagataaccaaaga
or LNA targeting miR-9-5p, antimiR-1915-5p:
                               (SEQ ID NO: 22)
ggcccgggcagcaaggcaaggt
or LNA targeting miR-1915-5p, antimiR-4286:
                               (SEQ ID NO: 23)
ggtaccaggagtggggt
or LNA targeting miR-4286, antimiR-575:
                              (SEQ. ID. NO. 24)
gctcctgtccaactggctc
or LNA targeting miR-575, antimiR-630:
                               (SEQ ID NO: 25)
accttccctggtacagaatact
or LNA targeting miR-630, miR145-5p mimic:
                               (SEQ ID NO: 3)
guccaguuuucccaggaaucccu, miR-18a-5p mimic:
                               (SEQ ID NO: 4)
uaaggugcaucuagugcagauag, miR-455-3p mimic:
                               (SEQ ID NO: 5)
gcaguccaugggcauauacac, miR-107 mimic:
                               (SEQ ID NO: 6)
agcagcauuguacagggcuauca, miR-15b-5p mimic:
                               (SEQ ID NO: 7)
uagcagcacaucaugguuuaca, miR-221-3p mimic:
                               (SEQ ID NO: 8)
agcuacauugucucugcugguuuc, miR-551b-3p mimic:
                               (SEQ ID NO: 9)
gcgacccauacuuggguuucag.
```

* * * * *